United States Patent
Ono et al.

(10) Patent No.: US 8,022,225 B2
(45) Date of Patent: Sep. 20, 2011

(54) TRIAZOLE DERIVATIVE

(75) Inventors: Naoya Ono, Toshima-ku (JP);
Masakazu Sato, Toshima-ku (JP);
Fumiyasu Shiozawa, Toshima-ku (JP);
Makoto Yagi, Toshima-ku (JP); Tetsuya Yabuuchi, Toshima-ku (JP); Tetsuo Takayama, Toshima-ku (JP); Hironori Katakai, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 1103 days.

(21) Appl. No.: 11/659,103

(22) PCT Filed: Aug. 4, 2005

(86) PCT No.: PCT/JP2005/014351
§ 371 (c)(1),
(2), (4) Date: Feb. 1, 2007

(87) PCT Pub. No.: WO2006/013948
PCT Pub. Date: Feb. 9, 2006

(65) Prior Publication Data
US 2009/0131438 A1    May 21, 2009

(30) Foreign Application Priority Data

Aug. 4, 2004    (JP) ............... 2004-228394
Apr. 20, 2005   (JP) ............... 2005-121769

(51) Int. Cl.
*C07D 249/12* (2006.01)
*C07D 249/08* (2006.01)
(52) U.S. Cl. ............ 548/263.2; 548/268.2; 548/264.2
(58) Field of Classification Search .......... 548/263.2, 548/268.2, 264.2
See application file for complete search history.

(56) References Cited

U.S. PATENT DOCUMENTS

| 5,516,783 A | 5/1996 | Whittaker et al. |
| 5,910,506 A | 6/1999 | Sugimoto et al. |
| 2003/0229125 A1 | 12/2003 | Haaf et al. |
| 2005/0124654 A1 | 6/2005 | Groneberg et al. |
| 2007/0232682 A1 | 10/2007 | Beard et al. |
| 2009/0131438 A1 | 5/2009 | Ono et al. |
| 2009/0182144 A1 | 7/2009 | Ono et al. |
| 2010/0041655 A1 | 2/2010 | Ono et al. |

FOREIGN PATENT DOCUMENTS

| EP | 786455 A1 | 7/1997 |
| EP | 1 798 226 A1 | 6/2007 |
| JP | 5-194412 A | 8/1993 |
| JP | 2002-212070 A | 7/2002 |
| JP | 2002-332278 A | 11/2002 |
| JP | 2003-137894 A | 5/2003 |
| JP | 2003-530388 A | 10/2003 |
| JP | 2004/532276 A | 10/2004 |
| WO | 96/10019 A1 | 6/1996 |
| WO | 01/77089 A1 | 10/2001 |
| WO | WO 02/18395 A1 | 3/2002 |
| WO | 02/100853 A1 | 12/2002 |
| WO | 03/000679 A2 | 1/2003 |
| WO | WO 03/073986 A2 | 9/2003 |
| WO | WO 03/074008 A2 | 9/2003 |
| WO | WO 03-097028 A1 | 11/2003 |
| WO | 03/105771 A2 | 12/2003 |
| WO | WO 2004/024673 A1 | 3/2004 |
| WO | 2004/074257 A1 | 9/2004 |
| WO | 2004/089367 A1 | 10/2004 |
| WO | 2004/103279 A2 | 12/2004 |
| WO | 2005/123677 A1 | 12/2005 |
| WO | 2006/136948 A1 | 2/2006 |
| WO | 2006013948 A1 | 2/2006 |

(Continued)

OTHER PUBLICATIONS

Heinz Gehlen, et al, 2-Amino-1,3,4-oxadiazoles. VIII. Formation of 2-amino-5-aminoalkyl-1,3,4-triazoles and Triazolones, 651 Justus Liebigs Annalen Der Chemie, 128 (1962).*

Heinz Gehlen, et al, 2-Amino-1,3,4-oxadiazoles. IX. Oxidation of Aldehyde Semicarbazones to 2-amino-1,3,4-oxadiazoles and Their Conversion Into 1-acylsemicarbazides, 651 Justus Liebigs Annalen Der Chemie, 133 (1962).*

Heinz Gehlen, et al, 2-Amino-1,3,4-oxadiazoles. X. 3-alkoxy-1,2,4-triazoles by Alcoholysis of 2-amino-1,3,4-oxadiazoles, 651 Justus Liebigs Annalen Der Chemie, 137 (1962).*

(Continued)

*Primary Examiner* — Karlheinz R Skowronek
*Assistant Examiner* — Sean Basquill
(74) *Attorney, Agent, or Firm* — Sughrue Mion, PLLC

(57) ABSTRACT

A compound represented by the formula (I) below or a pharmaceutically acceptable salt thereof has an effect of inhibiting binding between S1P and its receptor Edg-1($S1P_1$), and is useful as a pharmaceutical product.

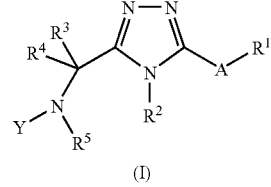

[Chemical Formula 1]

(I)

[where
A represents a sulfur atom, an oxygen atom, a formula —SO— or a formula —$SO_2$—; $R^1$ represents a hydrogen atom, an alkyl group having 1 to 6 carbon atoms or the like; $R^2$ represents an alkyl group having 1 to 6 carbon atoms, a cycloalkyl group having 3 to 8 carbon atoms or the like; $R^3$ represents a hydrogen atom or an alkyl group having 1 to 6 carbon atoms; $R^4$ represents a hydrogen atom, an alkyl group having 1 to 6 carbon atoms, a phenyl group or the like; $R^5$ represents a hydrogen atom or an alkyl group having 1 to 6 carbon atoms; and $R^6$ represents an alkyl group having 1 to 6 carbon atoms, a phenyl group or a substituted phenyl group].

26 Claims, No Drawings

FOREIGN PATENT DOCUMENTS

| WO | 2006/097489 A1 | 9/2006 |
| WO | 2006097489 A1 | 9/2006 |
| WO | 2007/083089 A1 | 7/2007 |
| WO | 2007/091570 A1 | 8/2007 |
| WO | 2007/112322 A2 | 10/2007 |
| WO | 2007/122401 A1 | 11/2007 |
| WO | 2007/129019 A1 | 11/2007 |

OTHER PUBLICATIONS

Timothy Hla, Physiological and Pathological Actions of Sphingosine 1-Phosphate, 15 Sem. Cell & Dev. Bio. 513 (2004).*

International Search Report dated Sep. 22, 2008, as issued in International Application No. PCT/JP2008/063851.

H. Gehlen, et al., "2-Amino-1, 3,4-oxidiazoles. VII. Formation of 2-amino-5-aminoalkyl-1, 3,4-oxidiazoles and their conversion into 1,2,4-triazoles and triazolones", Justus Liebigs Annalen der Chemi. vol. 651, pp. 128-132, Sep. 23, 1961, with Full English language translation.

Von Heinz Gehlen et al., "3-Alkoxy-1.2.4-Triazole Durch Alkoholyse Von 2-Amino-1.3.4 Oxdiazolen", Liebigs Ann. Chem. 1962, p. 137-141, vol. 651. and an English language translation.

H. Gehlen, et al., "2-Amino-1, 3,4-oxidiazoles. VII. Formation of 2-amino-5-aminoalky1-1, 3,4-oxidiazoles and their conversion into 1,2,4-triazoles and triazolones", Justus Liebigs Annalen der Chemi. vol. 651, pp. 128-132, Sep. 23, 1962 with Full English language translation.

M. Germana Sanna et al., "Sphingosine 1-Phosphate (S1P) Receptor Subtypes $S1P_1$ and $S1P_3$, Respectively, Regulate Lymphocyte Recirculation and Heart Rate", The Journal of Biological Chemistry, vol. 279, No. 14, Issue of Apr. 2, pp. 13839-13848, 2004.

Jeremy J. Clemens et al., "Synthesis of *Para*-Alkyl Aryl Amide Analogues of Sphingosine-1-phosphate: Discovery of Potent S1P Receptor Agonists", Bioorganic & Medicinal Chemistry Letters, 13 (2003) 3401-3404.

James R. Van Brocklyn et al., Sphingosine-1-phosphate stimulates motility and invasiveness of human glioblastoma multiforme cells, Cancer Letters, Elsevier, 2003, pp. 53-60, vol. 199.

Zdzislaw Brzozowski, 2-Mercapto-N-(Azolyl) Benzenesulphonamides I. Synthesis of N-(1,1-Dioxo-1,4,2-Benzodithianzin-3-YL)Guanidines and Their Transformations Into 2-Mercapto-N-(5-Amino-1,2,4-Triazol-3-YL) Benzenesulphonamide Dervatives with Potential Anti-HIV or Anticancer Activity, Department of Drug Technology, Faculty of Pharmacy, School of Medicine, Acta Poloniae Pharmaceutica-Drug Research, Polish Pharmaceutical Society, 1995, pp. 91-101, vol. 52, No. 2.

Guofeng Jia, et al., "Syntheses of Some New 4-Amino-5-(N-methyl-arylsulfonamido)methy1-1,2,4-triazole-3-thiones and Their Derivatives", Heteroatom Chemistry, vol. 7, No. 4, pp. 263-267, 1996.

H. Gehlen, et al., "2-Amino-1, 3,4-oxidiazoles. VIII. Formation of 2-amino-5-aminoalkyl-1,3,4-oxidiazoles and their conversion into 1,2,4-triazoles and triazolones", Chemical Abstracts, Database Accession No. 57:16892, Justus Liebigs Annalen der Chemie, vol. 651, pp. 128-132, 1962.

Supplemental European Search Report dated Oct. 13, 2009, issued in European Application No. 07708069.5.

Extended European Search Report issued Nov. 23, 2010 from the European Patent Office in a counterpart European Application No. 07713881.6 of the co-pending U.S. Appl. No. 12/278,477.

* cited by examiner

TRIAZOLE DERIVATIVE

TECHNICAL FIELD

This invention relates to novel triazole derivatives having the effect of inhibiting binding between sphingosine-1-phosphate having various physiological actions and Edg-1 (Endothelial differentiation gene receptor type-1, $S1P_1$), which is one of its receptors, and pharmaceutical products containing them as active ingredients.

BACKGROUND ART

Sphingosine-1-phosphate (hereinafter referred to as "S1P") is a physiologically active lipid which is produced upon metabolism, in cells, of sphingolipids typified by sphingomyelin. S1P is known to have wide varieties of actions, including a cell differentiation inducing action, a cell growth promoting action, control of cell motility, and an antiapoptotic action, and to show physiological actions such as angiogenesis, induction of bradycardia, activation of inflammatory cells, and activation of platelets (non-patent document 1).

Five subtypes, Edg-1($S1P_1$), Edg-3($S1P_3$), Edg-5($S1P_2$), Edg-6($S1P_4$), and Edg-8($S1P_5$), are reported as receptors of S1P (non-patent document 2).

One of them, Edg-1($S1P_1$), is expressed in large amounts in immune cells such as T cells and dendritic cells, and the vascular endothelial cells, and is suggested to contribute deeply to S1P-associated migration of T cells (non-patent document 3), migration of mast cells (non-patent document 4), emigration of T cells and B cells from lymph organs (non-patent document 5), and angiogenesis (non-patent document 6), and to be involved in autoimmune diseases such as Crohn disease, irritable colitis, Sjögren syndrome, multiple sclerosis, and systemic lupus erythematosus, and diseases such as rheumatoid arthritis, asthma, atopic dermatitis, rejection reaction after organ transplantation, cancer, retinopathy, psoriasis, osteoarthrosis, and age-related macular degeneration.

Thus, Edg-1($S1P_1$) ligands are considered to be effective for the treatment or prevention of these diseases.

So far, certain types of thiophene derivatives (non-patent document 7), phosphate ester derivatives (patent document 1, patent document 2, non-patent document 8), and thiazolidine derivatives (patent document 3) have been reported as Edg-1 ($S1P_1$) ligands. However, inhibitors having structures similar to the structure of the compound of the present invention have not been known.

Compounds similar in structure to the compound of the present invention are marketed as reagents by Bionet, but their pharmaceutical uses are completely unknown.

Patent document 1: WO02/18395
Patent document 2: Japanese Unexamined Patent Publication No. 2003-137894
Patent document 3: Japanese Unexamined Patent Publication No. 2002-332278
Non-patent document 1: J Biol Chem. 2004, 279:20555, FASEB J 2002, 16:625, Proceedings of the Japanese Society of Immunology 2003, 33:2-J-W30-20-P
Non-patent document 2: Pharmacol Res 2003, 47:401
Non-patent document 3: FASEB J 2002, 16:1874
Non-patent document 4: J Exp Med 2004, 199:959
Non-patent document 5: Nature 2004, 427:355
Non-patent document 6: J Clin Invest 2000, 106:951, Biocchim Biophys Acta 2002, 1582:222
Non-patent document 7: J Biol Chem 2004, 279:13839
Non-patent document 8: Bioorg Med Chem Lett 2003, 13:3401

DISCLOSURE OF THE INVENTION

Problems to be Solved by the Invention

It is an object of the present invention to provide a compound which has the effect of inhibiting binding between S1P and its receptor Edg-1($S1P_1$) and is useful as a pharmaceutical product.

Means for Solving the Problems

The inventors diligently conducted studies in an attempt to find ligand compounds for Edg-1($S1P_1$). As a result, they have found that certain types of triazole derivatives or their pharmaceutically acceptable salts attain this object. This finding has led to the accomplishment of the present invention.

That is, the present invention is a compound represented by the formula (I) below or a pharmaceutically acceptable salt thereof

[Chemical formula 1]

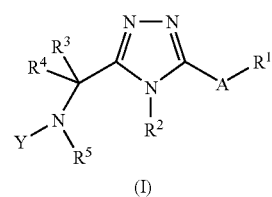

(I)

{where
A represents a sulfur atom, an oxygen atom, a group represented by the formula —SO—, or a group represented by the formula —$SO_2$—,
$R^1$ represents a hydrogen atom, an alkyl group having 1 to 16 carbon atoms, an alkenyl group having 2 to 8 carbon atoms, an alkynyl group having 2 to 8 carbon atoms, [an alkyl group having 1 to 6 carbon atoms which has been substituted by a phenyl group, "a phenyl group substituted by 1 to 5 groups selected from a phenyl group, a cyano group, a halogen atom, an alkyl group having 1 to 6 carbon atoms, a trifluoromethyl group, a methoxycarbonyl group, an alkylthio group having 1 to 6 carbon atoms, a dimethylamino group, a nitro group, and an acetamido group", a cycloalkyl group having 3 to 8 carbon atoms, a hydroxyl group, an alkylthio group having 1 to 6 carbon atoms, an alkoxy group having 1 to 6 carbon atoms, a benzyloxy group, a phenoxy group, a trifluoromethyl group, a difluoromethyl group, a benzenesulfonyl group, a naphthyl group, a tricycloalkyl group having 7 to 10 carbon atoms, a carbomethoxy (phenyl)methyl group, a diphenylmethyl group, a 1-phenylethyl group, an imidazolyl group, an indolyl group, a pyridyl group, an oxetanyl group, an oxoranyl group, a methylpiperidinyl group, a benzylpiperidinyl group, a morpholino group, a 2-oxopyrrolidin-1-yl group, a 2-oxoimidazolidin-1-yl group, a group represented by the formula

—$CO_2R^{11}$ where $R^{11}$ represents a hydrogen atom or an alkyl group having 1 to 6 carbon atoms, a group represented by the formula

[Chemical formula 2]

where $R^{12}$ and $R^{13}$ each represent a hydrogen atom or an alkyl group having 1 to 6 carbon atoms, a group represented by the formula

[Chemical formula 3]

where $R^{14}$ and $R^{15}$ each represent a hydrogen atom, an alkyl group having 1 to 6 carbon atoms, a phenyl group, or a 4-pyridylcarbonyl group, or a group represented by the formula

—$COR^{16}$ where $R^{16}$ represents an alkyl group having 1 to 6 carbon atoms, or a phenyl group], an alkenyl group having 2 to 8 carbon atoms which has been substituted by a phenyl group or a benzyloxy group, an alkynyl group having 2 to 8 carbon atoms which has been substituted by a phenyl group, a cycloalkyl group having 3 to 8 carbon atoms, a cycloalkyl group having 3 to 8 carbon atoms in which the benzene rings have been condensed, an oxoranyl group, a methylpiperidinyl group, or a group represented by the formula

[Chemical formula 4]

$R^2$ represents an alkyl group having 1 to 6 carbon atoms, a cycloalkyl group having 3 to 8 carbon atoms, a phenyl group, or [an alkyl group having 1 to 6 carbon atoms which has been substituted by a phenyl group, an alkoxy group having 1 to 6 carbon atoms, a morpholino group, a piperidino group, a group represented by the formula

[Chemical formula 5]

where $R^{21}$ represents a hydrogen atom or an alkyl group having 1 to 6 carbon atoms, or a group represented by the formula

[Chemical formula 6]

where $R^{22}$ and $R^{23}$ each represent a hydrogen atom or an alkyl group having 1 to 6 carbon atoms], $R^3$ represents a hydrogen atom or an alkyl group having 1 to 6 carbon atoms, $R^4$ represents a hydrogen atom, an alkyl group having 1 to 6 carbon atoms, a benzyl group, a substituted benzyl group, a phenethyl group, "an alkyl group having 1 to 6 carbon atoms which has been substituted by an alkoxy group having 1 to 6 carbon atoms, a halogen atom or a hydroxyl group", or a phenyl group, or $R^3$ and $R^4$ together form a 3- to 6-membered saturated hydrocarbon ring, $R^5$ represents a hydrogen atom or an alkyl group having 1 to 6 carbon atoms, and Y represents a group represented by the formula

[Chemical formula 7]

where $R^6$ represents an alkyl group having 1 to 10 carbon atoms, an alkenyl group having 2 to 8 carbon atoms, "an alkyl group having 1 to 10 carbon atoms which has been substituted by 1 to 5 groups selected from a phenyl group, a substituted phenyl group, a cycloalkyl group having 3 to 8 carbon atoms, a halogen atom, a naphthyl group, a heterocyclic group, and a substituted heterocyclic group", "an alkenyl group having 2 to 8 carbon atoms which has been substituted by 1 to 5 groups selected from a phenyl group, a substituted phenyl group, a cycloalkyl group having 3 to 8 carbon atoms, a halogen atom, a naphthyl group, a heterocyclic group, and a substituted heterocyclic group", a phenyl group, a substituted phenyl group, a naphthyl group, a naphthyl group substituted by a dimethylamino group, a heterocyclic group, or a substituted heterocyclic group, with the exception of [the compound in which A is an oxygen atom, and $R^1$ is a hydrogen atom], [the compound in which A is a sulfur atom, and $R^1$ is a hydrogen atom], [the compound in which A is a sulfur atom, and $R^3$ and $R^4$ are each a hydrogen atom at the same time], [the compound in which A is a sulfur atom, and $R^2$ is a phenyl group], [the compound in which A is a sulfur atom, $R^2$ is an ethyl group, $R^3$ and $R^5$ are each a hydrogen atom, $R^4$ is a benzyl group, $R^6$ is a 4-fluorophenyl group, and $R^1$ is a 3-methoxybenzyl group], [the compound in which A is a sulfur atom, $R^2$ is an ethyl group, $R^3$ and $R^5$ are each a hydrogen atom, $R^4$ is a benzyl group, $R^6$ is a 4-fluorophenyl group, and $R^1$ is a 3-fluorobenzyl group], [the compound in which A is a sulfur atom, $R^2$ is an ethyl group, $R^3$ and $R^5$ are each a hydrogen atom, $R^4$ is a benzyl group, $R^6$ is a 4-fluorophenyl group, and $R^1$ is a 2-propenyl group], [the compound in which A is a sulfur atom, $R^2$ is an ethyl group, $R^3$ and $R^5$ are each a hydrogen atom, $R^4$ is a benzyl group, $R^6$ is a 4-fluorophenyl group, and $R^1$ is a 4-t-butylbenzyl group], [the compound in which A is a sulfur atom, $R^2$ is an ethyl group, $R^3$ and $R^5$ are each a hydrogen atom, $R^4$ is a benzyl group, $R^6$ is a 4-fluorophenyl group, and $R^1$ is a methyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a methyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a 2-propenyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a 4-methoxybenzyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a 4-t-butylbenzyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a 3,4-dichlorobenzyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a 2-chlorobenzyl group], [the compound in which A is a sulfur atom, $R^2$ is an ethyl group, $R^3$ and $R^5$ are each a hydrogen atom, $R^4$ is a methyl group, $R^6$ is a 4-chlorophenyl group, and $R^1$ is a 3-fluorobenzyl group], [the compound in which A is a sulfur atom, $R^2$ is a methyl group, $R^3$ and $R^5$ are each a hydrogen atom, $R^4$ is a benzyl group, $R^6$ is a 4-chlorophenyl group, and $R^1$ is a 2-methyl-2-propenyl group], [the compound in which A is a sulfur atom, $R^2$ is a methyl group, $R^3$ and $R^5$ are each a hydrogen atom, $R^4$ is a benzyl group, $R^6$ is a 4-chlorophenyl group, and $R^1$ is a 2-propenyl group], [the compound in which A is a sulfur atom, $R^2$ is a methyl group, $R^3$ and $R^5$ are each a hydrogen atom, $R^4$ is a benzyl group, $R^6$ is a 4-chlorophenyl group, and $R^1$ is a methoxycarbonylmethyl group], [the compound in which A is a sulfur atom, $R^2$ is a methyl group, $R^3$ and $R^5$ are each a hydrogen atom, $R^4$ is a benzyl group, $R^6$ is a 4-chlorophenyl group, and $R^1$ is a 4-trifluoromethylbenzyl group], [the compound in which A is a sulfur atom, $R^2$ is a methyl group, $R^3$ and $R^5$ are each a hydrogen atom, $R^4$ is a benzyl group, $R^6$ is a 4-chlorophenyl group, and $R^1$ is a 3,4-dichlorobenzyl group], [the compound in which A is a sulfur atom, $R^2$ is a methyl group, $R^3$ and $R^5$ are each a hydrogen atom, $R^4$ is a benzyl group, $R^6$ is a 4-chlorophenyl group, and $R^1$ is a 4-bromobenzyl group], and [the compound in which A is a sulfur atom, $R^2$ is an ethyl group, $R^3$ and $R^5$ are each a hydrogen atom, $R^4$ is a benzyl group, $R^6$ is a 4-fluorophenyl group, and $R^1$ is a 4-methylbenzyl group]}.

Another aspect of the present invention is a pharmaceutical product comprising a compound represented by the formula (I) below or a pharmaceutically acceptable salt thereof as an active ingredient:

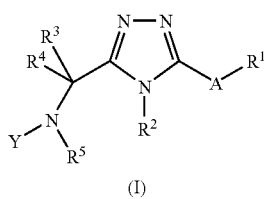

[Chemical formula 8]

(I)

{where
A represents a sulfur atom, an oxygen atom, a group represented by the formula —SO—, or a group represented by the formula —SO$_2$—,
$R^1$ represents a hydrogen atom, an alkyl group having 1 to 16 carbon atoms, an alkenyl group having 2 to 8 carbon atoms, an alkynyl group having 2 to 8 carbon atoms, [an alkyl group having 1 to 6 carbon atoms which has been substituted by a phenyl group, "a phenyl group substituted by 1 to 5 groups selected from a phenyl group, a cyano group, a halogen atom, an alkyl group having 1 to 6 carbon atoms, a trifluoromethyl group, a methoxycarbonyl group, an alkylthio group having 1 to 6 carbon atoms, a dimethylamino group, a nitro group, and an acetamido group", a cycloalkyl group having 3 to 8 carbon atoms, a hydroxyl group, an alkylthio group having 1 to 6 carbon atoms, an alkoxy group having 1 to 6 carbon atoms, a benzyloxy group, a phenoxy group, a trifluoromethyl group, a difluoromethyl group, a benzenesulfonyl group, a naphthyl group, a tricycloalkyl group having 7 to 10 carbon atoms, a carbomethoxy (phenyl)methyl group, a diphenylmethyl group, a 1-phenylethyl group, an imidazolyl group, an indolyl group, a pyridyl group, an oxetanyl group, an oxoranyl group, a methylpiperidinyl group, a benzylpiperidinyl group, a morpholino group, a 2-oxopyrrolidin-1-yl group, a 2-oxoimidazolidin-1-yl group, a group represented by the formula

where $R^{11}$ represents a hydrogen atom or an alkyl group having 1 to 6 carbon atoms,
a group represented by the formula

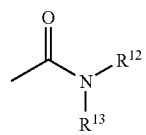

[Chemical formula 9]

where $R^{12}$ and $R^{13}$ each represent a hydrogen atom or an alkyl group having 1 to 6 carbon atoms,
a group represented by the formula

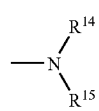

[Chemical formula 10]

where $R^{14}$ and $R^{15}$ each represent a hydrogen atom, an alkyl group having 1 to 6 carbon atoms, a phenyl group, or a 4-pyridylcarbonyl group,
or a group represented by the formula

where $R^{16}$ represents an alkyl group having 1 to 6 carbon atoms, or a phenyl group],
an alkenyl group having 2 to 8 carbon atoms which has been substituted by a phenyl group or a benzyloxy group, an alkynyl group having 2 to 8 carbon atoms which has been substituted by a phenyl group, a cycloalkyl group having 3 to 8 carbon atoms, a cycloalkyl group having 3 to 8 carbon atoms in which the benzene rings have been condensed, an oxoranyl group, a methylpiperidinyl group, or a group represented by the formula

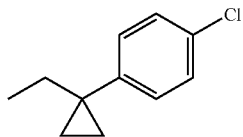

$R^2$ represents an alkyl group having 1 to 6 carbon atoms, a cycloalkyl group having 3 to 8 carbon atoms, a phenyl group, or [an alkyl group having 1 to 6 carbon atoms which has been substituted by a phenyl group, an alkoxy group having 1 to 6 carbon atoms, a morpholino group, a piperidino group, a group represented by the formula

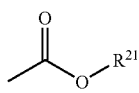

where $R^{21}$ represents a hydrogen atom or an alkyl group having 1 to 6 carbon atoms,
or a group represented by the formula

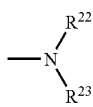

where $R^{22}$ and $R^{23}$ each represent a hydrogen atom or an alkyl group having 1 to 6 carbon atoms],
$R^3$ represents a hydrogen atom or an alkyl group having 1 to 6 carbon atoms,
$R^4$ represents a hydrogen atom, an alkyl group having 1 to 6 carbon atoms, a benzyl group, a substituted benzyl group, a phenethyl group, "an alkyl group having 1 to 6 carbon atoms which has been substituted by an alkoxy group having 1 to 6 carbon atoms, a halogen atom or a hydroxyl group", or a phenyl group, or
$R^3$ and $R^4$ together form a 3- to 6-membered saturated hydrocarbon ring,
$R^5$ represents a hydrogen atom or an alkyl group having 1 to 6 carbon atoms, and
Y represents a group represented by the formula

where $R^6$ represents an alkyl group having 1 to 10 carbon atoms, an alkenyl group having 2 to 8 carbon atoms, "an alkyl group having 1 to 10 carbon atoms which has been substituted by 1 to 5 groups selected from a phenyl group, a substituted phenyl group, a cycloalkyl group having 3 to 8 carbon atoms, a halogen atom, a naphthyl group, a heterocyclic group, and a substituted heterocyclic group", "an alkenyl group having 2 to 8 carbon atoms which has been substituted by 1 to 5 groups selected from a phenyl group, a substituted phenyl group, a cycloalkyl group having 3 to 8 carbon atoms, a halogen atom, a naphthyl group, a heterocyclic group, and a substituted heterocyclic group", a phenyl group, a substituted phenyl group, a naphthyl group, a naphthyl group substituted by a dimethylamino group, a heterocyclic group, or a substituted heterocyclic group}.

Still another aspect of the present invention is the compound of the formula (I) or the pharmaceutically acceptable salt thereof according to claim 1 wherein the portion corresponding to Y is a hydrogen atom, A is an oxygen atom, and $R^5$ is a hydrogen atom, and is an intermediate useful for producing the compound of the formula (I).

In the present invention, the alkyl group having 1 to 16 carbon atoms refers to a straight-chain or branched-chain alkyl group having 1 to 16 carbon atoms. Its examples are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, an n-hexyl group, an n-heptyl, an n-octyl group, and an n-hexadecyl group.

The alkyl group having 1 to 6 carbon atoms refers to a straight-chain or branched-chain alkyl group having 1 to 6 carbon atoms. Its examples are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, and an n-hexyl group.

The alkyl group having 1 to 4 carbon atoms refers to a straight-chain or branched-chain alkyl group having 1 to 4 carbon atoms. Its examples are a methyl group, an ethyl group, an n-propyl group, an isopropyl group, an n-butyl group, an isobutyl group, a tert-butyl group, and a sec-butyl group.

The alkenyl group having 2 to 8 carbon atoms refers to a straight-chain or branched-chain alkenyl group having 2 to 8 carbon atoms. Its examples are a vinyl group, an allyl group, a 1-propenyl group, an isopropenyl group, a 1-butenyl group, a 2-butenyl group, a 3-butenyl group, a 1,3-butadienyl group, a 2-methylallyl group, a 2-methyl-propenyl group, a 2-pentenyl group, and a 3-methyl-but-2-enyl group.

The alkenyl group having 3 to 5 carbon atoms refers to a straight-chain or branched-chain alkenyl group having 3 to 5 carbon atoms. Its examples are an allyl group, a 1-propenyl group, an isopropenyl group, a 1-butenyl group, a 2-butenyl group, a 3-butenyl group, a 1,3-butadienyl group, a 2-methylallyl group, a 2-methyl-propenyl group, and a 4-pentenyl group.

The alkynyl group having 2 to 8 carbon atoms refers to a straight-chain or branched-chain alkynyl group having 2 to 8 carbon atoms. Its examples are an ethynyl group, a 2-propynyl group, a 2-butynyl group, a 1-methyl-prop-2-ynyl group, a 2-pentynyl group, and a 4-pentynyl group.

The cycloalkyl group having 3 to 8 carbon atoms refers to a cycloalkyl group having 3 to 8 carbon atoms, and its examples are a cyclopropyl group, a cyclobutyl group, a cyclopentyl group, a cyclohexyl group, a cycloheptyl group, and a cyclooctyl group.

The cycloalkyl group having 3 to 6 carbon atoms refers to a cycloalkyl group having 3 to 6 carbon atoms, and its examples are a cyclopropyl group, a cyclobutyl group, a cyclopentyl group, and a cyclohexyl group.

The halogen atom refers to a fluorine atom, a chlorine atom, a bromine atom, or an iodine atom.

The alkylthio group having 1 to 6 carbon atoms refers to a straight-chain or branched-chain alkylthio group having 1 to 6 carbon atoms. Its examples are a methylthio group, an ethylthio group, a propylthio group, an isopropylthio group, a butylthio group, an isobutylthio group, a pentylthio group, a hexylthio group, and an allylthio group.

The alkoxy group having 1 to 6 carbon atoms refers to a straight-chain or branched-chain alkoxy group having 1 to 6 carbon atoms. Its examples are a methoxy group, an ethoxy group, a propoxy group, an isopropoxy group, a butoxy group, an isobutoxy group, a sec-butoxy group, a tert-butoxy group, a pentyloxy group, a hexyloxy group, and an allyloxy group.

The cycloalkyl group having 3 to 8 carbon atoms refers to a cycloalkyl group having 3 to 8 carbon atoms, and its examples are a cyclopropyl group, a cyclobutyl group, a cyclopentyl group, a cyclohexyl group, a cycloheptyl group, and a cyclooctyl group.

The tricycloalkyl group having 7 to 10 carbon atoms refers to a tricycloalkyl group having 7 to 10 carbon atoms, and includes, for example, an adamantyl group.

The cycloalkyl group having 3 to 8 carbon atoms in which the benzene rings have been condensed includes, for example, a 1,2,3,4-tetrahydronaphthalenyl group, and an indanyl group.

The substituted benzyl group refers to a benzyl group substituted by (1 to 2 groups selected from a phenyl group, a halogen atom, a methyl group, a methoxy group, a trifluoromethyl group, or a hydroxyl group). Its examples are a 4-phenylbenzyl group, a 3,4-dichlorobenzyl group, a 4-methylbenzyl group, and a 4-methoxybenzyl group.

As the 3- to 6-membered saturated hydrocarbon ring, cyclopropane, cyclobutane, cyclopentane, and cyclohexane can be named.

The alkyl group having 1 to 10 carbon atoms refers to a straight-chain or branched-chain alkyl group having 1 to 10 carbon atoms. Its examples are a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, an n-hexyl group, and an n-decyl group.

The substituted phenyl group refers to a phenyl group substituted by 1 to 5 groups selected, for example, from a phenyl group, a methoxy group, a phenyl group substituted by an acetyl group, an oxazolyl group, a pyrazolyl group, a methylpyrimidinyl group, a cyano group, a halogen atom, an alkyl group having 1 to 6 carbon atoms, a trifluoromethyl group, a hydroxyl group, an alkoxy group having 1 to 6 carbon atoms, a cyanoethoxy group, a phenoxy group, a phenoxy group substituted by a methoxy group, a pyridinyloxy group, an acetyl group, a benzoyl group, a pyridinecarbonyl group, a methoxycarbonyl group, a methoxycarbonylethyl group, an alkylthio group having 1 to 6 carbon atoms, a dimethylamino group, a nitro group, an acetamido group, a sulfamoyl group, a methanesulfonyl group, a benzenesulfonyl group, a pyrrolidinesulfonyl group, a morpholinesulfonyl group, a methylureido group, a butylureido group, a methoxyethylureido group, a trimethylureido group, a morpholinecarbonylamino group, and a pyridinylethoxycarbonylamino group.

The heterocyclic group refers to a saturated or unsaturated monocyclic or polycyclic heterocyclic group having 1 to 6 hetero-atoms such as an oxygen atom, a sulfur atom, and a nitrogen atom. Its examples are an imidazolyl group, a pyrazolyl group, a thiazolyl group, an oxazolyl group, an isoxazolyl group, a furyl group, a thienyl group, a pyrrolyl group, a pyridyl group, a pyrimidinyl group, a pyrazinyl group, an indolyl group, a quinolyl group, an isoquinolyl group, a benzofuranyl group, a benzothienyl group, a dihydrobenzofuranyl group, a cumarinyl group, a 2,3-dihydrobenzo[1,4]dioxinyl group, a 3,4-dihydro-2H-benzo[b][1,4]dioxepinyl group, a benzo[1,3]dioxolyl group, a 2-oxo-2,3-dihydrobenzoxazolyl group, a benzo[1,2,5]thiadiazolyl group, a 4-methyl-3,4-dihydro-2H-benzo[1,4]oxazinyl group, and a phthalimido group.

The substituted heterocyclic group refers to the above-mentioned heterocyclic group substituted by 1 to 5 substituents selected from a halogen atom, an alkyl group having 1 to 6 carbon atoms, a methoxycarbonyl group, a benzenesulfonyl group, and an oxazolyl group.

The pharmaceutically acceptable salt refers to a salt with an alkali metal, an alkaline earth metal, ammonium, an alkylammonium or the like, or a salt with a mineral acid or an organic acid. Its examples are a sodium salt, a potassium salt, a calcium salt, an ammonium salt, an aluminum salt, a triethylammonium salt, an acetate, a propionate, a butyrate, a formate, a trifluoroacetate, a maleate, a tartrate, a citrate, a stearate, a succinate, an ethylsuccinate, a lactobionate, a gluconate, a glucoheptonate, a benzoate, a methanesulfonate, an ethanesulfonate, a 2-hydroxyethanesulfonate, a benzenesulfonate, a p-toluenesulfonate, a lauryl sulfate, a malate, an aspartate, a glutamate, an adipate, a salt with cysteine, a salt with N-acetylcysteine, a hydrochloride, a hydrobromide, a phosphate, a sulfate, a hydroiodide, a nicotinate, an oxalate, a picrate, a thiocyanate, an undecanoate, a salt with an acrylic polymer, and a salt with a carboxyvinyl polymer.

The compound of the present invention may be present as a stereoisomer such as an optical isomer, a diastereomer, or a geometric isomer. All of these stereoisomers and their mixtures are included in the compounds of the present invention.

The compound of the present invention can be synthesized, for example, by the methods shown below.

(1) A compound represented by the following formula (a)

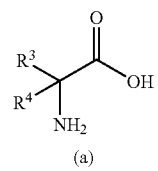

[Chemical formula 15]

(a)

where $R^3$ and $R^4$ are as defined above, is reacted with a compound represented by the formula R'OH (where R' represents an alkyl group having 1 to 6 carbon atoms) in the presence of a reagent such as trimethylsilyl chloride. Then, the product is reacted with a compound represented by the following formula (b)

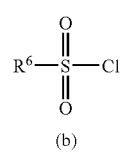

[Chemical formula 16]

(b)

where $R^6$ is as defined above, in a solvent, or without a solvent, in the presence of a base to obtain a compound represented by the following formula (c)

[Chemical formula 17]

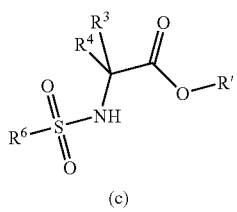

(c)

where $R^3$, $R^4$, $R^6$ and R' are as defined above.

(2) The compound represented by the formula (c) is reacted with hydrazine in a solvent or under solventless conditions to obtain a compound represented by the following formula (d)

[Chemical formula 18]

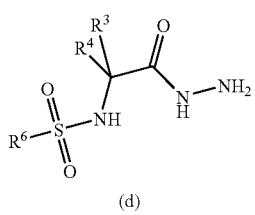

(d)

where $R^3$, $R^4$ and $R^6$ are as defined above.

(3) The resulting compound (d) is reacted with a compound represented by the following formula (e)

$$R^2-N=C=S \quad (e)$$

where $R^2$ is as defined above,
in a solvent or under solventless conditions to obtain a compound represented by the following formula (f)

[Chemical formula 19]

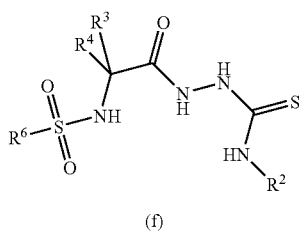

(f)

where $R^2$, $R^3$, $R^4$ and $R^6$ are as defined above.

(4) The resulting compound (f) is cyclized by a base in a solvent or under solventless conditions to obtain a compound represented by the following formula (g)

[Chemical formula 20]

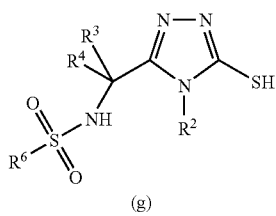

(g)

where $R^2$, $R^3$, $R^4$ and $R^6$ are as defined above.

(5) The resulting compound (g) is reacted with a compound represented by the following formula (h)

$$R^{18}\text{-L} \quad (h)$$

where $R^{18}$ has the same meaning as that of the aforementioned $R^1$ with the exception of a hydrogen atom, and L represents a leaving group, the leaving group referring, for example, to a halogen atom such as a chlorine atom, a bromine atom, or an iodine atom, or an alkylsulfonyloxy group or an arylsulfonyloxy group such as a methanesulfonyloxy group or a p-toluenesulfonyloxy group, in a solvent or under solventless conditions in the presence of a base, whereby the compound of the present invention represented by the following formula (i)

[Chemical formula 21]

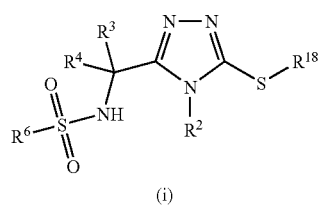

(i)

where $R^{18}$, $R^2$, $R^3$, $R^4$ and $R^6$ are as defined above, can be synthesized.

(6) Also, the compound of the present invention represented by the above formula (i) is reacted with a compound represented by the following formula (j)

$$R^{51}\text{-L} \quad (j)$$

where $R^{51}$ represents an alkyl group having 1 to 6 carbon atoms, and L is as defined above,
in a solvent or under solventless conditions in the presence of a base, whereby there can be synthesized another compound of the present invention represented by the following formula (k)

[Chemical formula 22]

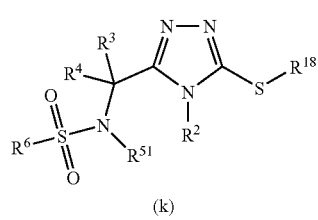

(k)

where $R^{18}$, $R^2$, $R^3$, $R^4$, $R^{51}$ and $R^6$ are as defined above.

(7) Further, the compound represented by the formula (i) or (k) above is reacted with an oxidizing agent in a solvent, whereby still another compound of the present invention represented by the following formula (l)

[Chemical formula 23]

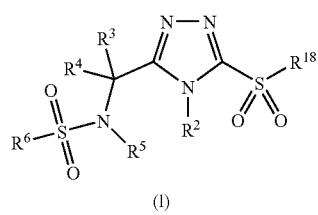

(l)

where $R^{18}$, $R^2$, $R^3$, $R^4$, $R^5$ and $R^6$ are as defined above, can be synthesized.

(8) Then, the compound represented by the above formula (l) is reacted with a compound represented by the formula $$R^{18}\text{-}A^1\text{-}H \quad (m)$$

where $A^1$ represents a sulfur atom or an oxygen atom, and $R^{18}$ is as defined above,
in a solvent or under solventless conditions in the presence of a base, whereby yet another compound of the present invention represented by the following formula (n)

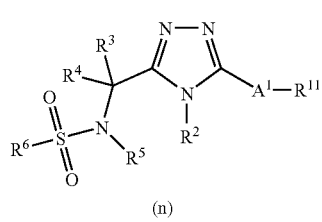

[Chemical formula 24]

(n)

where $A^1$, $R^{18}$, $R^2$, $R^3$, $R^4$, $R^5$ and $R^6$ are as defined above, can be synthesized.

Alternatively, the compound of the present invention can be synthesized by the method shown below.

(2-1) A compound represented by the following formula (o)

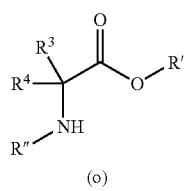

[Chemical formula 25]

(o)

where R" represents a protective group for an amino group, such as a t-butoxycarbonyl group or a benzyloxycarbonyl group, and $R^3$, $R^4$, and R' are as defined above,
is reacted with hydrazine in a solvent or under solventless conditions to obtain a compound represented by the following formula (p)

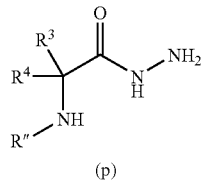

[Chemical formula 26]

(p)

where $R^3$, $R^4$ and R" are as defined above.

(2-2) The resulting compound of the formula (p) is reacted with a compound represented by the following formula (e)

$$R^2\text{—}N\text{=}C\text{=}S \quad (e)$$

where $R^2$ is as defined above,
in a solvent or under solventless conditions to obtain a compound represented by the following formula (q)

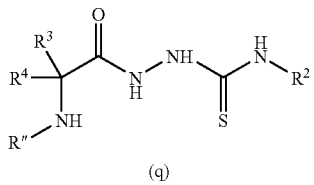

[Chemical formula 27]

(q)

where $R^2$, $R^3$, $R^4$ and R" are as defined above.

(2-3) The resulting compound of the formula (q) is cyclized by a base in a solvent or under solventless conditions to obtain a compound represented by the formula (r)

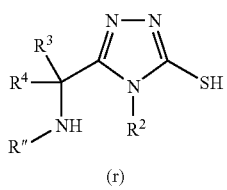

[Chemical formula 28]

(r)

where $R^2$, $R^3$, $R^4$ and R" are as defined above.

(2-4) The resulting compound of the formula (r) is reacted with a compound represented by the following formula (h)

$$R^{18}\text{-L} \quad (h)$$

where $R^{18}$ and L are as defined above,
in a solvent or under solventless conditions in the presence of a base to obtain a compound represented by the following formula (s)

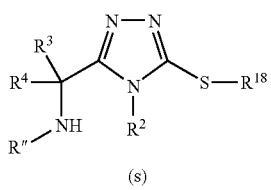

[Chemical formula 29]

(s)

where $R^{18}$, $R^2$, $R^3$, $R^4$ and R" are as defined above.

(2-5) The resulting compound of the formula (s) is reacted with an oxidizing agent in a solvent to obtain a compound represented by the following formula (t)

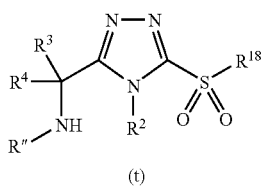

[Chemical formula 30]

(t)

where $R^{18}$, $R^2$, $R^3$, $R^4$ and R" are as defined above.

(2-6) The resulting compound of the formula (t) is subjected to deprotection of the amino group under ordinary conditions, such as reaction with an acid, in a solvent to obtain a compound represented by the following formula (u)

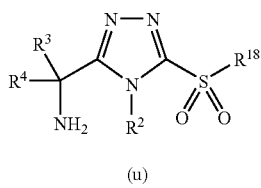

(u)

where $R^{18}$, $R^2$, $R^3$ and $R^4$ are as defined above, or a salt of the compound.

(2-7) The resulting compound of the formula (u) is reacted with a compound represented by the following formula (m)

(m)

where $A^1$ and $R^{18}$ are as defined above,
in a solvent or under solventless conditions in the presence of a base to carry out the formation of a salt, as appropriate, thereby obtaining a compound represented by the following formula (v)

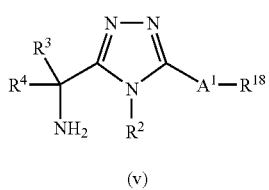

(v)

where $A^1$, $R^{18}$, X, $R^2$, $R^3$ and $R^4$ are as defined above, or a pharmaceutically acceptable salt thereof.

(2-8) The resulting compound of the formula (v) is reacted with a compound represented by the following formula (b)

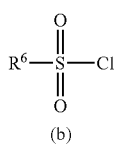

(b)

where $R^6$ is as defined above,
in a solvent or under solventless conditions in the presence of a base, whereby the compound of the present invention represented by the following formula (w)

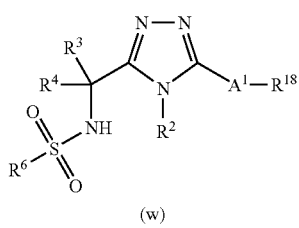

(w)

where $A^1$, $R^{18}$, $R^2$, $R^3$, $R^4$ and $R^6$ are as defined above, can be obtained.

(2-9) The resulting compound of the present invention, represented by the formula (w), is reacted with a compound represented by the following formula (j)

(j)

where $R^{51}$ and L are as defined above,
in a solvent or under solventless conditions in the presence of a base, whereby another compound of the present invention represented by the following formula (x)

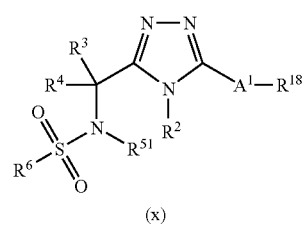

(x)

where $A^1$, $R^{18}$, $R^2$, $R^3$, $R^4$, $R^{51}$ and $R^6$ are as defined above, can be obtained.

Examples of the base used in the above reactions are alkali metal salts such as sodium carbonate, potassium carbonate, cesium carbonate, sodium bicarbonate, potassium bicarbonate, sodium hydroxide, dimsyl sodium, sodium hydride, sodium amide, and tert-butyl potassium, amines such as triethylamine, diisopropylamine, pyrrolidine and piperidine, sodium acetate, and potassium acetate.

Examples of the acid are inorganic acids (for example, hydrochloric acid, hydrobromic acid, hydroiodic acid, sulfuric acid and nitric acid), and organic acids (for example, trifluoroacetic acid, p-toluenesulfonic acid, and methanesulfonic acid).

As the oxidizing agent, there can be used, for example, organic peracids such as m-perchlorobenzoic acid, magnesium monoperphthalate hexahydrate, peracetic acid, and performic acid, inorganic and organic peroxides such as hydrogen peroxide, urea hydrogen peroxide adduct/phthalic anhydride, tert-butyl hydroperoxide, and cumene hydroperoxide, sodium periodate, Oxone (registered trademark), N-bromosuccinimide, N-chlorosuccinimide, Chloramine-T, tert-butyl hypochlorite, iodobenzene diacetate, and bromo-1, 4-diazabicyclo[2,2,2]octane addition complex.

As the reaction solvent, there can be used, for example, water, alcohols such as methanol, ethanol, isopropyl alcohol, and tert-butyl alcohol, ethers such as dioxane and tetrahydrofuran, and solvents inert to reactions, such as dimethylformamide, N,N'-dimethylacetamide, N,N'-dimethylpropyleneurea (DMPU), hexamethylphosphoramide (HMPA), dimethyl sulfoxide, pyridine, methylene chloride, chloroform, acetone, acetic acid, and benzene.

The reaction can be performed at atmospheric pressure, under pressurized conditions, under microwave irradiation, etc. at an appropriate temperature selected within the range of −78° C. to the boiling point of the solvent for the reaction.

When the compound of the present invention is to be used as a pharmaceutical product, vehicles, bulking agents, pH regulators, solubilizers, etc. in common use are added to the compound of the present invention, the resulting blends are formed into tablets, granules, pills, capsules, powders, liquids and solutions, suspensions, injections, etc. by pharmaceutical manufacturing techniques in common use, and the resulting preparations can be administered orally or as injections or as agents for topical application.

The compound of the present invention can be administered to an adult patient in a daily dose of 1 to 1,000 mg given singly or as several divided portions. This dose can be increased or decreased, as appropriate, depending on the type of the disease, the age, body weight and symptoms of the patient, and so on.

Effects of the Invention

The compound of the present invention has been found to be a potent Edg-1($S1P_1$) ligand, as demonstrated in the Test Examples to be described later.

BEST MODE FOR CARRYING OUT THE INVENTION

The present invention will be described in further detail by the following Examples and Test Examples:

EXAMPLE 1

4-Chloro-N-[1-(5-mercapto-4-methyl-4H-1,2,4-triazol-3-yl)butyl]benzenesulfonamide (Compound 128)

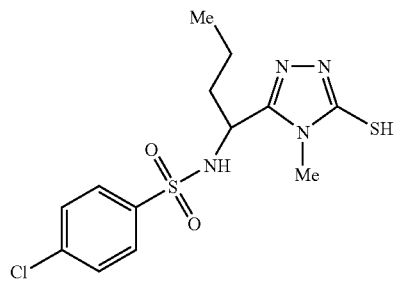

[Chemical formula 36]

(1) Trimethylchlorosilane (12.4 ml) was added, at room temperature, to a methanol (37 ml) suspension of DL-norvaline (2.157 g), and the mixture was stirred for 2 days at room temperature, and then heated under reflux for 3 hours.

The reaction mixture was cooled to room temperature, and then the solvent was distilled off under reduced pressure. The resulting light yellow solid was dissolved in chloroform (37 ml), and triethylamine (10.3 ml) and 4-chlorobenzenesulfonyl chloride (3.886 g) were added at 0° C., followed by stirring the mixture for 2 hours at room temperature. The reaction mixture was added to an aqueous solution (120 ml) of hydrochloric acid (2 mols/liter), and the mixture was extracted with ethyl acetate (200 ml), followed by washing the extract with a saturated aqueous solution of sodium chloride (100 ml×2). The organic layer was dried over anhydrous magnesium sulfate, and then the solvent was distilled off under reduced pressure to obtain 2-{[(4-chlorophenyl)sulfonyl]amino}pentanoic acid methyl ester (4.592 g) as a light yellow oily substance.

$^1$H NMR (300 MHz, $CDCl_3$) δ ppm: 0.89 (t, J=7.3 Hz, 3H), 1.20-1.80 (m, 4H), 3.52 (s, 3H), 3.87-3.98 (m, 1H), 5.11 (d, J=9.5 Hz, 1H), 7.47 (d, J=8.9 Hz, 2H), 7.77 (d, J=8.9 Hz, 2H)

(2) To a methanol (50 ml) solution of the 2-{[(4-chlorophenyl)sulfonyl]amino}pentanoic acid methyl ester (4.590 g) obtained in Example 1-(1), hydrazine monohydrate (21.8 ml) was added at room temperature, and the mixture was stirred for 14 hours at room temperature. From the reaction mixture, the solvent was distilled off under reduced pressure, and water (150 ml) was added to the residue. The mixture was extracted with ethyl acetate (200 ml), and washed with a saturated aqueous solution of sodium chloride (100 ml×2).

The organic layer was dried over anhydrous magnesium sulfate, and then the solvent was distilled off under reduced pressure to obtain 4-chloro-N-[1-(hydrazinocarbonyl)butyl]benzenesulfonamide (4.368 g).

Melting point: 120.0-120.5° C.

$^1$H NMR (300 MHz, DMSO-$d_6$) δ ppm: 0.74 (t, J=7.3 Hz, 3H), 0.98 1.52 (m, 4H), 3.63 (t, J=7.2 Hz, 1H), 3.94 4.10 (m, 2H), 7.63 (d, J=8.9 Hz, 2H), 7.75 (d, J=8.9 Hz, 2H), 8.08 (s, 1H), 9.10 (s, 1H)

(3) Methyl isothiocyanate (683 mg) was added, at room temperature, to an ethanol (85 ml) solution of the 4-chloro-N-[1-(hydrazinocarbonyl)butyl]benzenesulfonamide (2.596 g) obtained in Example 1-(2). The mixture was stirred for 30 minutes, and then stirred for 2 hours under reflux conditions. The solvent was distilled off from the reaction mixture to obtain a solid. The solid was washed with chloroform (100 ml), and then dried to obtain 2-(2-{[(4-chlorophenyl)sulfonyl]amino}pentanoyl)-N-methylhydrazine carbothioamide (2.868 g).

Melting point: 191.0-195.0° C.

$^1$H NMR (300 MHz, DMSO-$d_6$) δ ppm: 0.71 (t, J=7.3 Hz, 3H), 1.00 1.64 (m, 4H), 2.88 (d, J=4.2 Hz, 3H), 3.56 3.75 (m, 1H), 7.26 7.46 (m, 1H), 7.66 (d, J=8.7 Hz, 2H), 7.83 (d, J=8.7 Hz, 2H), 9.29 (s, 1H), 10.00 (s, 1H)

(4) An aqueous solution (8.5 ml) of sodium hydroxide (1 mol/liter) was added, at room temperature, to a mixed solution in methanol (9.5 ml) and dioxane (19 ml) of the 2-(2-{[(4-chlorophenyl)sulfonyl]amino}pentanoyl)-N-methylhydrazine carbothioamide (2.157 g) obtained in Example 1-(3). The mixture was stirred for 30 minutes, and then stirred for 30 minutes at 85° C. The solvent was distilled off from the reaction mixture, and an aqueous solution (20 ml) of hydrochloric acid (0.5 mol/liter) was added to the residue. The mixture was extracted with ethyl acetate (100 ml), and washed with a saturated aqueous solution (100 ml) of sodium chloride.

The organic layer was dried over anhydrous magnesium sulfate, and then the solvent was distilled off under reduced pressure to obtain Compound 128 (2.177 g).

$^1$H NMR (300 MHz, $CDCl_3$) δ ppm: 0.89 (t, J=7.3 Hz, 3H), 1.20 1.95 (m, 4H), 3.58 (s, 3H), 4.44 4.57 (m, 1H), 6.59 6.76 (m, 1H), 7.45 (d, J=8.5 Hz, 2H), 7.69 (d, J=8.5 Hz, 2H), 11.41 (s, 1H)

EXAMPLE 2

N-{1-[(5-allylthio)-4-methyl-4H-1,2,4-triazol-3-yl]butyl}-4-chlorobenzenesulfonamide (Compound 125)

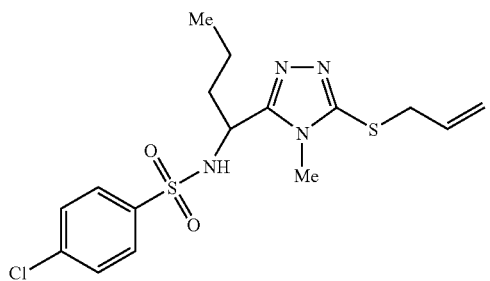

[Chemical formula 37]

Diisopropylamine (0.407 ml) and allyl bromide (0.218 ml) were added, at room temperature, to a tetrahydrofuran (9.7 ml) solution of the 4-chloro-N-[1-(5-mercapto-4-methyl-4H-1,2,4-triazol-3-yl)butyl]benzenesulfonamide (Compound 128) (698 mg) obtained in Example 1-(4), and the mixture was stirred overnight at room temperature. The solvent was distilled off from the reaction mixture under reduced pressure. The resulting residue was dissolved in ethyl acetate (100 ml), and the solution was washed sequentially with an aqueous solution (50 ml) of hydrochloric acid (1 mol/liter) and a saturated aqueous solution (100 ml) of sodium chloride. The organic layer was dried over anhydrous magnesium sulfate, and then the solvent was distilled off under reduced pressure. The residue was recrystallized from a solvent mixture of hexane (20 ml) and ethyl acetate (15 ml) for purification, thereby obtaining Compound 125 (590 mg).

Melting point: 161.5-162.0° C.

$^1$H NMR (300 MHz, CDCl$_3$) δ ppm: 0.86 (t, J=7.3 Hz, 3H), 1.15 1.35 (m, 2H), 1.65 1.96 (m, 2H), 3.39 (s, 3H), 3.73 3.80 (m, 2H), 4.37 4.49 (m, 1H), 5.07 5.27 (m, 2H), 5.85 6.01 (m, 2H), 7.40 (d, J=8.9 Hz, 2H), 7.70 (d, J=8.9 Hz, 2H)

EXAMPLE 3

N-{(1R)-1-[5-(benzylthio)-4-ethyl-4H-1,2,4-triazol-3-yl]ethyl}-4-chloro-benzenesulfonamide (Compound 5)

[Chemical formula 38]

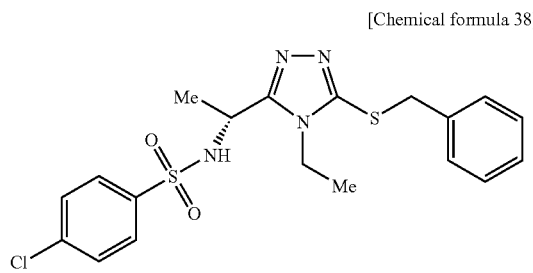

Mesyl chloride (25.8 mg) and triethylamine (0.055 ml) were added to a chloroform (0.9 ml) solution of benzyl alcohol (16.2 mg), and the mixture was stirred for 3 hours at room temperature. The reaction mixture was eluted by NH-type silica gel (Chromatorex, Fuji Silysia Chemical Ltd.) column chromatography using tetrahydrofuran as a solvent to obtain methanesulfonic acid benzyl ester. To a tetrahydrofuran (0.9 ml) solution of the methanesulfonic acid benzyl ester, 4-chloro-N-[(1R)-1-(4-ethyl-5-mercapto-4H-1,2,4-triazol-3-yl)ethyl]benzenesulfonamide (Compound 90) (17.3 mg) obtained by performing the same procedure as in Example 1 using the corresponding raw materials, and potassium t-butoxide (8.4 mg) were added, followed by stirring the mixture for 20 hours at 40° C. PSA (polymer supported amine) (0.15 ml) was added to the reaction mixture, and the resulting mixture was stirred for 4 hours at room temperature. The reaction mixture was eluted with ethyl acetate and tetrahydrofuran, and the solvents were distilled off. The resulting residue was eluted by NH-type silica gel column chromatography using tetrahydrofuran as a solvent, and the eluate was purified by silica gel column chromatography to obtain Compound 5 (2.3 mg).

$^1$H NMR (200 MHz, DMSO-d$_6$) δ ppm: 1.10 (t, J=7.1 Hz, 3H), 1.25 (d, J=6.8 Hz, 3H), 3.62 3.96 (m, 2H), 4.36 (s, 2H), 4.55 4.78 (m, 1H), 7.15 7.47 (m, 5H), 7.64 (d, J=8.6 Hz, 2H), 7.77 (d, J=8.6 Hz, 2H), 8.52 (d, J=8.6 Hz, 1H)

EXAMPLE 4

4-Chloro-N-{(1R)-1-[4-ethyl-5-(methylsulfinyl)-4H-1,2,4-triazol-3-yl]ethyl}benzenesulfonamide (Compound 180, Compound 181)

[Chemical formula 39]

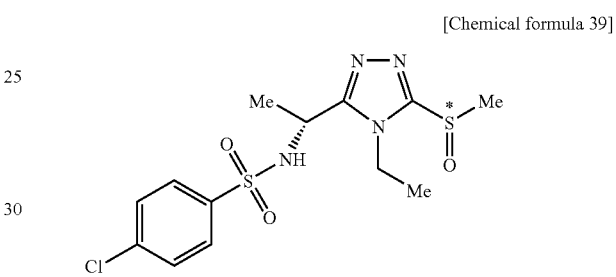

To a chloroform (18 ml) solution of 4-chloro-N-{(1R)-1-[4-ethyl-5-(methylthio)-4H-1,2,4-triazol-3-yl]ethyl}benzenesulfonamide (Compound 1) (329 mg) obtained by performing the same procedure as in Examples 1 and 2 using the corresponding raw materials, m-perchlorobenzoic acid (157 mg) was added under ice-cooling conditions. The mixture was stirred for 30 minutes at 0° C., and then stirred overnight at room temperature. The reaction solution was washed with a saturated aqueous solution (20 ml) of sodium bicarbonate. The organic layer was dried over anhydrous magnesium sulfate, and then the solvent was distilled off under reduced pressure. The resulting residue was eluted by silica gel flash column chromatography using a solvent mixture of acetone and ethyl acetate. The eluate was developed twice by preparative TLC (Merck, analytical TLC plate, 20×20 cm, Silicagel 60F$_{254}$×4 plates) using ethyl acetate as a solvent. Then, the developed substances were eluted using a 5% methanol/chloroform mixed solution to obtain Compound 180 (14 mg) of low polarity and Compound 181 (21 mg) of high polarity (Compound 180 and Compound 181: diastereomers).

Compound 180 of low polarity: $^1$H NMR (300 MHz, CDCl$_3$) δ ppm: 1.47 (t, J=7.2 Hz, 3H), 1.54 (d, J=6.8 Hz, 3H), 3.26 (s, 3H), 4.18 4.46 (m, 2H), 4.63 4.78 (m, 1H), 5.95 (d, J=9.6 Hz, 1H), 7.45 (d, J=8.5 Hz, 2H), 7.70 (d, J=8.5 Hz, 2H)

Compound 181 of high polarity: $^1$H NMR (300 MHz, CDCl$_3$) δ ppm: 1.47 (t, J=7.3 Hz, 3H), 1.55 (d, J=6.8 Hz, 3H), 3.24 (s, 3H), 4.18 4.49 (m, 2H), 4.63 4.80 (m, 1H), 6.00 (d, J=9.3 Hz, 1H), 7.46 (d, J=8.8 Hz, 2H), 7.72 (d, J=8.8 Hz, 2H)

Compound 5

4-Chloro-N-{(1R)-1-[4-ethyl-5-(methylsulfonyl)-4H-1,2,4-triazol-3-yl]ethyl}benzenesulfonamide (Compound 182)

[Chemical formula 40]

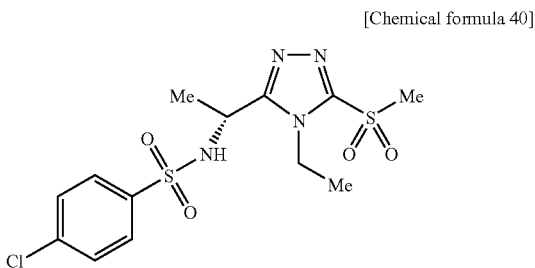

To a chloroform (30 ml) solution of 4-chloro-N-{(1R)-1-[4-ethyl-5-(methylthio)-4H-1,2,4-triazol-3-yl]ethyl}benzenesulfonamide (Compound 1) (520 mg) obtained by performing the same procedure as in Examples 1 and 2 using the corresponding raw materials, m-perchlorobenzoic acid (746 mg) was added under ice-cooling conditions, followed by stirring the mixture for 1 hour at 0° C. A saturated aqueous solution (100 ml) of sodium bicarbonate was added to the reaction mixture, and the resulting mixture was extracted with chloroform (50 ml). The organic layer was dried over anhydrous magnesium sulfate, and then the solvent was distilled off under reduced pressure. The resulting residue was purified by silica gel flash column chromatography using a solvent mixture of ethyl acetate and chloroform to obtain Compound 182 (481 mg).

$^1$H NMR (300 MHz, CDCl$_3$) δ ppm: 1.46 (t, J=7.3 Hz, 3H), 1.54 1.60 (m, 3H), 3.49 (s, 3H), 4.25 4.40 (m, 2H), 4.65 4.78 (m, 1H), 5.44 (d, J=9.8 Hz, 1H), 7.45 (d, J=8.9 Hz, 2H), 7.68 (d, J=8.9 Hz, 2H)

EXAMPLE 6

N-{(1R)-1-[5-(allylthio)-4-ethyl-4H-1,2,4-triazol-3-yl]ethyl}-4-chloro-N-methylbenzenesulfonamide (Compound 99)

[Chemical formula 41]

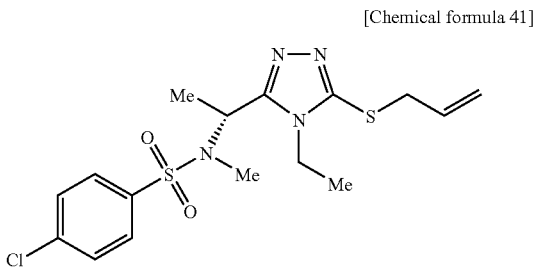

To a dimethylformamide (2 ml) solution of N-{(1R)-1-(5-allylthio)-4-ethyl-4H-1,2,4-triazol-3-yl}ethyl)-4-chlorobenzenesulfonamide (Compound 3) (200 mg) obtained by performing the same procedure as in Examples 1 and 2 using the corresponding raw materials, potassium carbonate (120 mg) and methyl iodide (0.040 ml) were added at room temperature, followed by stirring the mixture for 3 hours at room temperature. Ethyl acetate was added to the reaction mixture, and the resulting mixture was washed sequentially with a 1 mol/liter aqueous solution of hydrochloric acid and a saturated aqueous solution of sodium chloride. The organic layer was dried over anhydrous magnesium sulfate, and then the solvent was distilled off under reduced pressure. The resulting residue was eluted by silica gel flash column chromatography using a solvent mixture of ethyl acetate and hexane. Then, the eluate was recrystallized using a solvent mixture of ethyl acetate and hexane for purification, whereby Compound 98 (112 mg) was obtained.

Melting point: 142.0-143.0° C.

$^1$H NMR (200 MHz, DMSO-d$_6$) δ ppm: 1.13 (d, J=6.8 Hz, 3H), 1.27 (t, J=7.1 Hz, 3H), 2.56 (s, 3H), 3.82 (d, J=7.1 Hz, 2H), 3.90 4.25 (m, 2H), 5.04 5.27 (m, 2H), 5.43 (q, J=6.8 Hz, 1H), 5.82 6.06 (m, 1H), 7.74 (d, J=8.8 Hz, 2H), 7.90 (d, J=8.8 Hz, 2H)

EXAMPLE 7

4-Chloro-N-[(1R)-1-(4-ethyl-5-propoxy-4H-1,2,4-triazol-3-yl)ethyl]benzenesulfonamide (Compound 183)

[Chemical formula 42]

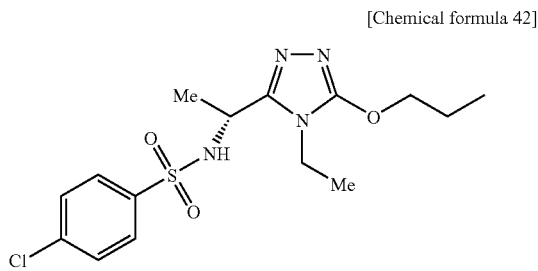

Sodium hydride (12 mg) was added, while cooled with ice, to a dimethylformamide (1.2 ml) solution of the 4-chloro-N-{(1R)-1-[4-ethyl-5-(methylsulfonyl)-4H-1,2,4-triazol-3-yl]ethyl}benzenesulfonamide (Compound 182) (47 mg) obtained in Example 5 and n-propanol (0.027 ml). The mixture was stirred for 30 minutes at room temperature, and then stirred for 2 hours at 100° C. After the reaction mixture was cooled to room temperature, it was added to a saturated aqueous solution (5 ml) of ammonium chloride. The mixture was extracted with ethyl acetate (20 ml×2) and washed with a saturated aqueous solution (20 ml) of sodium chloride. The organic layer was dried over anhydrous magnesium sulfate, and then the solvent was distilled off under reduced pressure. The resulting residue was purified by silica gel flash column chromatography using a solvent mixture of methanol and chloroform to obtain Compound 183 (35 mg).

$^1$H NMR (300 MHz, CDCl$_3$) δ ppm: 1.02 (t, J=7.5 Hz, 3H), 1.24 (t, J=7.2 Hz, 3H), 1.47 (d, J=6.8 Hz, 3H), 1.75 1.91 (m, 2H), 3.68 3.80 (m, 2H), 4.37 (t, J=6.5 Hz, 2H), 4.45 4.58 (m, 1H), 5.60 (bs, 1H), 7.45 (d, J=8.6 Hz, 2H), 7.77 (d, J=8.6 Hz, 2H)

EXAMPLE 8

(1R)-1-(4-Ethyl-5-methoxy-4H-[1,2,4]-triazol-3-yl)ethylamine (Compound 519)

[Chemical formula 43]

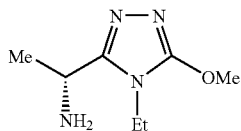

(1) Hydrazine monohydrate (30 ml) was added to a methanol (180 ml) solution of N-(t-butoxycarbonyl)-D-alanine methyl ester (41.8 g), and the mixture was stirred for 12 hours at room temperature. The reaction mixture was concentrated, and the resulting crude crystals were washed with a solvent mixture of hexane and ethyl acetate (1:1, 300 ml). Then, the washed crystals were dried to obtain (R)-(1-hydrazinocarbonyl-2-ethyl)carbamic acid t-butyl ester as a colorless powder (32.6 g).

$^1$H NMR (300 MHz, DMDO-d$_6$) δ ppm: 1.14 (d, J=7.2 Hz, 3H), 1.37 (s, 9H), 3.30-4.09 (m, 3H), 6.70-6.90 (m, 1H), 8.96 (br s, 1H)

(2) Ethyl isothiocyanate (14.6 ml) was added to an EtOH (152 ml) solution of the (R)-(1-hydrazinocarbonyl-2-ethyl)carbamic acid t-butyl ester (30.8 g) obtained in Example 8-(1), and the mixture was heated for 2 hours under reflux. After the reaction mixture was cooled to room temperature, crystals precipitated were filtered. The filtrate was concentrated, and the resulting residue was purified by silica gel chromatography using a solvent mixture of ethyl acetate and chloroform, whereby (R)-2-(N-(t-butoxycarbonyl)amino)propionyl)-N-ethylhydrazinecarbothioamide was obtained as a colorless amorphous substance (43.2 g).

$^1$H NMR (300 MHz, DMSO-d$_6$) δ ppm: 0.98-1.28 (m, 6H), 1.40 (s, 9H), 3.25-3.65 (m, 2H), 3.77-3.95 (m, 1H), 7.20-7.39 (m, 1H), 7.45-7.60 (m, 1H), 9.25 (s, 1H), 10.00 (s, 1H)

(3) An aqueous solution (218 ml) of sodium hydroxide (1 mol/liter) was added to a mixed solution, in methanol (120 ml) and dioxane (240 ml), of the (R)-2-(N-(t-butoxycarbonyl)amino)propionyl)-N-ethylhydrazinecarbothioamide (42.1 g) obtained in Example 8-(2), followed by heating the mixture for 3 hours under reflux. The reaction mixture was concentrated, and an aqueous solution (100 ml) of hydrochloric acid (2 mols/liter) was added. The mixture was extracted with an ethyl acetate-CHCl$_3$-MeOH mixed solution (10:10:1, 500 ml), and the organic layer was dried over anhydrous magnesium sulfate. Then, the solvent was distilled off under reduced pressure, and the resulting residue was washed with a solvent mixture of hexane and ethyl acetate (1:1, 300 ml), followed by drying, to obtain [(R)-1-(4-ethyl-5-mercapto-4H-[1,2,4]triazol-3-yl)ethyl]-carbamic acid t-butyl ester as a white solid (29.22 g).

$^1$H NMR (300 MHz, DMSO-d$_6$) δ ppm: 1.21 (t, J=7.1 Hz, 3H), 1.30-1.50 (m, 3H), 1.39 (s, 9H), 3.82-4.05 (m, 2H), 4.72-4.88 (m, 1H), 7.58 (d, J=8.5 Hz, 1H), 13.60 (br s, 1H)

(4) Diisopropylamine (17.4 ml) and iodomethane (7.7 ml) were added to a tetrahydrofuran (200 ml) solution of the [(R)-1-(4-ethyl-5-mercapto-4H-[1,2,4]triazol-3-yl)ethyl]-carbamic acid t-butyl ester (28.12 g) obtained in Example 8-(3). The mixture was stirred for 1 hour at room temperature, and then precipitated crystals were filtered. The filtrate was concentrated, and the resulting crude crystals were washed with a hexane-ethyl acetate solvent mixture (3:1, 200 ml), followed by drying, to obtain [(R)-1-(4-ethyl-5-methylsulfanyl-4H-[1,2,4]triazol-3-yl)ethyl]-carbamic acid t-butyl ester as a white powder (29.5 g).

$^1$H NMR (300 MHz, DMSO-d$_6$) δ ppm: 1.21 (t, J=7.0 Hz, 3H), 1.38 (s, 9H), 1.45 (t, J=7.0 Hz, 3H), 2.62 (s, 3H), 3.80-4.00 (m, 2H), 4.85-4.92 (m, 1H), 7.52 (d, J=8.5 Hz, 1H)

(5) To a chloroform (293 ml) solution of the [(R)-1-(4-ethyl-5-methylsulfanyl-4H-[1,2,4]triazol-3-yl)ethyl]-carbamic acid t-butyl ester (21.0 g) obtained in Example 8-(4), m-perchlorobenzoic acid (43.0 g) was added in four portions while being cooled with ice. The mixture was stirred for 3 hours at room temperature, and then stirred for 1 hour at 40° C. To the reaction mixture, Na$_2$S$_2$O$_3$ (12.9 g) and an aqueous solution (300 ml) of sodium hydroxide (1 mol/liter) were added. The organic layer was separated, and washed with a saturated aqueous solution of sodium chloride. The organic layer was dried over anhydrous magnesium sulfate, and then the solvent was distilled off under reduced pressure. The resulting residue was purified by silica gel flash column chromatography using a solvent mixture of hexane and ethyl acetate. Then, the purified substance was recrystallized using hexane and chloroform to obtain [(R)-1-(4-ethyl-5-methanesulfonyl-4H-[1,2,4]triazol-3-yl)ethyl]-carbamic acid t-butyl ester as a white powder (17.2 g).

$^1$H NMR (300 MHz, CDCl$_3$) δ ppm: 1.44 (s, 9H), 1.49 (t, J=7.1 Hz, 3H), 1.67 (t, J=6.8 Hz, 3H), 3.53 (s, 3H), 4.25-4.59 (m, 2H), 4.92-5.20 (m, 2H)

(6) Trifluoroacetic acid (121 ml) was added to the [(R)-1-(4-ethyl-5-methanesulfonyl-4H-[1,2,4]triazol-3-yl)ethyl]-carbamic acid t-butyl ester (100.0 g) obtained in Example 8-(5), and the mixture was stirred for 2 hours at room temperature. The reaction mixture was concentrated under reduced pressure to obtain (R)-1-(4-ethyl-5-methanesulfonyl-4H-[1,2,4]triazol-3-yl)ethylamine trifluoroacetate as a white powder (103.8 g).

$^1$H NMR (300 MHz, DMSO-d$_6$) δ ppm: 1.37 (t, J=7.2 Hz, 3H), 1.59 (t, J=6.8 Hz, 3H), 3.65 (s, 3H), 4.21-4.50 (m, 2H), 4.72-4.90 (m, 1H), 8.69 (br s, 3H)

(7) NaOMe (18 ml, 2.0N, MeOH solution) was added to the (R)-1-(4-ethyl-5-methanesulfonyl-4H-[1,2,4]triazol-3-yl)ethylamine trifluoroacetate (3.0 g) obtained in Example 8-(6), and the mixture was heated for 1 hour under reflux. The reaction mixture was cooled to room temperature, and Et$_2$O (100 ml) was added. After the mixture was cooled to 0° C., precipitated crystals were filtered. The filtrate was concentrated, and the resulting crude product was purified by NH silica gel chromatography using a solvent mixture of Et$_2$O and MeOH to obtain the captioned compound (Compound 519) as a colorless oily substance (1.55 g).

$^1$H NMR (300 MHz, CDCl$_3$) δ ppm: 1.32 (t, J=7.2 Hz, 3H), 1.54 (t, J=6.7 Hz, 3H), 3.78-3.95 (m, 2H), 4.02-4.20 (m, 1H), 4.13 (s, 3H)

EXAMPLE 9

[(1R)-1-(4-Ethyl-5-methoxy-4H-[1,2,4]triazol-3-yl)ethyl]benzenesulfonamide (Compound 376)

[Chemical formula 44]

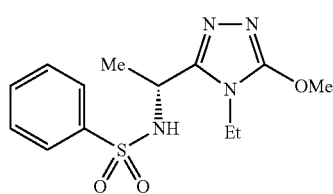

A tetrahydrofuran (0.9 ml) solution of benzenesulfonyl chloride (31 mg) was added, at room temperature, to the compound (20 mg) obtained in Example 8-(7). Then, triethylamine (0.040 ml) was added, and the mixture was stirred for 3 hours at room temperature. The reaction mixture was eluted by NH-type silica gel column chromatography using tetrahydrofuran as a solvent, and then the eluate was concentrated to obtain the captioned compound (36.5 mg).

$^1$H NMR (200 MHz, CDCl$_3$) δ ppm: 1.24 (t, J=7.1 Hz, 3H), 1.41 (t, J=7.0 Hz, 3H), 3.79 (q, J=7.1 Hz, 3H), 4.09 (s, 3H), 4.40-4.67 (m, 1H), 6.20-6.60 (m, 1H), 7.40-7.62 (m, 3H), 7.80-7.98 (m, 2H)

EXAMPLE 10

Using the same methods as the methods used in Examples 1 to 9, salts were formed, as appropriate, to obtain the compounds shown in the tables offered below. As Compounds 89, 104, 136 and 137, those purchased from Bionet were used.

The compounds obtained in the above-described Examples 1 to 9 are also shown in Table 1 along with the other compounds.

TEST EXAMPLE 1

Cell System Binding Test

Using a human Edg-1(S1P$_1$) gene transferred HEK-293 cell strain (showing a binding of Kd=6.4±2.1 nM, Bmax=160±94 fmol/10$^5$ cells to [$^3$H]-S1P), which had been obtained by a method complying with the method described in the literature (Science. 1998, 279:1552), the Edg-1(S1P$_1$) binding inhibiting effect of the compound of the present invention was investigated in accordance with the method described in the literature. Cells (1×10$^5$ cells/well) obtained as described above were seeded in poly-L-lysine-coated 96-well plates (Corning Incorporated), and then incubated in a 5% carbon dioxide gas incubator for 12 hours at 37° C. with the use of an MEM medium (Invitrogen Corporation) containing 100 U/mL of penicillin, 100 μg/mL of streptomycin, a 1% MEM nonessential amino acid solution, and 10% FCS. The cultured cells were washed twice with a buffer (20 mM Tris-HCl, pH 7.4, 100 mM NaCl, 15 mM NaF, 2 mM deoxypyridoxine, 4 mg/mL fatty acid-free BSA), and was then treated with 100 μL of the buffer incorporating [$^3$H]-S1P (produced by ARC, end concentration 10 nM) and a DMSO solution of the test compound (end concentration of the compound: 10$^{-5}$ M, end concentration of DMSO: 0.1%) for 1 hour at 4° C. After the cells were washed twice with the buffer, they were solubilized with 100 μL of Opti Phase Supermix (produced by Perkin-Elmer), and measured for radioactivity by means of Micro Beta (produced by Perkin-Elmer). Based on the radioactivity, the amount (A) of binding of [$^3$H]-S1P upon the addition of the compound was calculated.

The same procedure was performed in the absence of the test compound, and the amount (B) of binding of [$^3$H]-S1P was calculated. Moreover, the same procedure was performed in the absence of the test compound with the use of HEK-293 cells, to which the Edg-1(S1P$_1$) gene had not been transferred, and the background amount (C) of binding of [$^3$H]-S1P was calculated.

The Edg-1(S1P$_1$) binding inhibition rate of the compound, calculated from the following equation, is shown in Table 1.

$$\text{Inhibition rate}(\%)=[1-(A-C)/(B-C)]\times 100$$

TEST EXAMPLE 2

Membrane System Binding Test

Using a human Edg-1(S1P$_1$) gene transferred HEK-293 cell strain membrane fraction, the Edg-1(S1P$_1$) binding inhibiting effect of the compound of the present invention was investigated in accordance with the method described in the literature (Science. 2002, 296:346) (showing a binding of Kd=0.15 nM, Bmax=2.5 fmol/μg to [$^{33}$P]-S1P). The membrane fraction was obtained by treating the cells with a solubilizing buffer (1 mM Tris/HCl, pH 7.2) for 10 minutes on ice, centrifuging the system (1000×g, 5 min) to remove insoluble fractions, and then centrifuging the system (40000×g, 30 min, 4° C.). The resulting membrane fraction was dissolved in a binding buffer (20 mM Tris-HCl, pH 7.4, 100 mM NaCl, 15 mM NaF, 2 mM deoxypyridoxine, 4 mg/mL fatty acid-free BSA), and then [$^{33}$P]-S1P (produced by ARC, end concentration 0.1 nM) and a DMSO solution of the test compound (end concentration of the compound: 10$^{-5}$ M, end concentration of DMSO: 0.1%) were added, followed by stirring the mixture and subsequently treating it for 1 hour at 30° C. Using a harvester, the membrane fraction was harvested onto unifilter-96GF/C filter (produced by Perkin-Elmer). Then, the filter with the membrane fraction was washed 4 times with the binding buffer, and the filter was dried. To the filter, 25 μL Microscint 0 (produced by Perkin-Elmer) was added, and the assay system was measured for radioactivity by means of Top Count NXT (Packard). Based on the radioactivity, the amount (A) of binding of [$^{33}$P]-S1P to the membrane fraction upon addition of the compound was calculated.

The same procedure was performed in the absence of the test compound, and the amount (B) of binding of [$^{33}$P]-S1P was calculated. Moreover, the same procedure was performed in the absence of the test compound with the use of HEK-293 cells, to which the Edg-1(S1P$_1$) gene had not been transferred, and the background amount (C) of binding of [$^{33}$P]-S1P was calculated.

The Edg-1(S1P$_1$) binding inhibition rate of the compound, calculated from the following equation, is shown in

TABLE 1

Inhibition rate (%) = [1 − (A − C) / (B − C)] × 100

| Compound No. | CHEMISTRY | Melting point (°C.) | ¹H NMR |
|---|---|---|---|
| Compound 1 | (4-chlorophenyl)sulfonamide linked to (S)-1-(4-ethyl-5-(methylthio)-4H-1,2,4-triazol-3-yl)ethyl | 176.0-177.0 | |
| Compound 2 | (4-chlorophenyl)sulfonamide linked to (S)-1-(4-ethyl-5-(propylthio)-4H-1,2,4-triazol-3-yl)ethyl | 129.5-130.5 | |
| Compound 3 | (4-chlorophenyl)sulfonamide linked to (S)-1-(5-(allylthio)-4-ethyl-4H-1,2,4-triazol-3-yl)ethyl | 110.0-113.0 | |
| Compound 4 | (4-chlorophenyl)sulfonamide linked to (S)-1-(4-ethyl-5-(prop-2-yn-1-ylthio)-4H-1,2,4-triazol-3-yl)ethyl | 116.0-117.0 | |
| Compound 5 | (4-chlorophenyl)sulfonamide linked to 1-(5-(benzylthio)-4-ethyl-4H-1,2,4-triazol-3-yl)ethyl | | (200 MHz, DMSO-d6) δ ppm: 1.10 (t, J = 7.1 Hz., 3H), 1.25 (d, J = 6.8 Hz, 3H), 3.62-3.96 (m, 2H), 4.36 (s, 2H), 4.55-4.78 (m. 1H), 7.15-7.47 (m, 5H), 7.64 (d, J = 8.6 Hz, 2H), 7.77 (d, J = 8.6 Hz, 2H), 8.02 (d, J = 8.6 Hz, 1H) |
| Compound 6 | (4-chlorophenyl)sulfonamide linked to 1-(5-([1,1'-biphenyl]-4-ylmethylthio)-4-ethyl-4H-1,2,4-triazol-3-yl)ethyl | | |

TABLE 1-continued
Compound 7 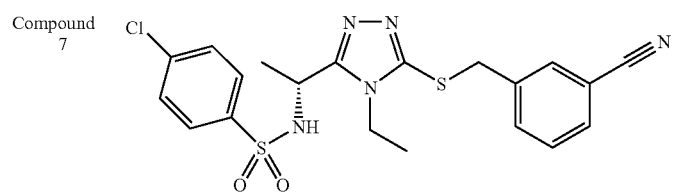
Compound 8 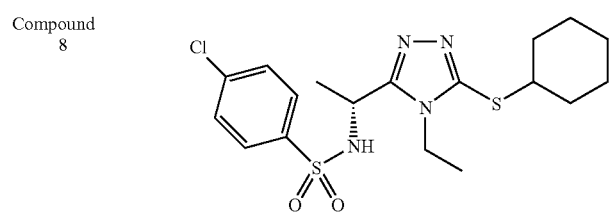
Compound 9 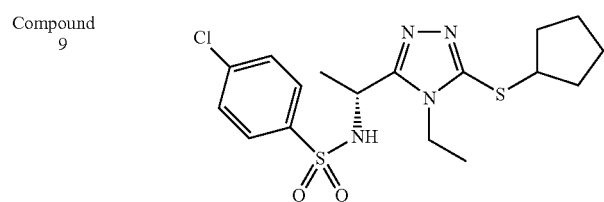
Compound 10 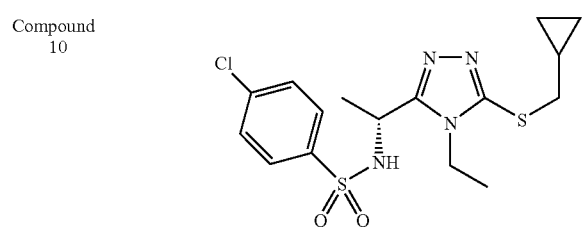
Compound 11 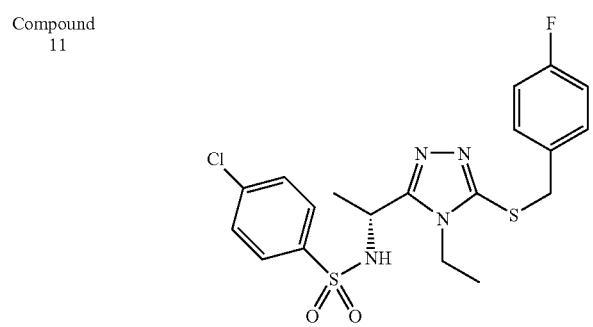
Compound 12 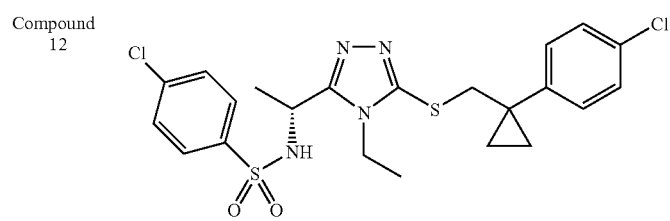
Compound 13 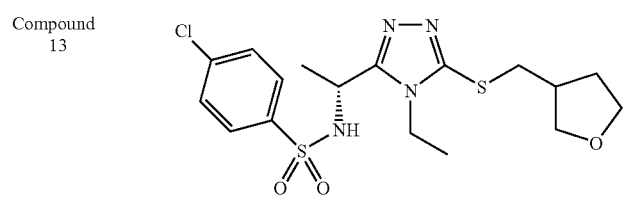

TABLE 1-continued
Compound 14
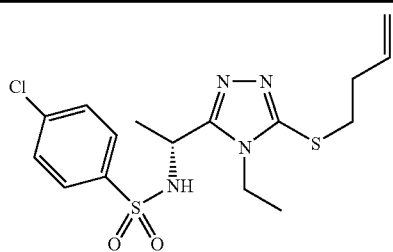
Compound 15
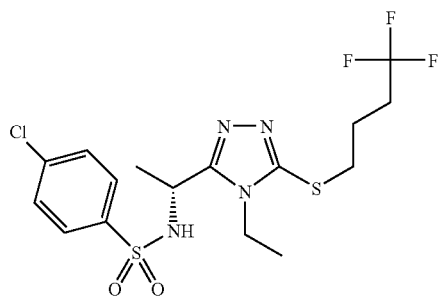
Compound 16
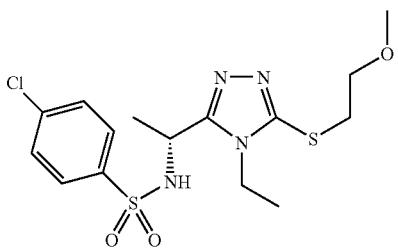
Compound 17
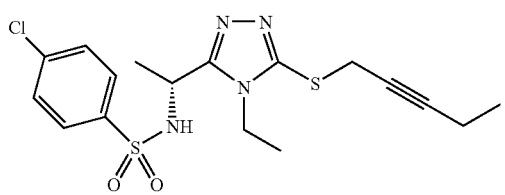
Compound 18
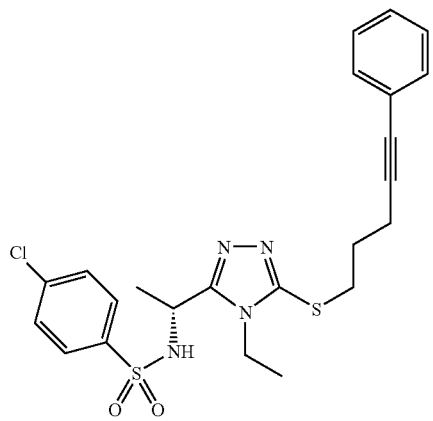
Compound 19
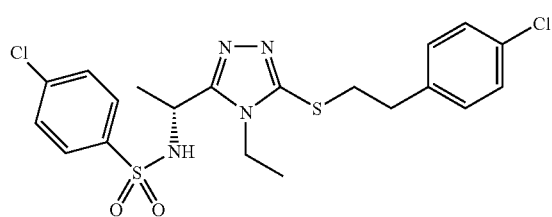

TABLE 1-continued
Compound 20
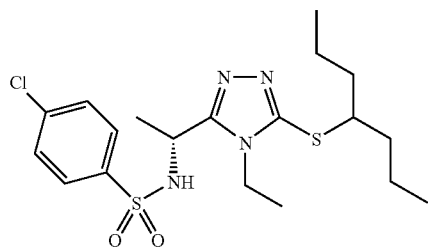
Compound 21
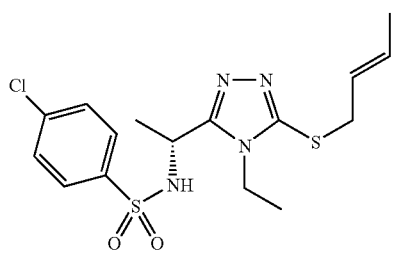
Compound 22
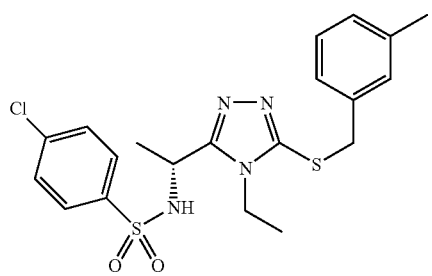
Compound 23
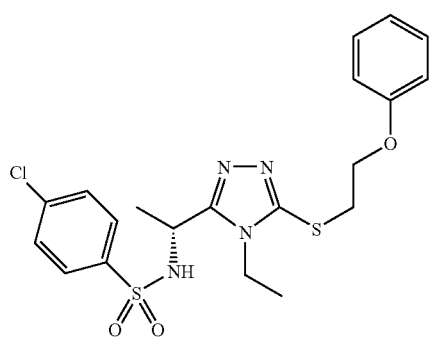
Compound 24
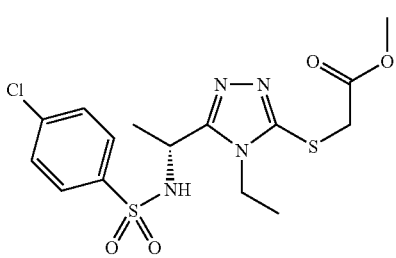

TABLE 1-continued
Compound 25
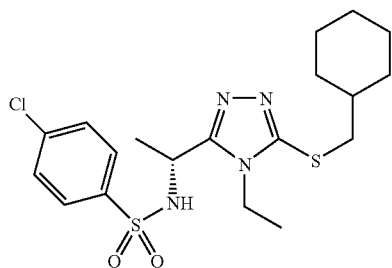
Compound 26
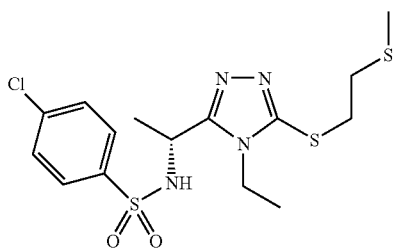
Compound 27
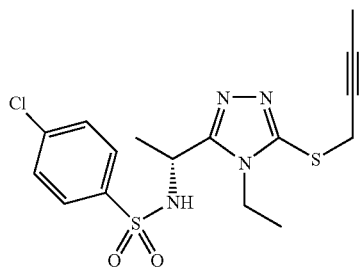
Compound 28
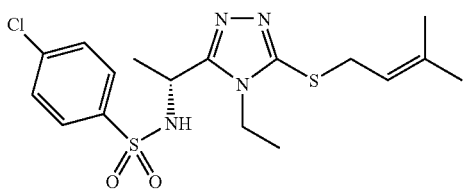
Compound 29
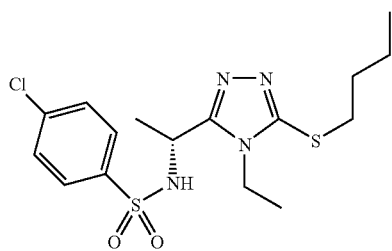
Compound 30
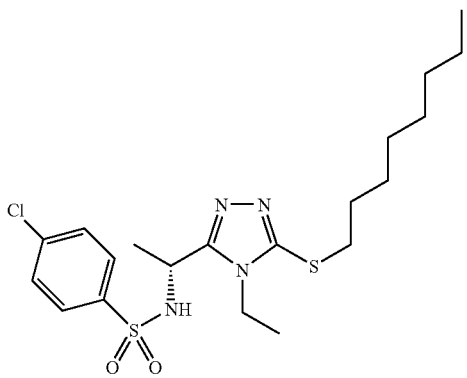

TABLE 1-continued
Compound 31
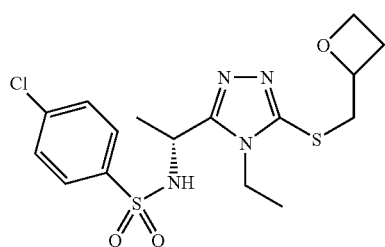
Compound 32
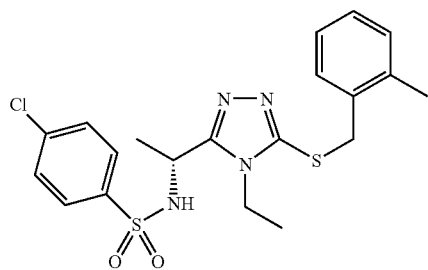
Compound 33
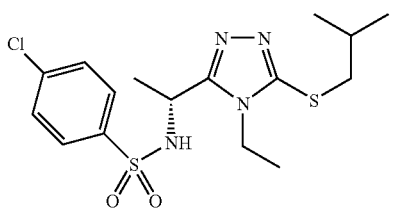
Compound 34
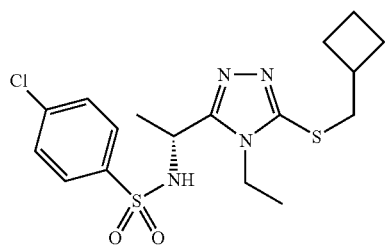
Compound 35
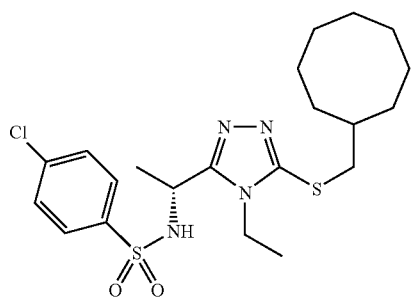
Compound 36
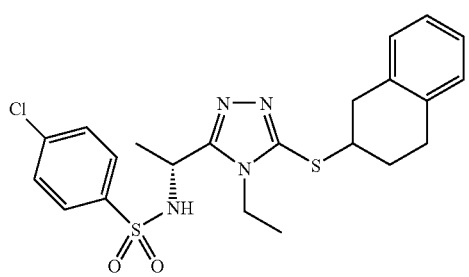

TABLE 1-continued
Compound 37
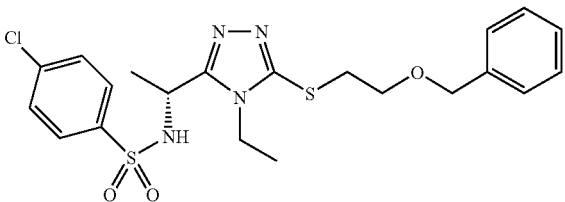
Compound 38
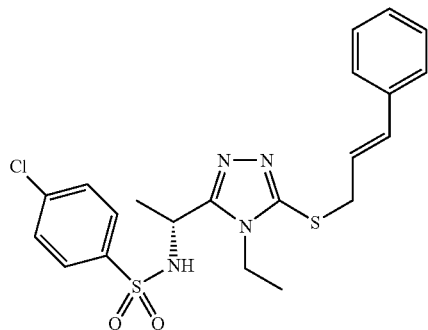
Compound 39
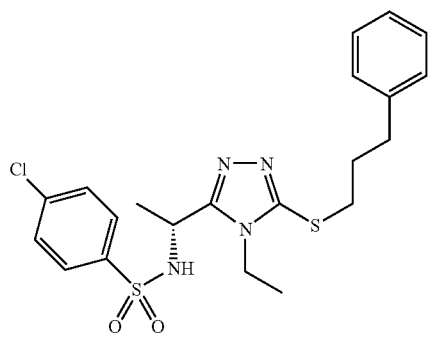
Compound 40
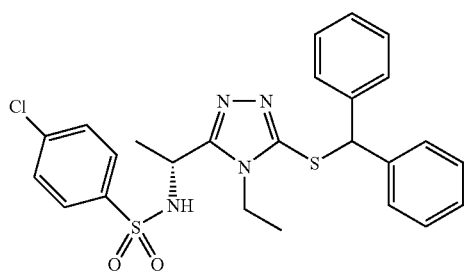
Compound 41
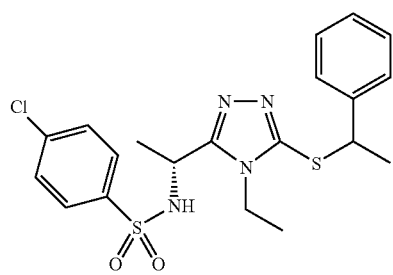

TABLE 1-continued
Compound 42
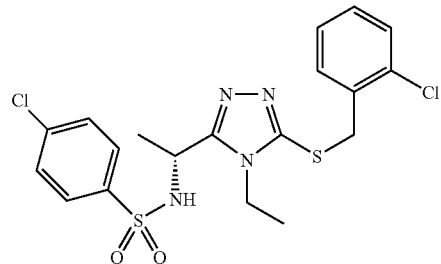
Compound 43
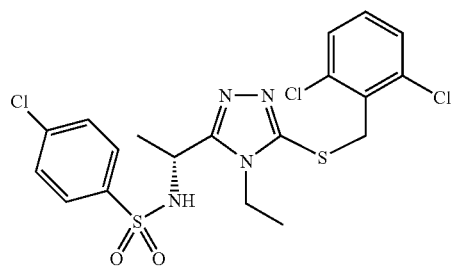
Compound 44
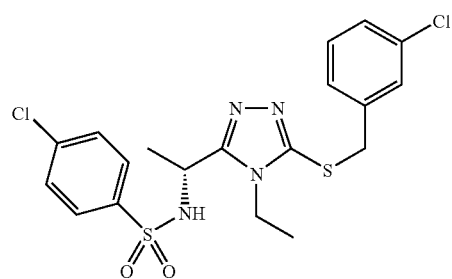
Compound 45
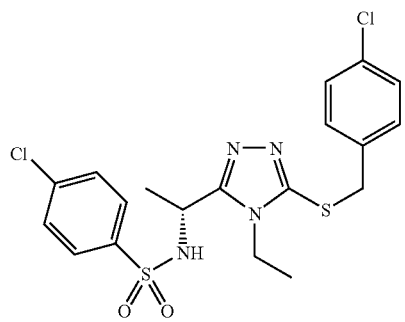
Compound 46
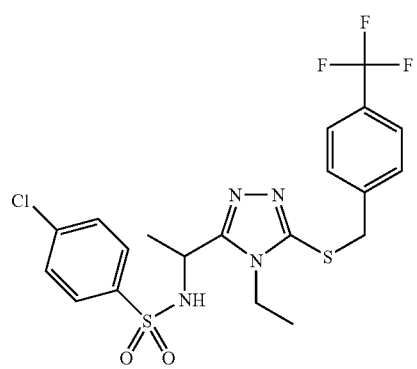

TABLE 1-continued
| Compound 47 | 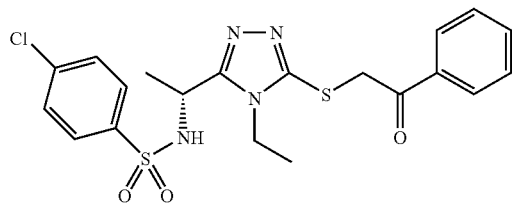 |
| Compound 48 | 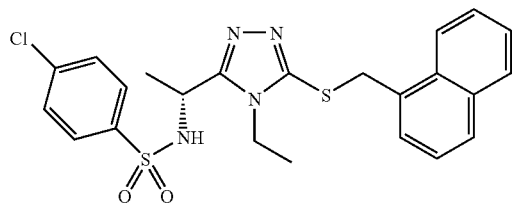 |
| Compound 49 | 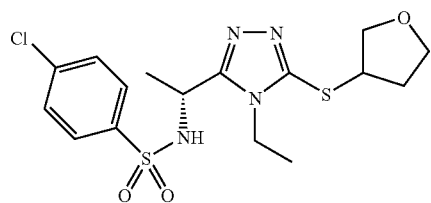 |
| Compound 50 | 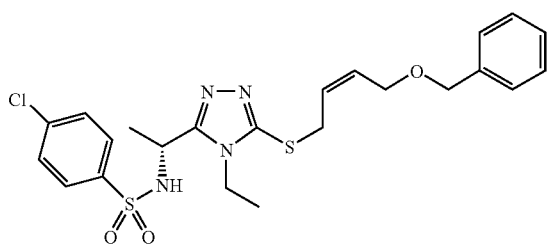 |
| Compound 51 | 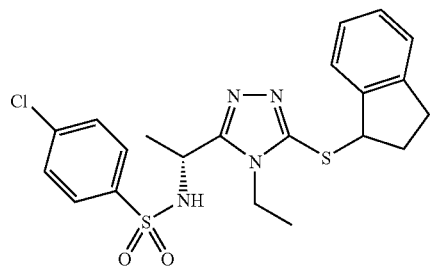 |
| Compound 52 | 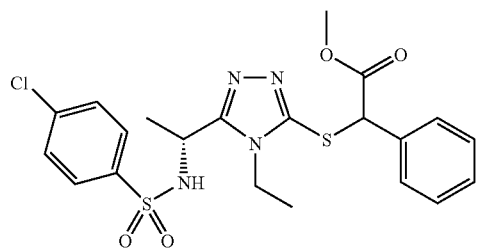 |
| Compound 53 | 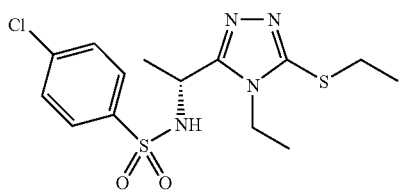 |

TABLE 1-continued
Compound 54
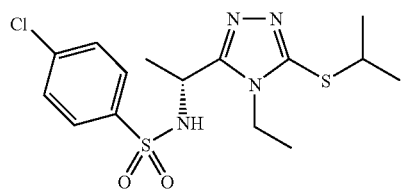
Compound 55
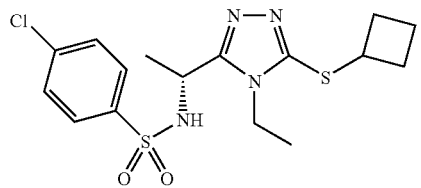
Compound 56
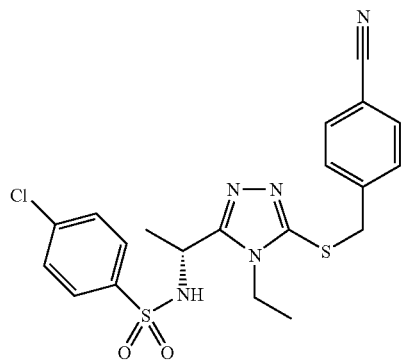
Compound 57
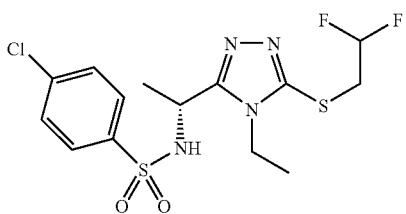
Compound 58
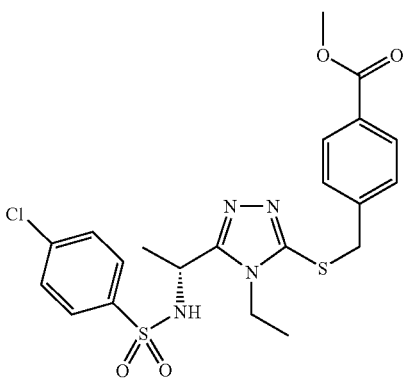

TABLE 1-continued

Compound 59

Compound 60

Compound 61

Compound 62

Compound 63

Compound 64

Compound 65

TABLE 1-continued
Compound 66
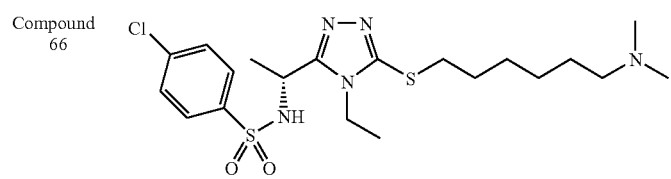
Compound 67
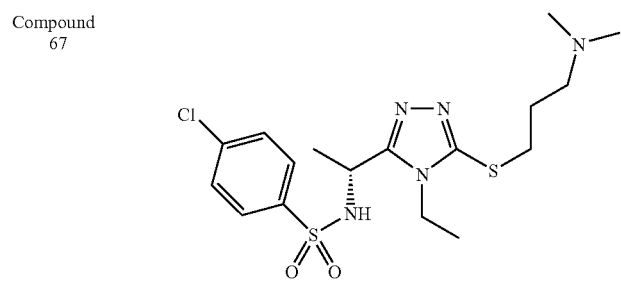
Compound 68
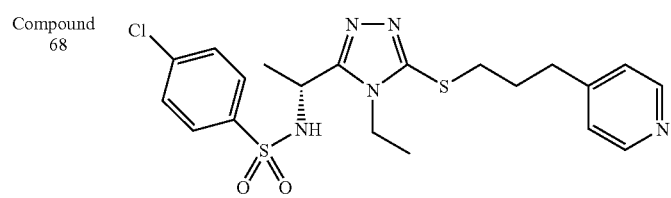
Compound 69
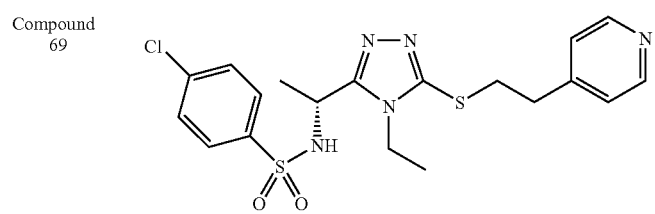
Compound 70
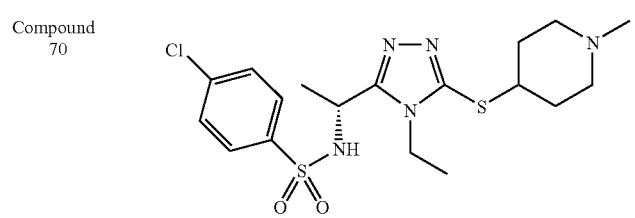
Compound 71
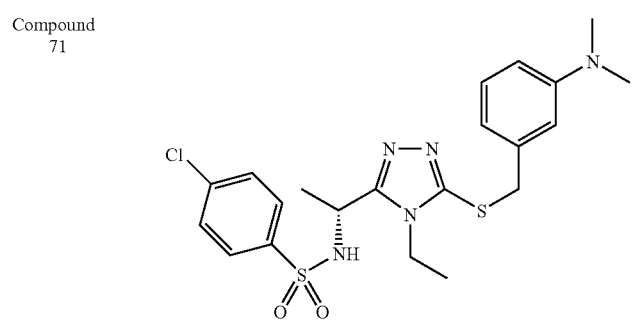
Compound 72
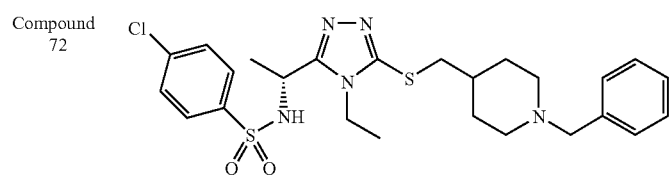

TABLE 1-continued
Compound 73
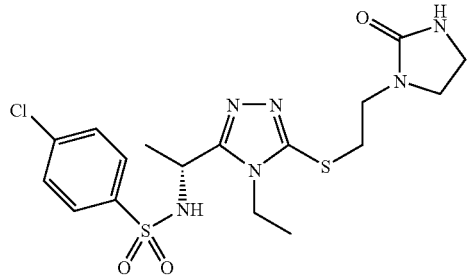
Compound 74
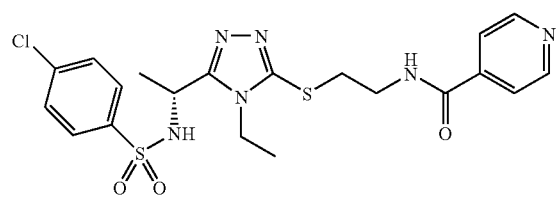
Compound 75
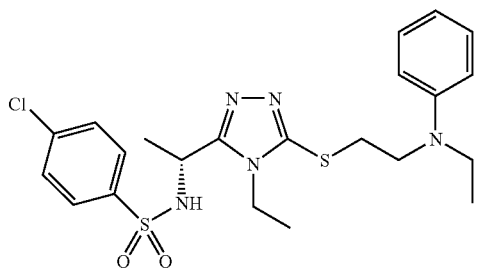
Compound 76
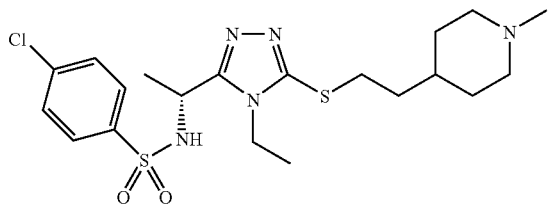
Compound 77
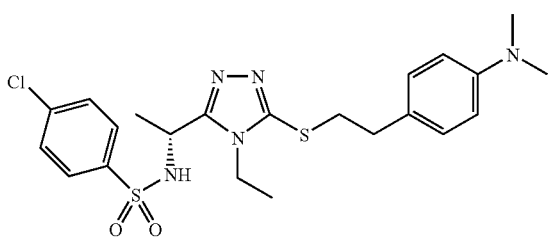
Compound 78
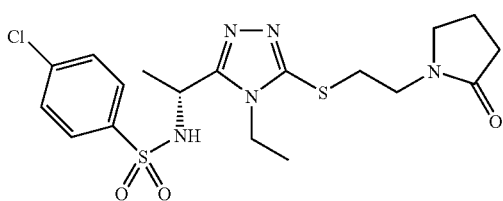

| | |
|---|---|
| Compound 79 | 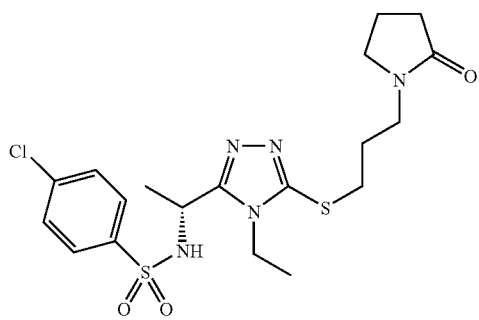 |
| Compound 80 | 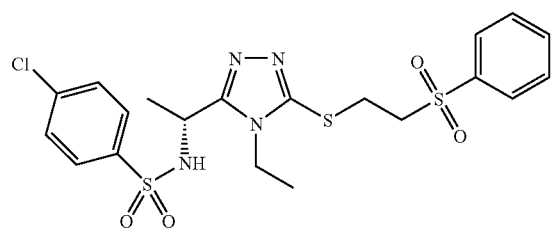 |
| Compound 81 | 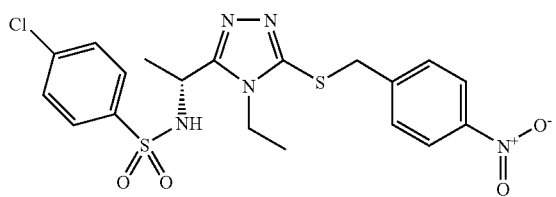 |
| Compound 82 | 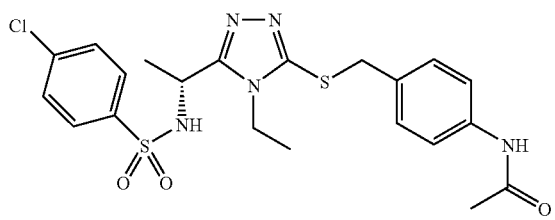 |
| Compound 83 | 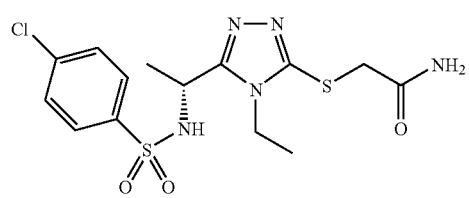 |
| Compound 84 | 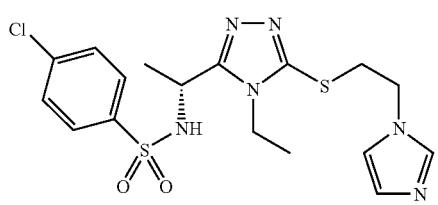 |
| Compound 85 | 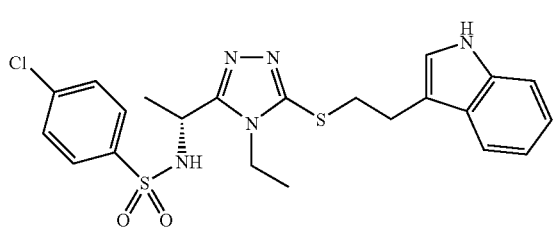 |

| | | | |
|---|---|---|---|
| Compound 86 | | | |
| Compound 87 | | | |
| Compound 88 | | | |
| Compound 89 | | | |
| Compound 90 | | | 169.5-172.5 |
| Compound 91 | | | 164.5-165.0 |
| Compound 92 | | | 128.5-130.0 |
| Compound 93 | | | (300 MHz, DMSO-d6) δ ppm: 1.23 (d, J = 6.8 Hz, 3H), 3.37 (s, 3H), 4.55-4.69 (m, 1H), 7.66 (d, J = 8.8 Hz, 2H), 7.77 (d, J = 8.8 Hz, 2H), 8.53 (d, J = 7.9 Hz, 1H), 13.61 (s, 1H) |

TABLE 1-continued
| | Structure | mp (°C) | NMR |
|---|---|---|---|
| Compound 94 | 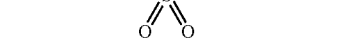 | | |
| Compound 95 | 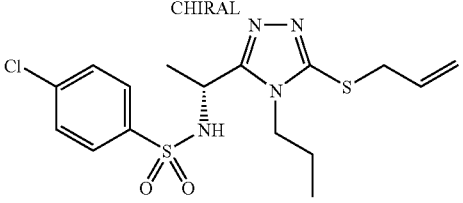 | 117.5-118.0 | |
| Compound 96 | 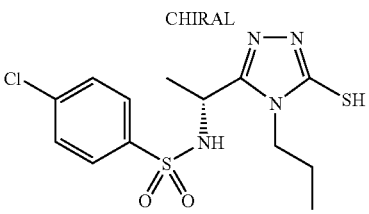 | | (300 MHz, DMSO-d6) δ ppm: 0.88 (t, J = 7.4 Hz, 3H), 1.18 (d, J = 6.7 Hz, 3H), 1.54-1.84 (m, 2H), 3.72-3.99 (m, 2H), 4.56-4.70 (m, 1H), 7.68 (d, J = 8.7 Hz, 2H), 7.80 (d, J = 8.7 Hz, 2H), 8.57 (d, J = 8.7 Hz, 1H), 13.63 (s, 1H) |
| Compound 97 | 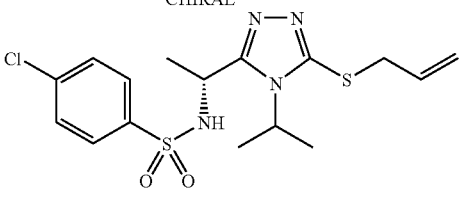 | 172.5-173.45 | |
| Compound 98 | 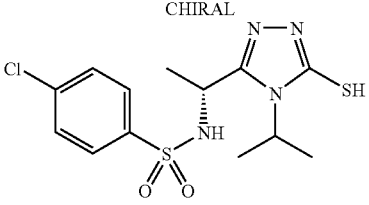 | | (300 MHz, CDCl3) δ ppm: 1.49 (d, J = 6.8 Hz, 3H), 1.56-1.69 (m, 6H), 4.75-5.05 (m, 2H), 6.57-6.67 (m, 1H), 7.48 (d, J = 8.6 Hz, 2H), 7.77 (d, J = 8.8 Hz, 2H), 11.74 (bs, 1H) |
| Compound 99 | 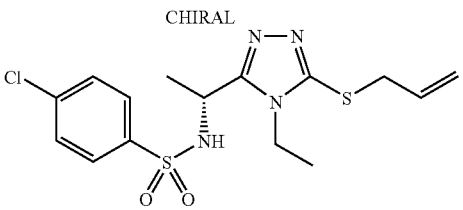 | 142.0-143.0 | |
| Compound 100 | 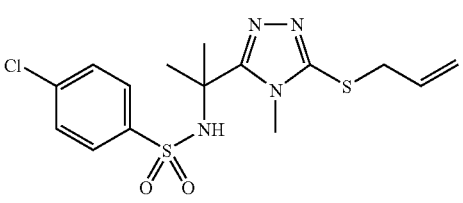 | 221.0-222.0 | |

TABLE 1-continued

| Compound | Structure | mp (°C) | NMR |
|---|---|---|---|
| Compound 101 | (4-chlorophenyl)sulfonamide-C(CH3)2-(4-methyl-5-mercapto-1,2,4-triazol-3-yl) | | (300 MHz, DMSO-d6) δ ppm: 1.45 (s, 6H), 3.50 (s, 3H) 7.62 (d, J = 8.9 Hz, 2H), 7.70 (d, J = 8.9 Hz, 2H), 8.66 (s, 1H), 13.59 (s, 1H) |
| Compound 102 | (4-chlorophenyl)sulfonamide-CH2-(4-methyl-5-allylthio-1,2,4-triazol-3-yl) | 115.5–116.0 | |
| Compound 103 | (4-chlorophenyl)sulfonamide-CH2-(4-methyl-5-mercapto-1,2,4-triazol-3-yl) | | (300 MHz, DMSO-d6) δ ppm: 3.36 (s, 3H), 4.13 (s, 2H) 7.66 (d, J = 8.9 Hz, 2H), 7.76 (d, J = 8.9 Hz, 2H), 8.53 (bs, 1H), 13.58 (s, 1H) |
| Compound 104 | (4-chlorophenyl)sulfonamide-CH2-(4-ethyl-5-allylthio-1,2,4-triazol-3-yl) | | |
| Compound 105 | (4-chlorophenyl)sulfonamide-CH(Et)-(4-methyl-5-allylthio-1,2,4-triazol-3-yl) | 155.5–157.5 | |
| Compound 106 | CHIRAL (4-chlorophenyl)sulfonamide-CH(Et)-(4-methyl-5-allylthio-1,2,4-triazol-3-yl) | 144.5–145.5 | |
| Compound 107 | (4-chlorophenyl)sulfonamide-CH(Et)-(4-methyl-5-mercapto-1,2,4-triazol-3-yl) | | (300 MHz, DMSO-d6) δ ppm: 0.75 (t, J = 7.3 Hz, 3H), 1.59-1.86 (m, 2H), 3.26 ? 3.40 (m, 3H), 4.27-4.39 (m, 1H), 7.60 (d, J = 8.0 Hz, 2H), 7.70 (d, J = 8.9 Hz, 2H), 8.65 (bs, 1H), 13.58 (bs, 1H) |
| Compound 108 | CHIRAL (4-chlorophenyl)sulfonamide-CH(Et)-(4-methyl-5-mercapto-1,2,4-triazol-3-yl) | | (300 MHz, CDCl3) δ ppm: 0.90 (t, J = 7.3 Hz, 3H), 1.76-1.98 (m, 2H), 3.58 (s, 3H), 4.40-4.49 (m, 1H), 6.75 (bs, 1H), 7.44-7.50 (m, 2H), 7.68-7.76 (m, 2H), 11.89 (bs, 1H) |

TABLE 1-continued

| Compound 109 | (structure) | 155.5-156.5 | |
|---|---|---|---|
| Compound 110 | (structure) | | |
| Compound 111 | (structure) | | (300 MHz, DMSO-d6) δ ppm: 0.74 (t, J = 7.3 Hz, 3H), 1.18 (t, J = 7.2 Hz, 3H), 1.56-1.84 (m, 2H), 3.78 ? 4.08 (m, 2H), 4.26-4.40 (m, 1H), 7.62 (d, J = 8.9 Hz, 2H), 7.71 (d, J = 8.9 Hz, 2H), 8.60-8.72 (m, 1H), 13.59 (s, 1H) |
| Compound 112 | CHIRAL (structure) | | |
| Compound 113 | (structure) | 141.5-142.0 | |
| Compound 114 | (structure) | | (300 MHz, DMSO-d6) δ ppm: 0.74 (t, J = 7.3 Hz, 3H), 0.83 (t, J = 7.4 Hz, 3H), 1.46-1.92 (m, 4H), 3.68-3.85 (m, 2H), 4.30-4.47 (m, 1H), 5.03-5.30 (m, 2H), 5.81-6.00 (m, 1H), 7.48-7.72 (m, 4H), 8.63 (d, J = 8.2 Hz, 1H) |
| Compound 115 | (structure) | | (300 MHz, DMSO-d6) δ ppm: 0.75 (t, J = 7.3 Hz, 3H), 0.86 (t, J = 7.4 Hz, 3H), 1.52-1.84 (m, 4H), 3.66 ? 3.94 (m, 2H), 4.26-4.37 (m, 1H), 7.62 (d, J = 8.9 Hz, 2H), 7.71 (d, J = 8.9 Hz, 2H), 8.66 (d, J = 7.9 Hz, 1H), 13.60 (s, 1H) |
| Compound 116 | (structure) | | (300 MHz, CDCl3) δ ppm: 0.92 (t, J = 7.3 Hz, 3H), 1.02 (t, J = 7.4 Hz, 3H), 1.75-1.91 (m, 4H), 8.93-4.09 (m, 2H), 4.40-4.50 (m, 1H), 7.20 (br, 1H), 7.41-7.52 (m, 2H), 7.70-7.77 (m, 2H), 12.14 (bs, 1H) |

TABLE 1-continued

| Compound 117 | [structure: 4-Cl-C6H4-SO2-NH-CH(Et)-triazole(N-iPr)-S-allyl, CHIRAL] | 161.5-164.0 | |
|---|---|---|---|
| Compound 118 | [structure: 4-Cl-C6H4-SO2-NH-CH(Et)-triazole(N-iPr)-SH, CHIRAL] | | (300 MHz, CDCl3) δ ppm: 0.96 (t, J = 7.3 Hz, 3H), 1.55-1.68 (m, 6H), 1.74-1.90 (m, 2H), 4.54-4.64 (m, 1H), 4.92 (bs, 1H), 6.79 (bs, 1H), 7.42-7.51 (m, 2H), 7.70-7.77 (m, 2H), 11.74 (bs, 1H) |
| Compound 119 | [structure: 4-Cl-C6H4-SO2-NH-CH(Et)-triazole(N-cyclopentyl)-S-allyl] | 163.0-164.0 | |
| Compound 120 | [structure: 4-Cl-C6H4-SO2-NH-CH(Et)-triazole(N-cyclopentyl)-SH] | | (300 MHz, DMSO-d6) δ ppm: 0.74 (t, J = 7.3 Hz, 3H), 1.44-1.98 (m, 10H), 4.36-4.51 (m, 1H), 4.63-4.74 (m, 1H), 7.60-7.65 (m, 2H), 7.69-7.75 (m, 2H), 8.50-8.74 (m, 1H), 13.52 (bs, 1H) |
| Compound 121 | [structure: 4-Cl-C6H4-SO2-NH-CH(Et)-triazole(N-benzyl)-S-allyl] | 172.0-173.0 | |
| Compound 122 | [structure: 4-Cl-C6H4-SO2-NH-CH(Et)-triazole(N-benzyl)-SH] | | (300 MHz, DMSO-d6) δ ppm: 0.43 (t, J = 7.3 Hz, 3H), 1.32-1.54 (m, 2H), 3.97-4.16 (m, 1H), 5.04 (d, J = 16.1 Hz, 1H), 5.84 (d, J = 16.1 Hz, 1H), 7.09-7.45 (m, 5H), 7.47-7.66 (m, 4H), 8.70 (d, J = 7.9 Hz, 1H), 13.78 (s, 1H) |
| Compound 123 | [structure: 4-Cl-C6H4-SO2-NH-CH(Et)-triazole(N-cyclohexyl)-S-allyl] | 172.5-173.5 | |

TABLE 1-continued

| | | | |
|---|---|---|---|
| Compound 124 | | | (300 MHz, DMSO-d6) δ ppm: 0.74 (t, J = 7.2 Hz, 3H), 1.04-1.88 (m, 12H) 4.32-4.52 (m, 1H) 7.48-7.93 (m, 4H) 8.62 (d, J = 7.6 Hz, 1H) 13.56 (bs, 1H) |
| Compound 125 | | 161.5-162.0 | (300 MHz, CDCl3) δ ppm: 0.86 (t, J = 7.3 Hz, 3H), 1.15-1.35 (m, 2H), 1.65-1.96 (m, 2H), 3.39 (s, 3H), 3.73-3.80 (m, 2H), 4.87-4.49 (m, 1H), 5.07-5.27 (m, 2H), 5.85-6.01 (m, 2H), 7.40 (d, J = 8.9 Hz, 2H), 7.70 (d, J = 8.9 Hz, 2H) |
| Compound 126 | | 166.0-164.0 | |
| Compound 127 | | 155.0-156.0 | |
| Compound 128 | | | (300 MHz, CDCl3) δ ppm: 0.89 (t, J = 7.3 Hz, 3H), 1.20-1.95 (m, 4H), 3.58 (s, 3H), 4.44-4.57 (m, 1H), 6.59-6.76 (m, 1H), 7.45 (d, J = 8.5 Hz, 2H), 7.69 (d, J = 8.5 Hz, 2H), 11.41 (s, 1H) |
| Compound 129 | | 150.5-151.5 | |
| Compound 130 | | | (200 MHz, CDCl3) δ ppm: 0.89 (d, J = 6.8 Hz, 3H), 1.03 (d, J = 6.6 Hz, 3H), 2.18-2.46 (m, 1H), 3.61 (s, 3H), 4.04-4.30 (m, 1H), 7.30-7.74 (m, 5H), 12.23 (bs, 1H) |

TABLE 1-continued

| Compound 131 | | 171.5-173.5 | |
| --- | --- | --- | --- |
| Compound 132 | | | (300 MHz, DMSO-d6) δ ppm: 3.38 (s, 3H), 5.83 (bs, 1H), 7.14-7.25 (m, 5H), 7.39-7.46 (m, 2H), 7.52-7.59 (m, 2H), 9.14 (bs, 1H), 13.66 (bs, 1H) |
| Compound 133 | | 126.0-128.0 | CHIRAL |
| Compound 134 | | 122.5-125.0 | CHIRAL |
| Compound 135 | | 172.0-174.0 | |
| Compound 136 | | | |
| Compound 137 | | | |

| | | |
|---|---|---|
| Compound 138 | (structure: 4-chlorophenylsulfonamide of chiral 1-(4-ethyl-5-(allylthio)-4H-1,2,4-triazol-3-yl)-2-phenylethylamine) | 109.0-110.0 |
| Compound 139 | (structure: 4-chlorophenylsulfonamide of chiral 1-(4-ethyl-5-(propylthio)-4H-1,2,4-triazol-3-yl)-2-phenylethylamine) | 138.5-139.5 |
| Compound 140 | (structure: 4-chlorophenylsulfonamide of chiral 1-(4-ethyl-5-mercapto-4H-1,2,4-triazol-3-yl)-2-phenylethylamine) | (300 MHz, CDCl3) δ ppm: 1.12 (t, J = 7.2 Hz, 3H), 3.10-3.24 (m, 2H), 3.70-3.82 (m, 1H), 3.89-4.01 (m, 1H), 4.69-4.72 (m, 1H), 6.62 (bs, 1H), 6.97-7.03 (m, 2H), 7.19-7.25 (m, 3H), 7.38-7.48 (m, 2H), 7.57-7.68 (m, 2H), 11.40 (bs, 1H) |
| Compound 141 | (structure: 4-chlorophenylsulfonamide of chiral 1-(4-propyl-5-(allylthio)-4H-1,2,4-triazol-3-yl)-2-phenylethylamine) | |
| Compound 142 | (structure: 4-chlorophenylsulfonamide of chiral 1-(4-propyl-5-mercapto-4H-1,2,4-triazol-3-yl)-2-phenylethylamine) | |
| Compound 143 | (structure: 4-chlorophenylsulfonamide of chiral 1-(4-isopropyl-5-(allylthio)-4H-1,2,4-triazol-3-yl)-2-phenylethylamine) | |

TABLE 1-continued
| Compound 144 | 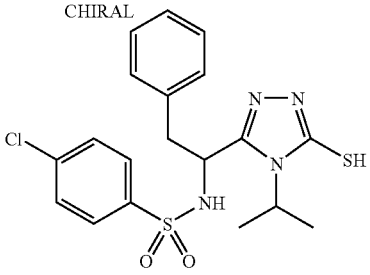 | (300 MHz, CDCl3) δ ppm: 1.37-1.56 (m, 6H), 2.94-3.24 (m, 2H), 4.74-4.89 (m, 2H), 6.10-6.45 (m, 1H), 6.96-7.06 (m, 2H), 7.12-7.28 (m, 3H), 7.29-7.43 (m, 2H), 7.54-7.65 (m, 2H), 11.00-11.45 (m, 1H) |
| --- | --- | --- |
| Compound 145 | 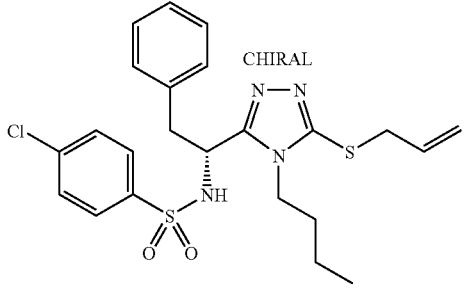 | 112.0-112.5 |
| Compound 146 | 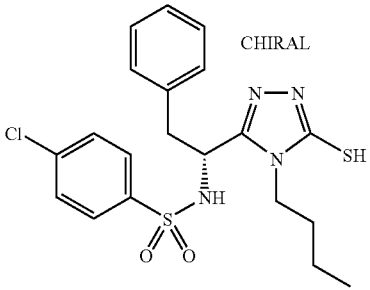 | (300 MHz, CDCl3) δ ppm: 0.92 (t, J = 7.1 Hz, 3H), 1.18-1.43 (m, 2H), 1.45-1.91 (m, 2H), 3.10-3.30 (m, 2H), 3.59-4.01 (m, 2H), 4.57-4.80 (m, 1H), 6.93-7.65 (m, 10H), 12.11 (bs, 1H) |
| Compound 147 | 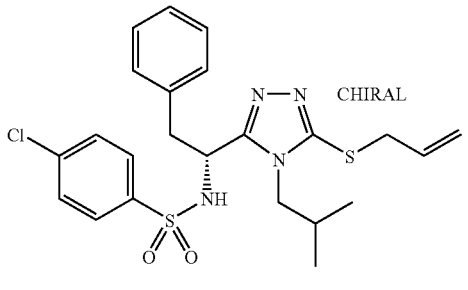 | 117.0-117.5 |
| Compound 148 | 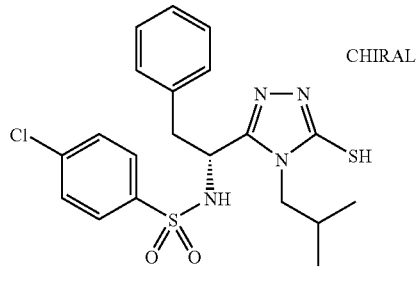 | |

TABLE 1-continued
| Compound 149 | 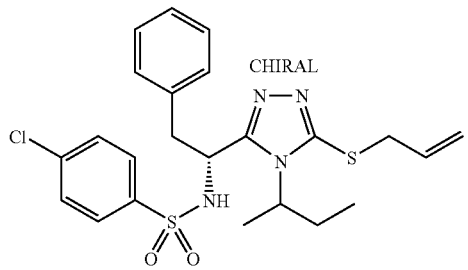 | |
| --- | --- | --- |
| Compound 150 | 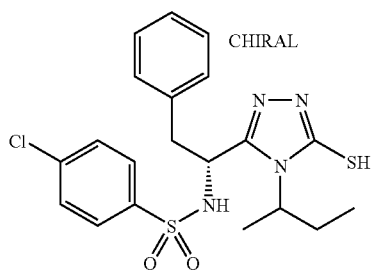 | (300 MHz, CDCl3) δ ppm: 0.60-1.00 (m, 3H), 1.15-2.40 (m, 5H), 3.00-3.30 (m, 2H), 4.81-4.94 (m, 1H), 6.95-7.63 (m, 10H), 11.98 (bs, 1H) |
| Compound 151 | 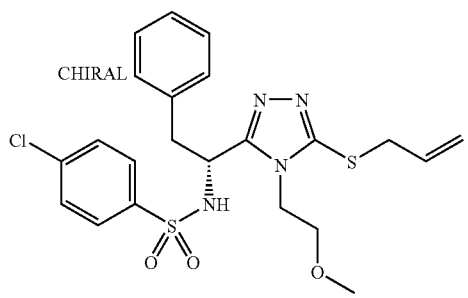 | |
| Compound 152 | 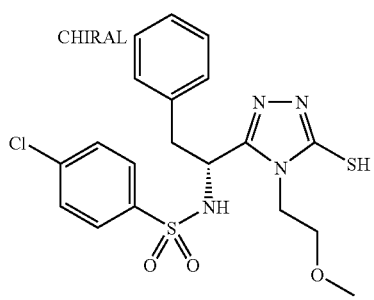 | (300 MHz, DMSO-d6) δ ppm: 2.84-3.17 (m, 2H), 3.14 (s, 3H), 3.28-3.56 (m, 2H), 3.86-4.19 (m, 2H), 4.65-4.77 (m, 1H), 7.04-7.28 (m, 5H), 7.43-7.50 (m, 4H), 8.85 (bs, 1H), 13.69 (bs, 1H) |
| Compound 153 | 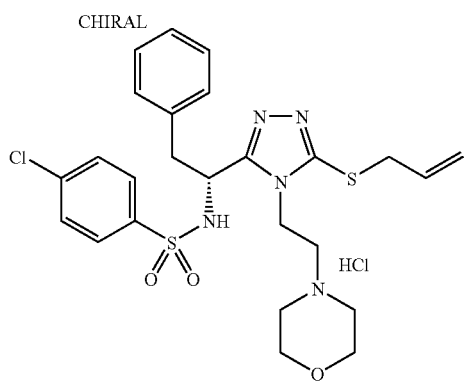 | (300 MHz, DMSO-d6) δ ppm: 2.81-4.49 (m, 16H), 4.60-4.85 (m, 1H), 4.93-5.27 (m, 2H), 5.78-6.01 (m, 1H), 7.03-7.27 (m, 5H), 7.42-7.58 (m, 2H), 7.58-7.77 (m, 2H), 8.97 (d, J = 8.2 Hz, 1H), 11.85 (bs, 1H) |

TABLE 1-continued
| Compound 154 | 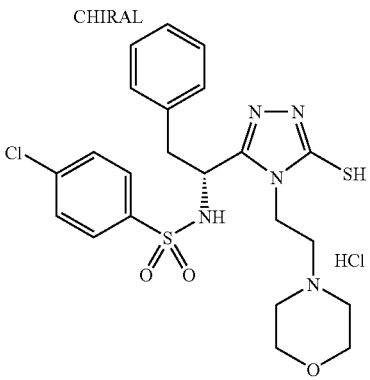 | (300 MHz, CDCl3) δ ppm: 2.77-3.34 (m, 4H), 3.52-3.92 (m, 4H), 3.90-4.42 (m, 4H), 4.62-4.87 (m, 2H), 5.04-5.35 (m, 1H), 6.91-7.25 (m, 7H), 7.40-7.54 (m, 2H), 8.71 (d, J = 6.2 Hz, 1H), 11.30 (bs, 1H), 12.69 (bs, 1H) |
| --- | --- | --- |
| Compound 155 | 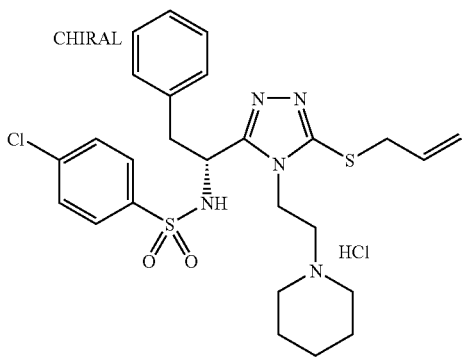 | 186.5-187.5 |
| Compound 156 | 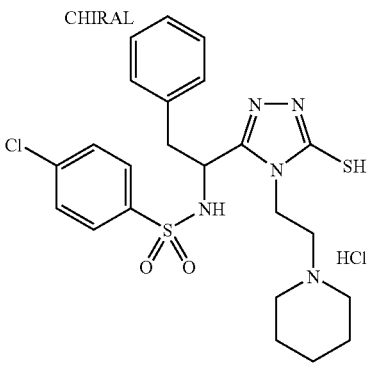 | (300 MHz, CDCl3) δ ppm: 1.24-2.45 (m, 6H), 2.68-3.04 (m, 3H), 3.17-3.32 (m, 1H), 3.50-4.02 (m, 4H), 4.39-4.91 (m, 2H), 5.13-5.35 (m, 1H), 7.00-7.24 (m, 7H), 7.44-7.53 (m, 2H), 8.92 (d, J = 6.5 Hz, 1H), 11.12 (bs, 1H), 11.81 (bs, 1H) |
| Compound 157 | 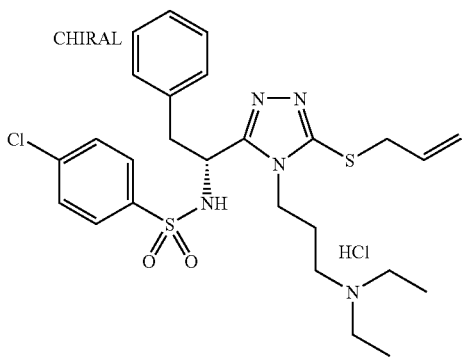 | |

TABLE 1-continued
| Compound 158 | 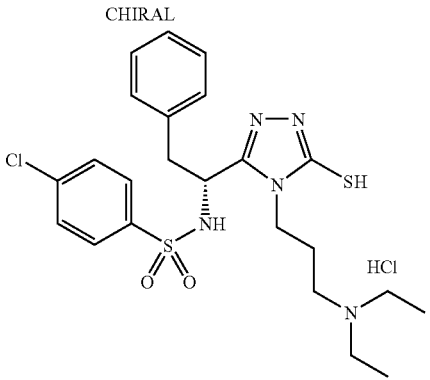 | |
| --- | --- | --- |
| Compound 159 | 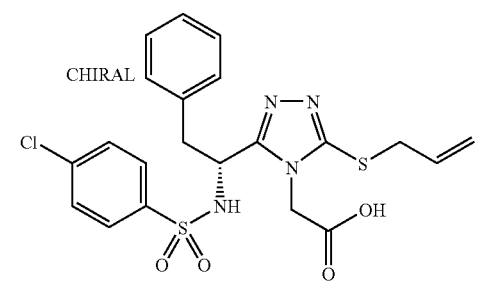 | (300 MHz, DMSO-d6) δ ppm: 2.82-3.18 (m, 2H), 3.50-3.76 (m, 2H), 4.57-4.84 (m, 3H), 4.99-5.26 (m, 2H), 5.72-5.98 (m, 1H), 6.95-7.27 (m, 5H), 7.81-7.73 (m, 4H), 8.81 (d, J = 8.6 Hz, 1H), 13.59 (bs, 1H) |
| Compound 160 | 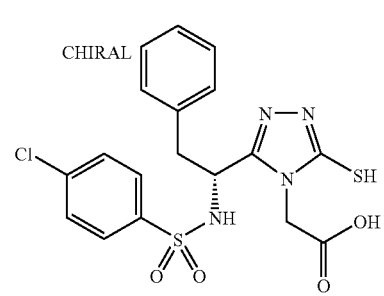 | (300 MHz, DMSO-d6) δ ppm: 2.78-3.12 (m, 2H), 4.48-4.91 (m, 3H), 7.09-7.22 (m, 5H), 7.45-7.59 (m, 4H), 8.85 (d, J = 8.4 Hz, 1H), 13.43 (bs, 1H) 13.75 (s, 1H) |
| Compound 161 | 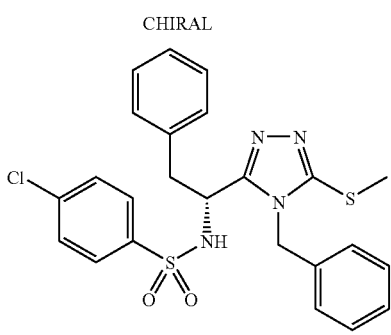 | 126.0-128.0 |
| Compound 162 | 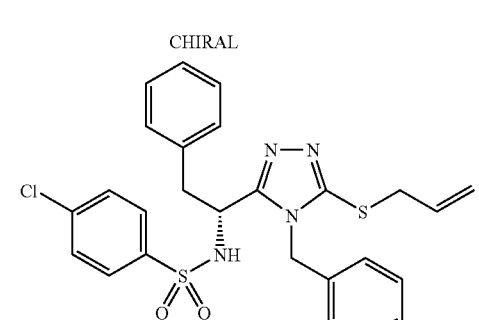 | 149.5-150.0 |

TABLE 1-continued

| Compound 163 | (structure: 4-chlorophenyl-SO2-NH-CH(CH2Ph)-[4-benzyl-5-mercapto-1,2,4-triazol-3-yl], CHIRAL) | (300 MHz, CDCl3) δ ppm: 2.27-3.06 (m, 2H), 4.35-4.70 (m, 1H), 5.29 (bs, 2H), 6.57-7.53 (m, 15H), 11.88 (bs, 1H) |
|---|---|---|
| Compound 164 | (structure: 4-chlorophenyl-SO2-NH-CH(CH2Ph)-[4-cyclopentyl-5-(allylthio)-1,2,4-triazol-3-yl], CHIRAL) | 168.0-173.0 |
| Compound 165 | (structure: 4-chlorophenyl-SO2-NH-CH(CH2Ph)-[4-cyclopentyl-5-mercapto-1,2,4-triazol-3-yl], CHIRAL) | (300 MHz, CDCl3) δ ppm: 1.45-2.10 (m, 6H), 2.20-2.00 (m, 2H), 3.10-3.25 (m, 2H), 4.55-4.70 (m, 1H), 4.80-4.90 (m, 1H), 6.88-7.69 (m, 10H), 11.78 (bs, 1H) |
| Compound 166 | (structure: 4-chlorophenyl-SO2-NH-CH(CH2Ph)-[4-phenyl-5-(allylthio)-1,2,4-triazol-3-yl], CHIRAL) | 114.0-115.5 |
| Compound 167 | (structure: 4-chlorophenyl-SO2-NH-CH(CH2Ph)-[4-phenyl-5-mercapto-1,2,4-triazol-3-yl], CHIRAL) | (300 MHz, DMSO-d6) δ ppm: 2.77-3.07 (m, 2H), 3.84-4.02 (m, 1H), 6.69-7.60 (m, 14H), 8.94 (bs, 1H), 13.91 (bs, 1H) |

TABLE 1-continued
| Compound 168 | 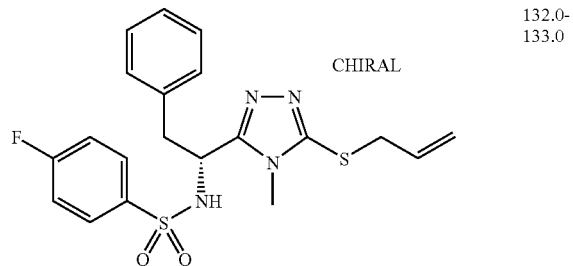 CHIRAL | 132.0-133.0 |
| --- | --- | --- |
| Compound 169 | 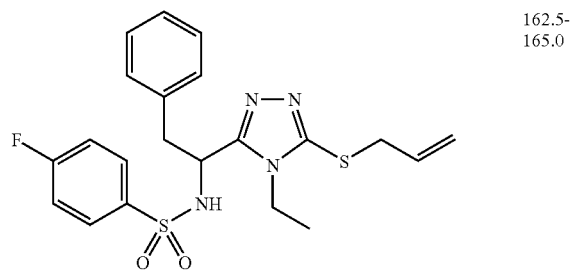 | 162.5-165.0 |
| Compound 170 | 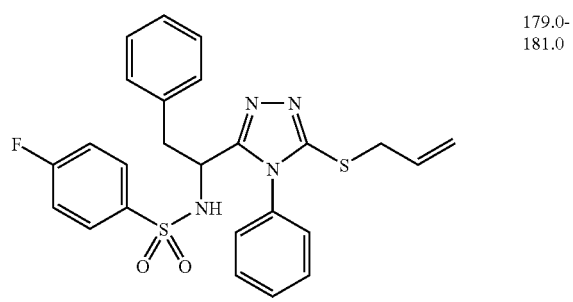 | 179.0-181.0 |
| Compound 171 | 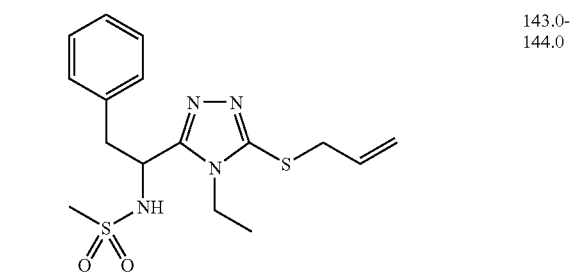 | 143.0-144.0 |
| Compound 172 | 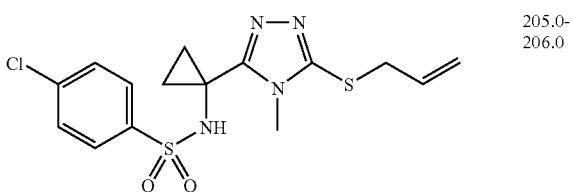 | 205.0-206.0 |
| Compound 173 | 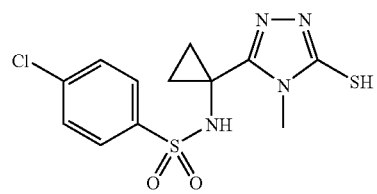 | (300 MHz, DMSO-d6) δ ppm: 0.86-1.35 (m, 4H), 3.25-3.43 (m, 3H), 7.49-7.70 (m, 4H), 9.03 (bs, 1H), 13.47 (bs, 1H) |

TABLE 1-continued

| Compound 174 | (structure) | 211.0-216.0 |
| Compound 175 | (structure) | (300 MHz, DMSO-d6) δ ppm: 1.42-1.91 (m, 2H), 2.05-2.62 (m, 4H), 3.10-3.40 (m, 3H), 7.28-7.73 (m, 4H), 8.70-8.95 (m, 1H), 13.57 (bs, 1H) |
| Compound 176 | (structure) | 225.0-226.0 |
| Compound 177 | (structure) | (300 MHz, CDCl3) δ ppm: 1.00-2.50 (m, 8H), 3.49 (s, 3H), 7.35-7.85 (m, 4H) |
| Compound 178 | (structure) | 196.0-197.0 |
| Compound 179 | (structure) | (300 MHz, CDCl3) δ ppm: 1.12-2.22 (m, 10H), 3.61 (s, 3H), 7.33-7.94 (m, 5H), 10.41 (bs, 1H) |
| Compound 180 | (structure, CHIRAL) | (300 MHz, CDCl3) δ ppm: 1.47 (t, J = 7.2 Hz, 3H), 1.54 (d, J = 6.8 Hz, 3H), 3.26 (s, 3H), 4.18-4.46 (m, 2H), 4.63-4.78 (m, 1H), 5.95 (d, J = 9.6 Hz, 1H), 7.42-7.48 (m, 2H), 7.73-7.80 (m, 2H) |
| Compound 181 | (structure, CHIRAL) | (300 MHz, CDCl3) δ ppm: 1.47 (t, J = 7.3 Hz, 3H), 1.55 (d, J = 6.8 Hz, 3H), 3.24 (s, 3H), 4.18-4.49 (m, 2H), 4.63-4.80 (m, 1H), 6.00 (d, J = 9.3 Hz, 1H), 7.42-7.49 (m, 2H), 7.67-7.75 (m, 2H) |

| | | | |
|---|---|---|---|
| Compound 182 | CHIRAL structure | 129.0-130.0 | (300 MHz, CDCl3) δ ppm: 1.46 (t, J = 7.3 Hz, 3H), 1.54-1.60 (m, 3H), 3.49 (s, 3H), 4.25-4.40 (m, 2H), 4.65-4.78 (m, 1H), 5.44 (d, J = 9.8 Hz, 1H), 7.41-7.48 (m, 2H), 7.65-7.71 (m, 2H) |
| Compound 183 | CHIRAL structure | 150.5-151.5 | |
| Compound 184 | CHIRAL structure | 154.0-155.5 | |
| Compound 185 | CHIRAL structure | 148.0-150.0 | |
| Compound 186 | CHIRAL structure | 151.0-152.0 | |
| Compound 187 | CHIRAL structure | 142.0-146.0 | |
| Compound 188 | CHIRAL structure | 86.0-90.0 | |

TABLE 1-continued

| Compound | Structure | mp (°C) / NMR |
|---|---|---|
| Compound 189 | 4-Cl-C6H4-SO2-NH-CH(CH3)-[4-ethyl-1,2,4-triazol-3-yl]-5-O-(CH2)5-N(CH3)2 (CHIRAL) | (300 MHz, CDCl3) δ ppm: 1.24 (t, J = 7.3 Hz, 3H), 1.32-1.54 (m, 6H), 1.46 (d, J = 6.8 Hz, 3H), 1.74-1.86 (m, 2H), 2.15-2.29 (m, 2H), (m, 2H), 2.21 (s, 6H), 3.70-3.80 (m, 2H), 4.40 (t, J = 6.6 Hz, 2H), 4.47-4.57 (m, 1H), 7.40-7.49 (m, 2H), 7.74-7.81 (m, 2H) |
| Compound 190 | 4-Cl-C6H4-SO2-NH-CH(CH3)-[4-ethyl-1,2,4-triazol-3-yl]-5-O-CH2CH2-OH (CHIRAL) | (300 MHz, CDCl3) δ ppm: 1.28 (t, J = 7.3 Hz, 3H), 1.45 (d, J = 7.0 Hz, 3H), 1.55-2.15 (m, 1H), 3.75-3.90 (m, 2H), 3.92-4.02 (m, 2H), 4.48-4.63 (m, 3H), 6.04 (d, J = 9.2 Hz, 1H), 7.43-7.51 (m, 2H), 7.75-7.85 (m, 2H) |
| Compound 191 | 4-Cl-C6H4-SO2-NH-CH(CH3)-[4-ethyl-1,2,4-triazol-3-yl]-5-O-(CH2)3-OH (CHIRAL) | 124.5-126.0 |
| Compound 192 | 4-Cl-C6H4-SO2-NH-CH(CH3)-[4-ethyl-1,2,4-triazol-3-yl]-5-O-(CH2)13CH3 (CHIRAL) | (300 MHz, CDCl3) δ ppm: 0.88 (t, J = 6.6 Hz, 3H), 1.07-1.93 (m, 31H), 1.46 (d, J = 6.8 Hz, 3H), 3.67-3.82 (m, 2H), 4.39 (t, J = 6.6 Hz, 2H), 4.43-4.60 (m, 1H), 5.64-6.13 (m, 1H), 7.38-7.50 (m, 2H), 7.72-7.84 (m, 2H) |
| Compound 193 | 3-Cl-C6H4-SO2-NH-CH(CH3)-[4-ethyl-1,2,4-triazol-3-yl]-5-OCH3 (CHIRAL) | 145.0-146.0 |
| Compound 194 | 2-Cl-C6H4-SO2-NH-CH(CH3)-[4-ethyl-1,2,4-triazol-3-yl]-5-OCH3 (CHIRAL) | 182.0-164.0 |
| Compound 195 | 4-MeO-C6H4-SO2-NH-CH(CH3)-[4-ethyl-1,2,4-triazol-3-yl]-5-O-propyl (CHIRAL) | 119.5-120.5 |
| Compound 196 | 4-Me-C6H4-SO2-NH-CH(CH3)-[4-ethyl-1,2,4-triazol-3-yl]-5-O-propyl (CHIRAL) | 121.0-123.0 |

TABLE 1-continued
| Compound 197 |  | 116.5-118.0 |
| --- | --- | --- |
| Compound 198 | 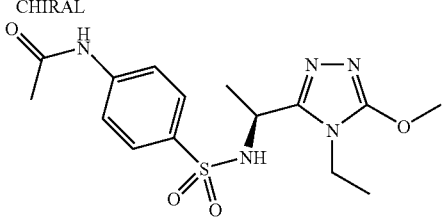 | |
| Compound 199 | 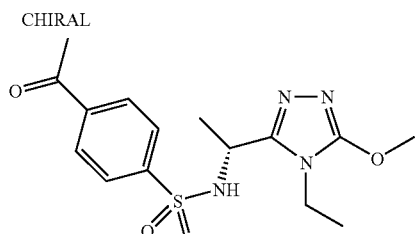 | |
| Compound 200 | 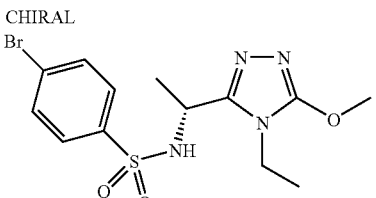 | 162.0-163.0 |
| Compound 201 | 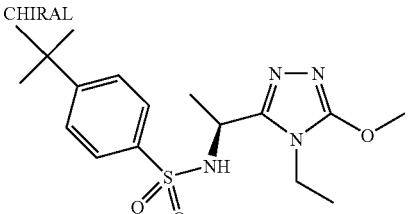 | |
| Compound 202 | 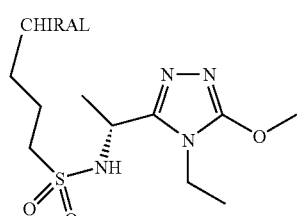 | |
| Compound 203 | 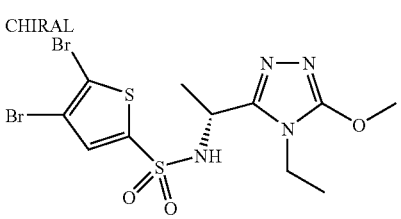 | |

TABLE 1-continued
| Compound 204 | 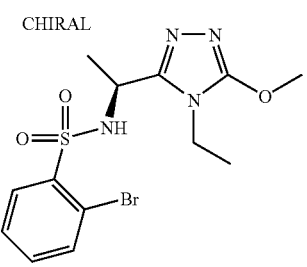 | |
| Compound 205 | 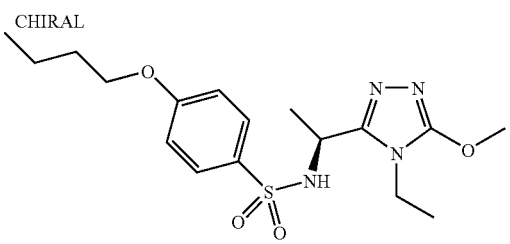 | |
| Compound 206 | 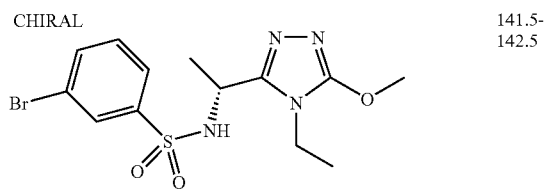 | 141.5-142.5 |
| Compound 207 | 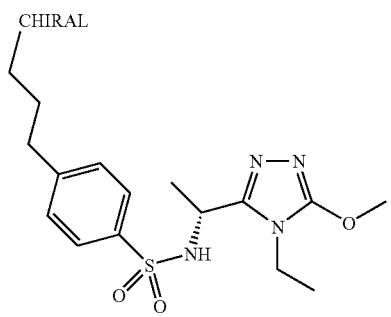 | |
| Compound 208 | 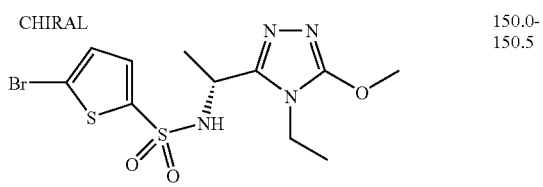 | 150.0-150.5 |
| Compound 209 | 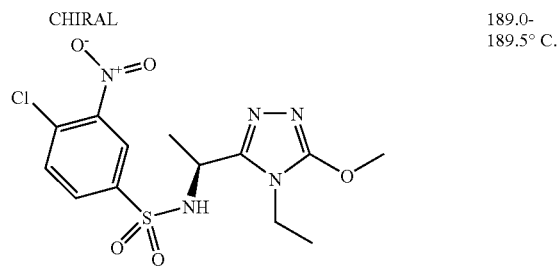 | 189.0-189.5° C. |

TABLE 1-continued
| Compound 210 | 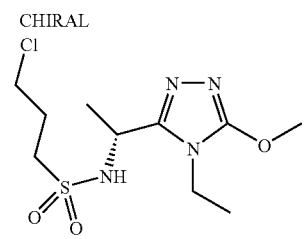 | |
| Compound 211 | 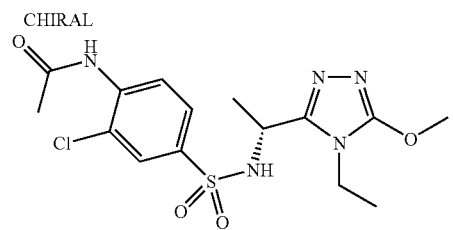 | |
| Compound 212 | 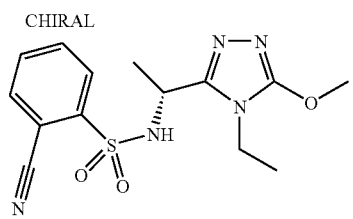 | |
| Compound 213 | 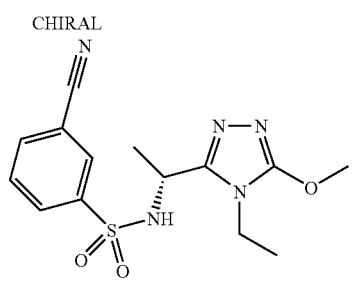 | |
| Compound 214 | 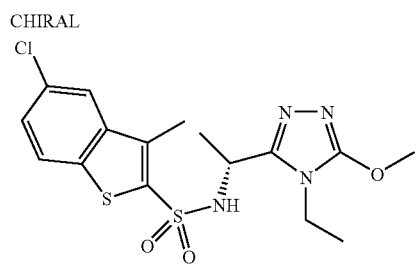 | |
| Compound 215 | 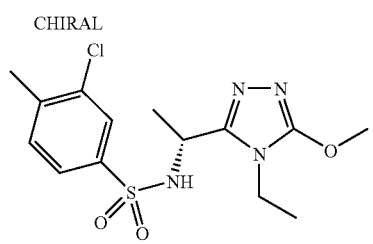 | 151.0-151.5 |

TABLE 1-continued
| Compound 216 | 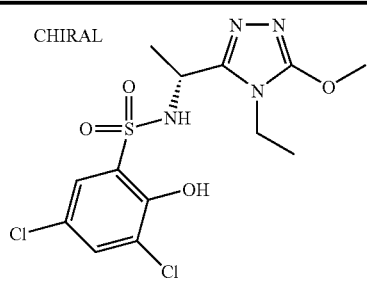 | |
| Compound 217 | 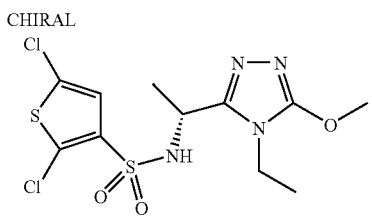 | |
| Compound 218 | 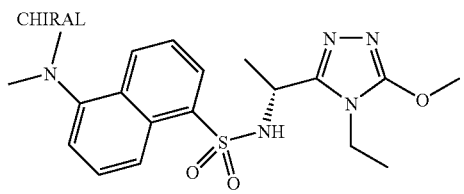 | |
| Compound 219 | 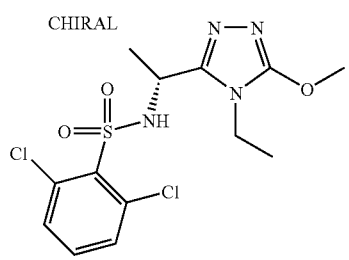 | |
| Compound 220 | 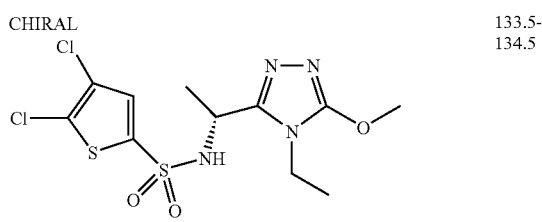 | 133.5-134.5 |
| Compound 221 | 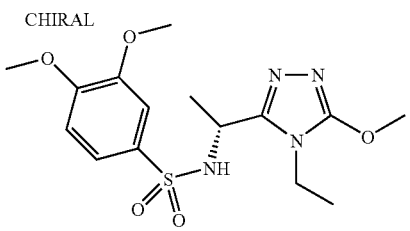 | |
| Compound 222 | 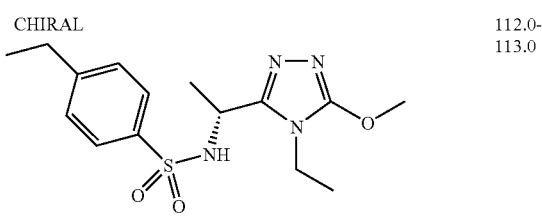 | 112.0-113.0 |

| | | | |
|---|---|---|---|
| Compound 223 | CHIRAL | 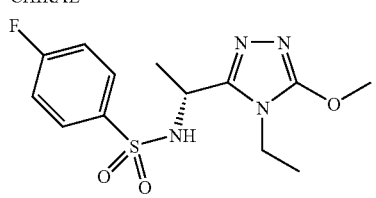 | 154.5-156.5 |
| Compound 224 | CHIRAL | 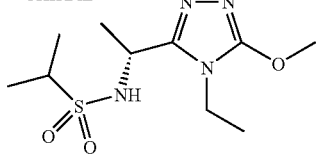 | |
| Compound 225 | CHIRAL | 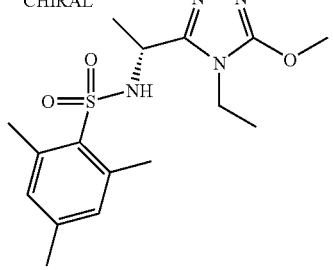 | |
| Compound 226 | CHIRAL | 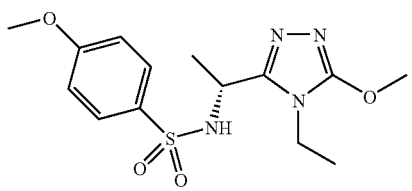 | |
| Compound 227 | CHIRAL | 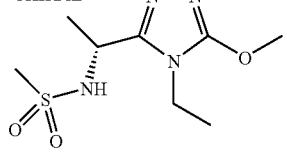 | |
| Compound 228 | CHIRAL | 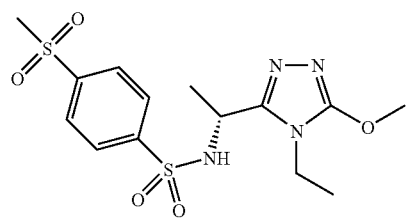 | |
| Compound 229 | CHIRAL | 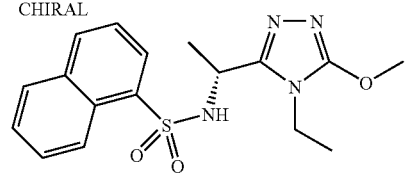 | |

TABLE 1-continued
| Compound 230 | CHIRAL 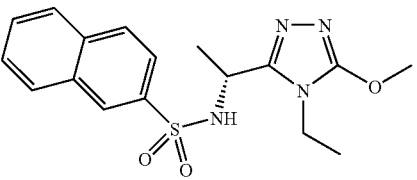 | 99.0-100.0 |
|---|---|---|
| Compound 231 | CHIRAL 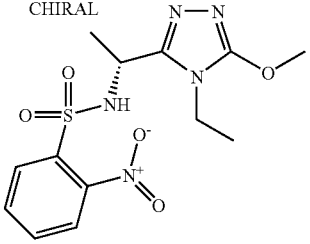 | |
| Compound 232 | CHIRAL 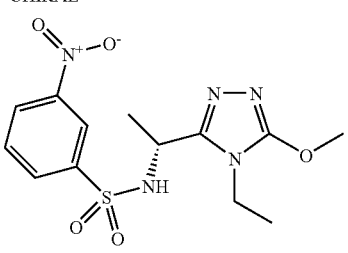 | |
| Compound 233 | CHIRAL 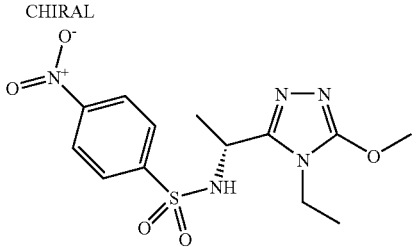 | 196.0-196.5 |
| Compound 234 | CHIRAL 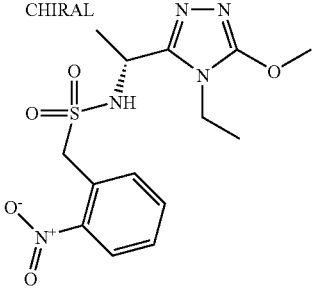 | |
| Compound 235 | CHIRAL 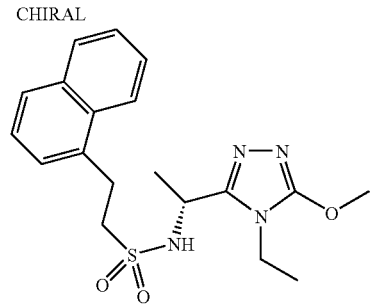 | |

TABLE 1-continued
| Compound 236 | 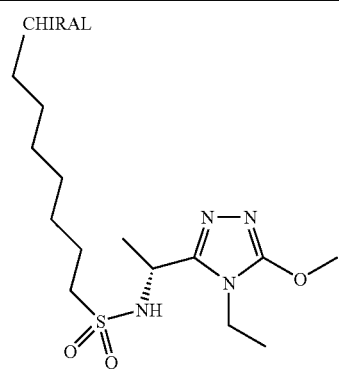 | |
| --- | --- | --- |
| Compound 237 | 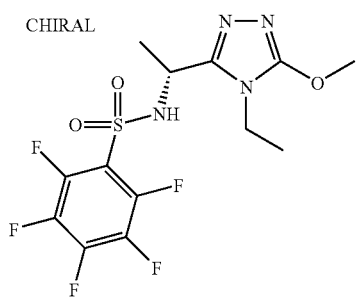 | |
| Compound 238 | 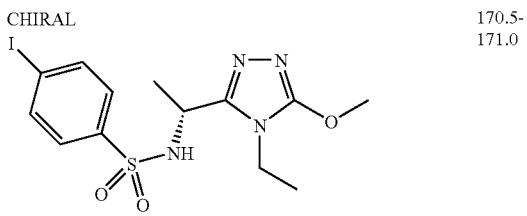 | 170.5-171.0 |
| Compound 239 | 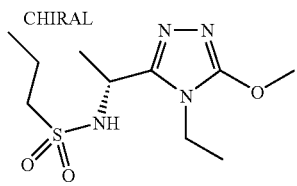 | |
| Compound 240 | 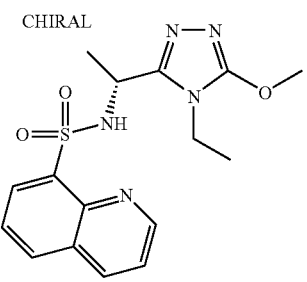 | |
| Compound 241 | 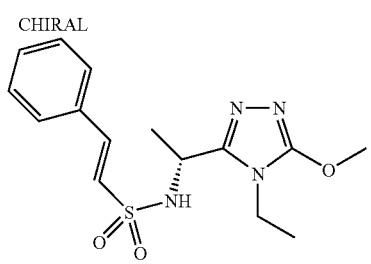 | |

TABLE 1-continued
| Compound 242 | 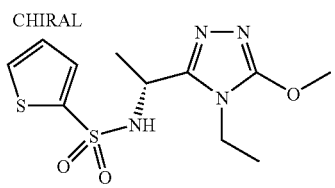 | |
| Compound 243 | 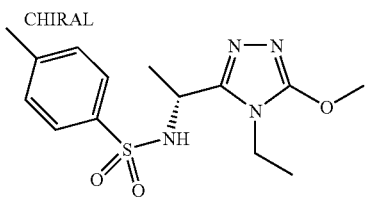 | |
| Compound 244 | 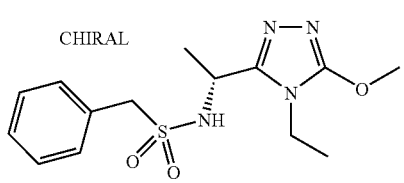 | |
| Compound 245 | 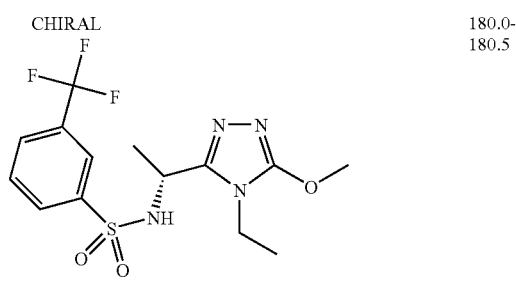 | 180.0-180.5 |
| Compound 246 | 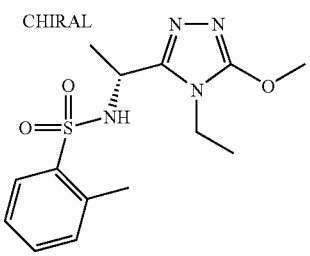 | |
| Compound 247 | 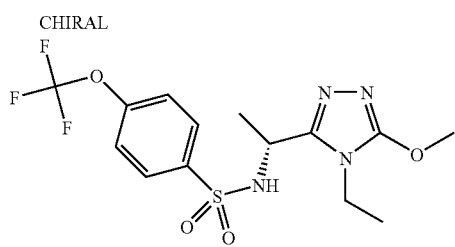 | |
| Compound 248 | 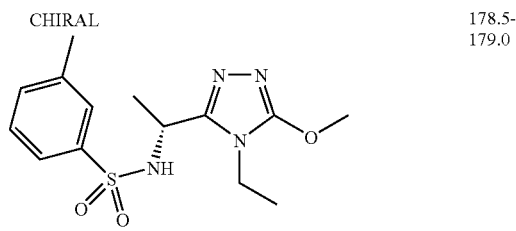 | 178.5-179.0 |

| | | | 163.5-164.5 |
|---|---|---|---|
| Compound 249 | CHIRAL 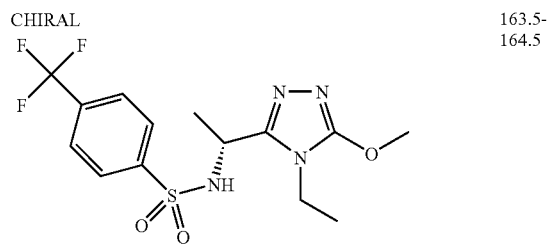 | | |
| Compound 250 | CHIRAL 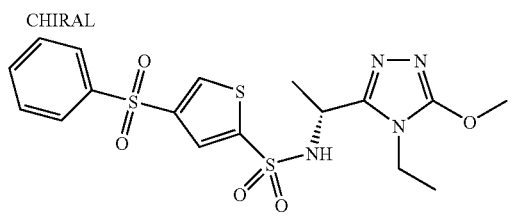 | | |
| Compound 251 | CHIRAL 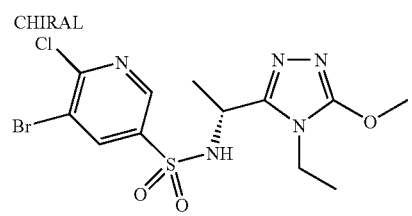 | | |
| Compound 252 | CHIRAL 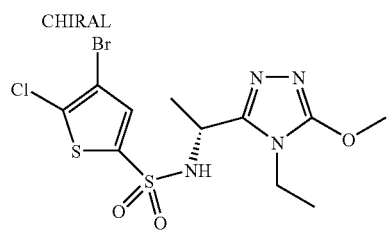 | | |
| Compound 253 | CHIRAL 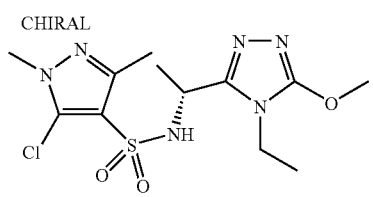 | | |
| Compound 254 | CHIRAL 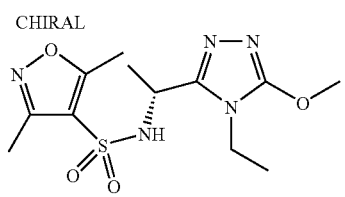 | | |
| Compound 255 | CHIRAL 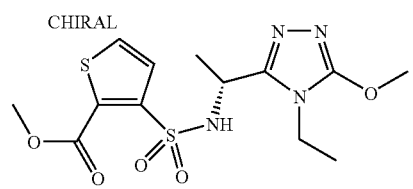 | | |

TABLE 1-continued
| Compound 256 | 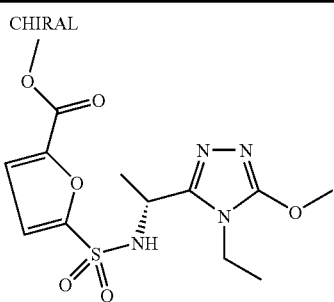 |
| --- | --- |
| Compound 257 | 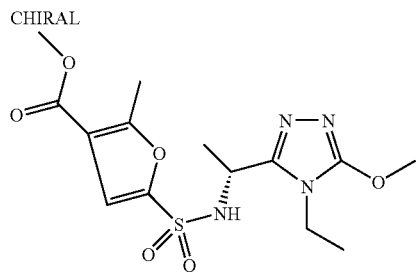 |
| Compound 258 | 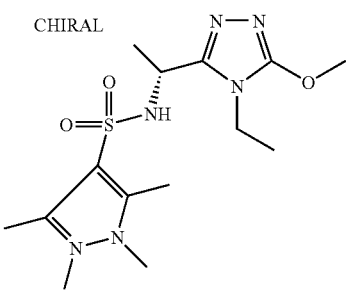 |
| Compound 259 | 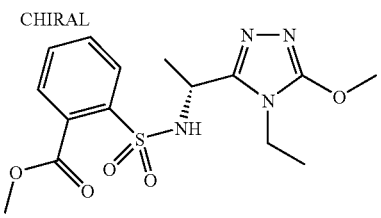 |
| Compound 260 | 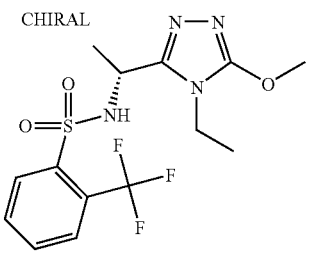 |
| Compound 261 | 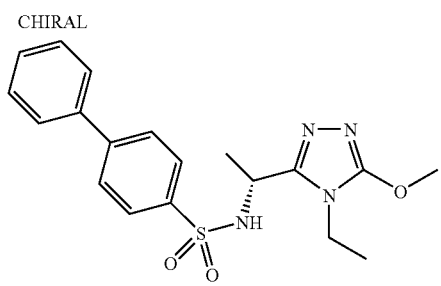 |

TABLE 1-continued

| Compound 262 | (structure: 4-propylphenyl sulfonamide linked to 1-(4-ethyl-5-methoxy-4H-1,2,4-triazol-3-yl)ethyl, CHIRAL) | |
|---|---|---|
| Compound 263 | (structure: 2-(4-chlorophenyl)-1-(4-ethyl-5-methoxy-4H-1,2,4-triazol-3-yl)ethyl 4-chlorobenzenesulfonamide, CHIRAL) | (300 MHz, CDCl3) d ppm 1.26 (t, J = 7.2 Hz, 3H) 2.92-3.03 (m, 1H) 3.05-3.17 (m, 1H) 3.25-3.53 (m, 2H) 4.04 (s, 3H) 4.42-4.53 (m, 1H) 5.93 (s, 1H) 6.64-6.73 (m, 2H) 6.76-6.83 (m, 2H) 7.34-7.41 (m, 2H) 7.62-7.69 (m, 2H) 7.70 (s, 1H) |
| Compound 264 | (structure: 2-methoxy-4-methylphenyl sulfonamide linked to 1-(4-ethyl-5-methoxy-4H-1,2,4-triazol-3-yl)ethyl, CHIRAL) | |
| Compound 265 | (structure: 3,5-bis(trifluoromethyl)phenyl sulfonamide linked to 1-(4-ethyl-5-methoxy-4H-1,2,4-triazol-3-yl)ethyl, CHIRAL) | |
| Compound 266 | (structure: 3,5-dichlorophenyl sulfonamide linked to 1-(4-ethyl-5-methoxy-4H-1,2,4-triazol-3-yl)ethyl, CHIRAL) | |
| Compound 267 | (structure: 3-chloro-2-methylphenyl sulfonamide linked to 1-(4-ethyl-5-methoxy-4H-1,2,4-triazol-3-yl)ethyl, CHIRAL) | 140.0-140.5 |

TABLE 1-continued
| Compound 268 | 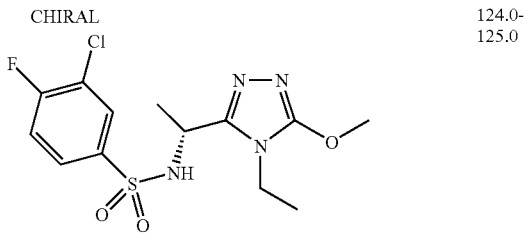 | 124.0-125.0 |
| --- | --- | --- |
| Compound 269 | 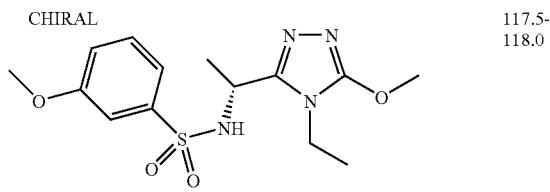 | 117.5-118.0 |
| Compound 270 | 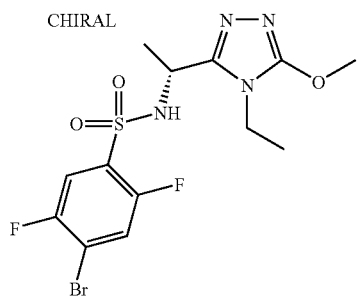 | |
| Compound 271 | 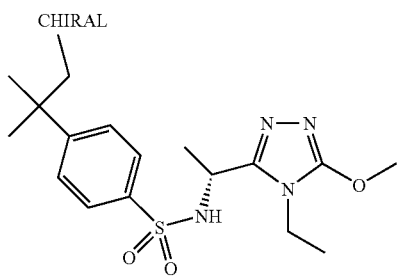 | |
| Compound 272 | 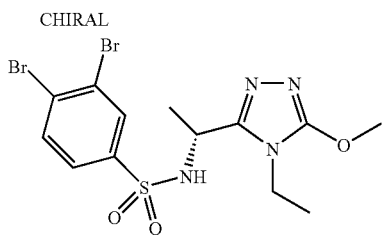 | |
| Compound 273 | 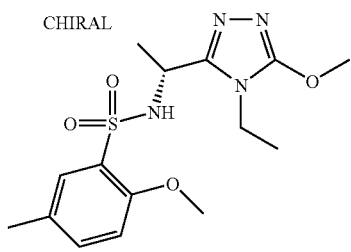 | |

| | | | |
|---|---|---|---|
| Compound 274 | CHIRAL 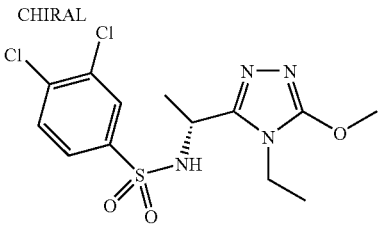 | 130.0-131.0 | |
| Compound 275 | CHIRAL 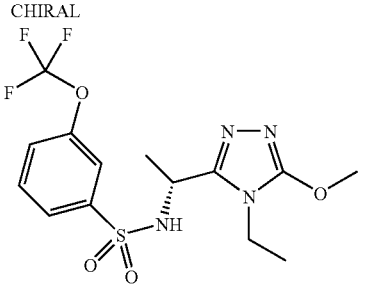 | 132.0-133.0 | |
| Compound 276 | CHIRAL 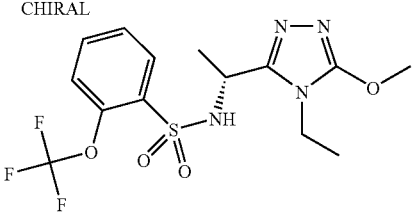 | | |
| Compound 277 | CHIRAL 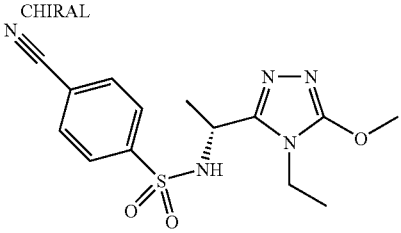 | | |
| Compound 278 | CHIRAL 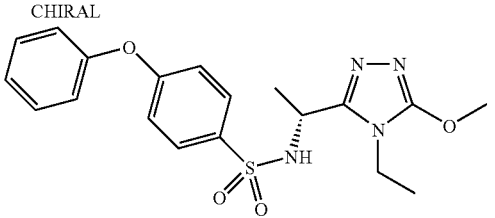 | | |
| Compound 279 | CHIRAL 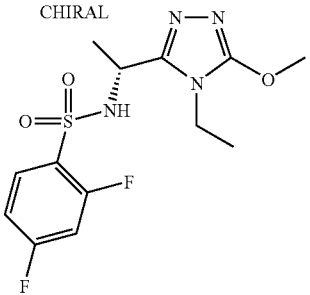 | | |

TABLE 1-continued
| Compound 280 | 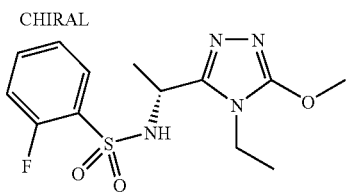 | |
| --- | --- | --- |
| Compound 281 | 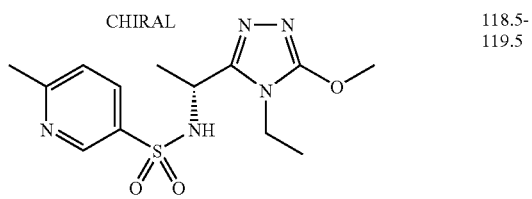 | 118.5-119.5 |
| Compound 282 | 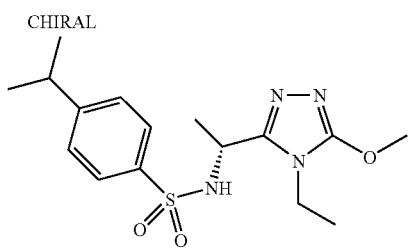 | |
| Compound 283 | 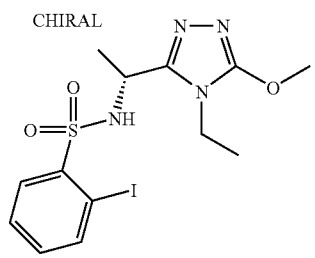 | |
| Compound 284 | 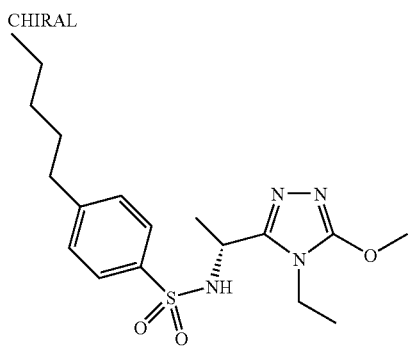 | |
| Compound 285 | 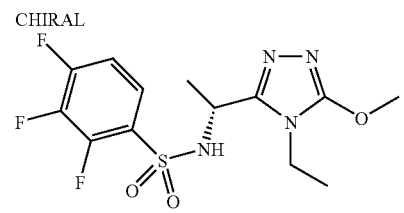 | |

TABLE 1-continued
| Compound 286 | 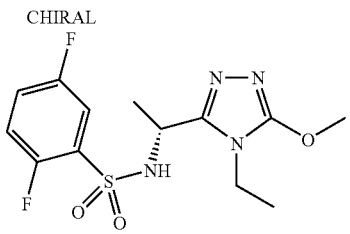 | |
| Compound 287 | 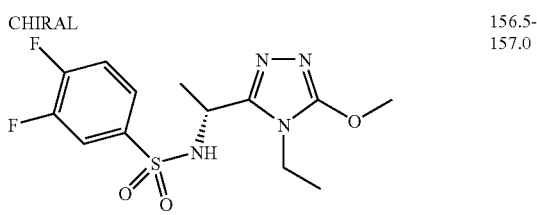 | 156.5-157.0 |
| Compound 288 | 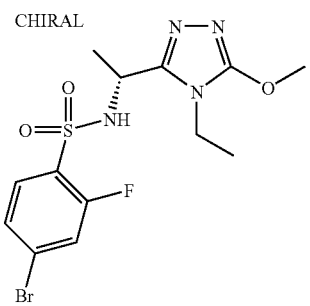 | |
| Compound 289 | 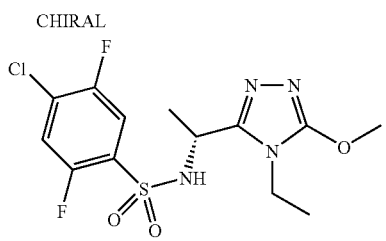 | |
| Compound 290 | 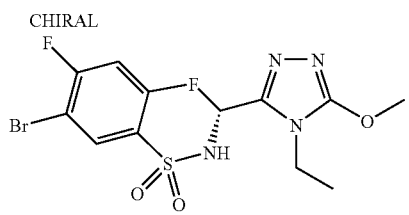 | |
| Compound 291 | 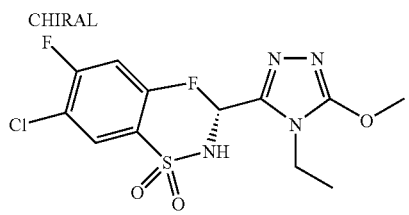 | |

TABLE 1-continued
| Compound 292 | 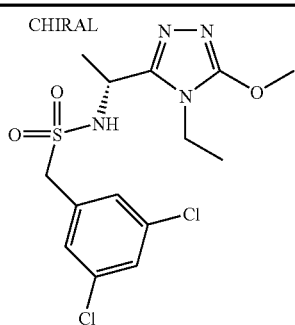 |
| Compound 293 | 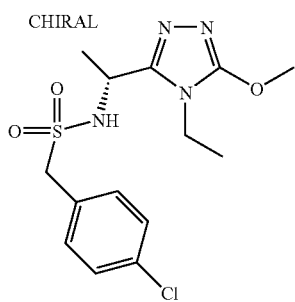 |
| Compound 294 | 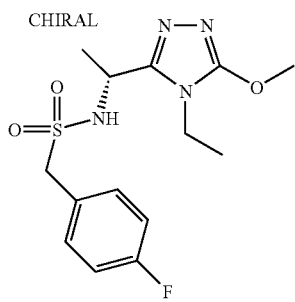 |
| Compound 295 | 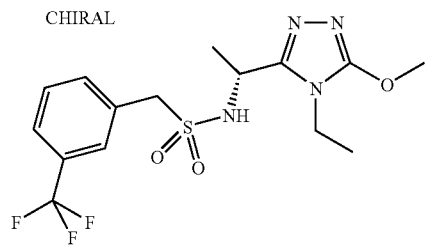 |
| Compound 296 | 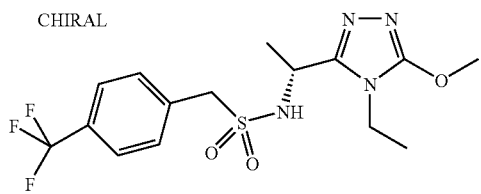 |
| Compound 297 | 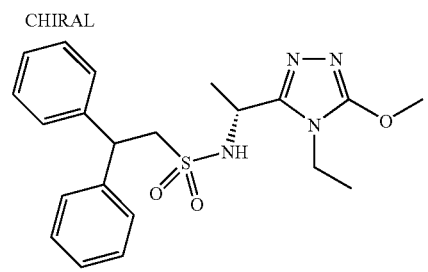 |

TABLE 1-continued
| Compound 298 | 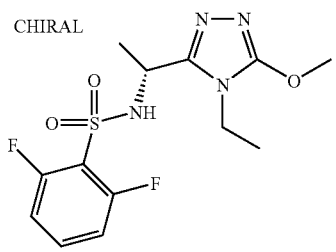 |
| Compound 299 | 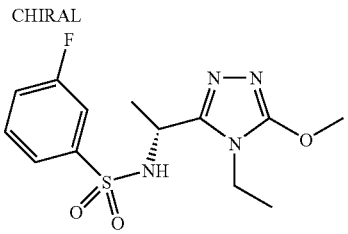 |
| Compound 300 | 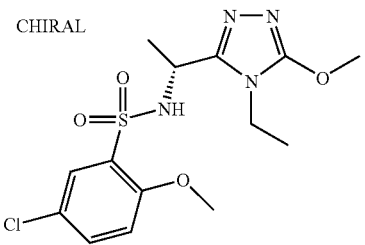 |
| Compound 301 | 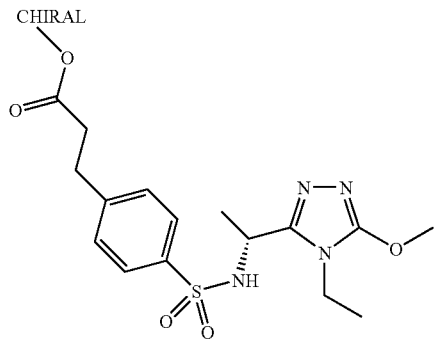 |
| Compound 302 | 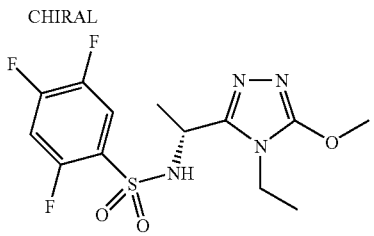 |
| Compound 303 | 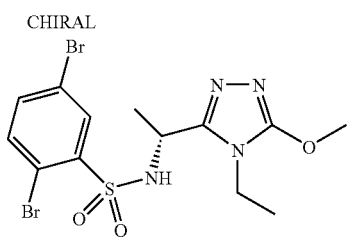 |

TABLE 1-continued
| Compound 304 | 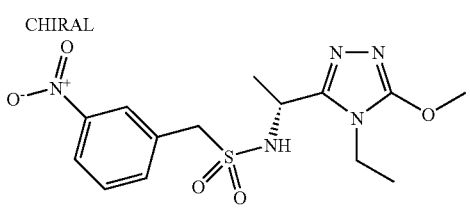 | |
| Compound 305 | 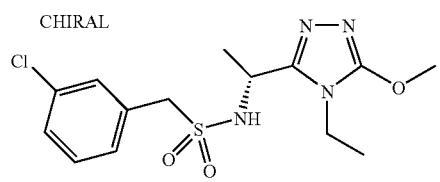 | |
| Compound 306 | 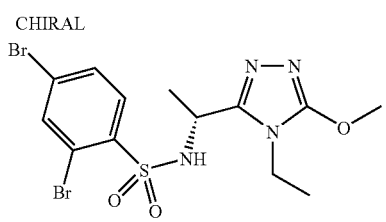 | |
| Compound 307 | 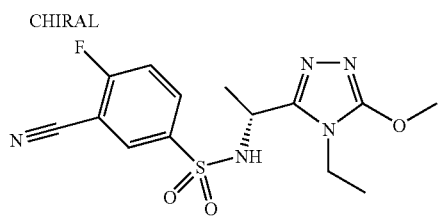 | |
| Compound 308 | 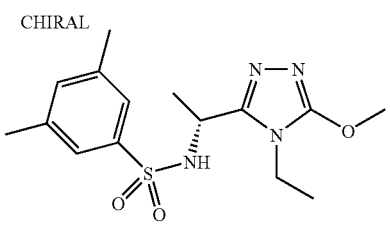 | |
| Compound 309 | 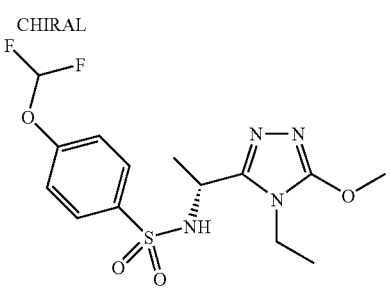 | |
| Compound 310 | 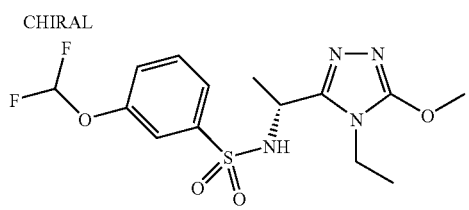 | 127.5-128.0 |

TABLE 1-continued

| Compound 311 | (CHIRAL) 3,5-difluoro-N-[(1S)-1-(4-ethyl-5-methoxy-4H-1,2,4-triazol-3-yl)ethyl]benzenesulfonamide | 138.0-139.0 |
| --- | --- | --- |
| Compound 312 | (CHIRAL) 4-chloro-N-[(1S)-1-(4-ethyl-5-methoxy-4H-1,2,4-triazol-3-yl)ethyl]-2-fluorobenzenesulfonamide | |
| Compound 313 | (CHIRAL) N-[(1S)-1-(4-ethyl-5-methoxy-4H-1,2,4-triazol-3-yl)ethyl]-3,4,5-trifluorobenzenesulfonamide | 186.0-186.5 |
| Compound 314 | (CHIRAL) 4-bromo-N-[(1S)-1-(4-ethyl-5-methoxy-4H-1,2,4-triazol-3-yl)ethyl]-3-methylbenzenesulfonamide | 156.0-156.5 |
| Compound 315 | (CHIRAL) N-[(1S)-1-(4-ethyl-5-methoxy-4H-1,2,4-triazol-3-yl)ethyl]-3-fluoro-4-methylbenzenesulfonamide | 157.0-157.5 |
| Compound 316 | (CHIRAL) 5-chloro-N-[(1S)-1-(4-ethyl-5-methoxy-4H-1,2,4-triazol-3-yl)ethyl]-2-fluorobenzenesulfonamide | |

| | | |
|---|---|---|
| Compound 317 | 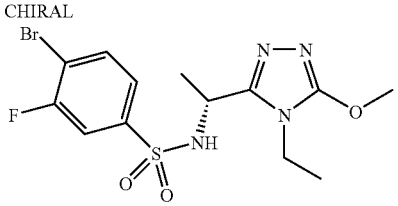 CHIRAL | 157.0-158.0 |
| Compound 318 | 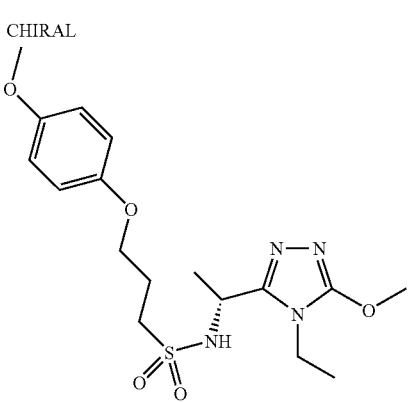 CHIRAL | |
| Compound 319 | 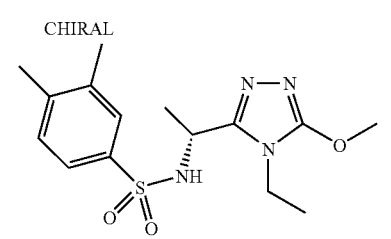 CHIRAL | 168.0-168.5 |
| Compound 320 | 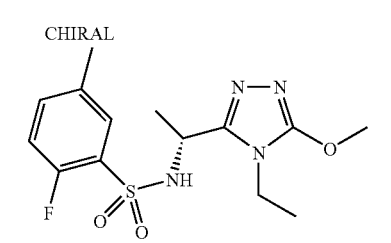 CHIRAL | |
| Compound 321 | 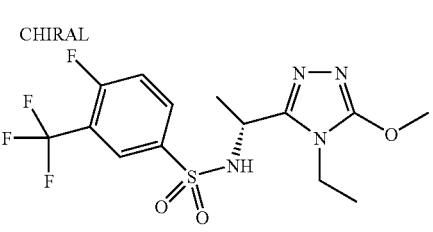 CHIRAL | 137.5-138.0 |
| Compound 322 | 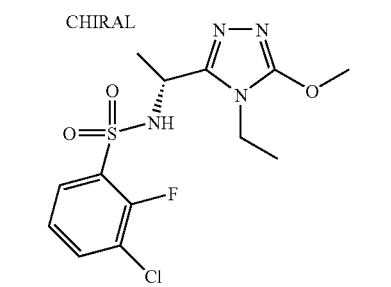 CHIRAL | |

TABLE 1-continued
| Compound 323 | 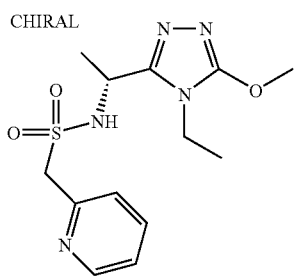 |
| Compound 324 | 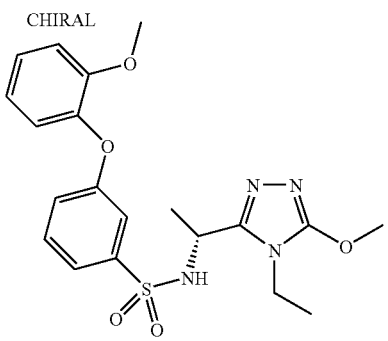 |
| Compound 325 | 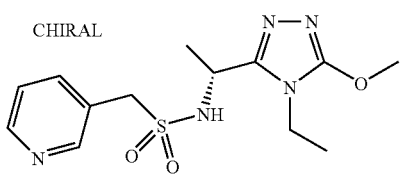 |
| Compound 326 | 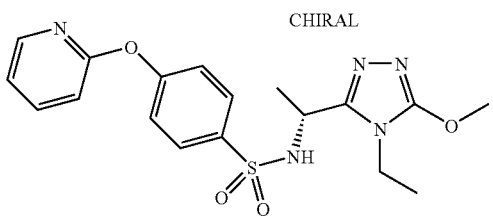 |
| Compound 327 | 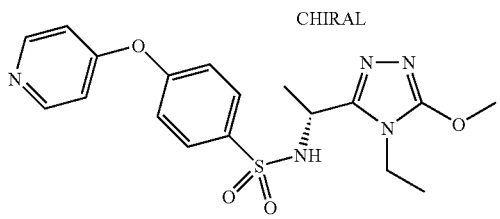 |
| Compound 328 | 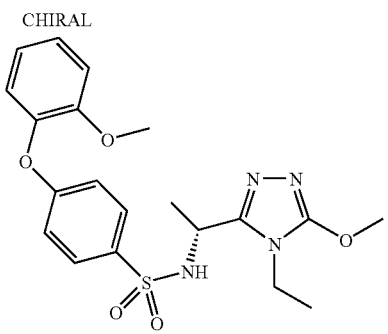 |

| | |
|---|---|
| Compound 329 | 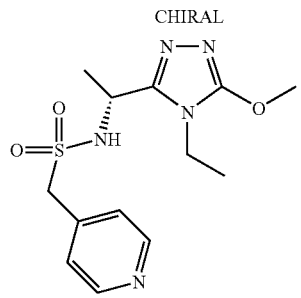 |
| Compound 330 | 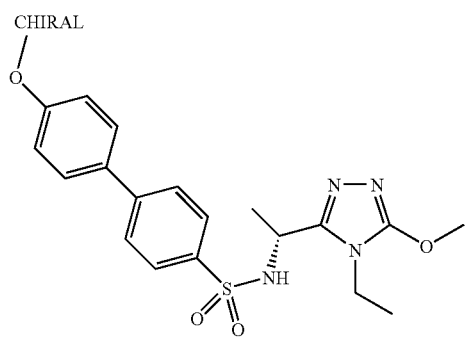 |
| Compound 331 | 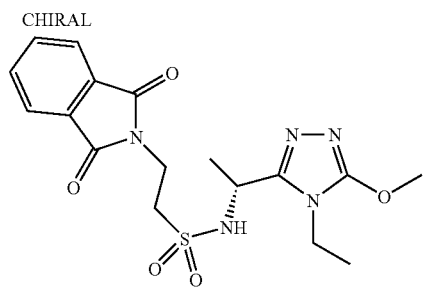 |
| Compound 332 | 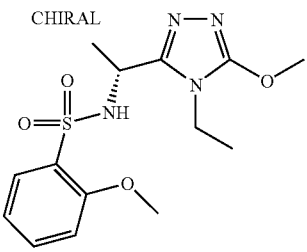 |
| Compound 333 | 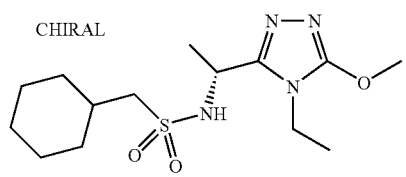 |

TABLE 1-continued
| Compound 334 | 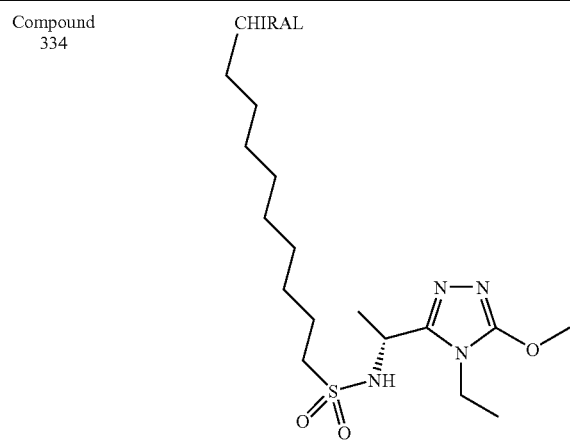 |
| Compound 335 | 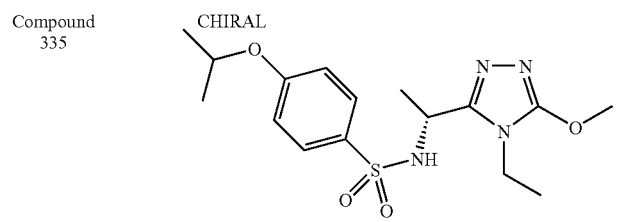 |
| Compound 336 | 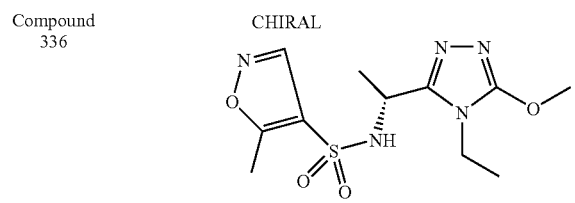 |
| Compound 337 | 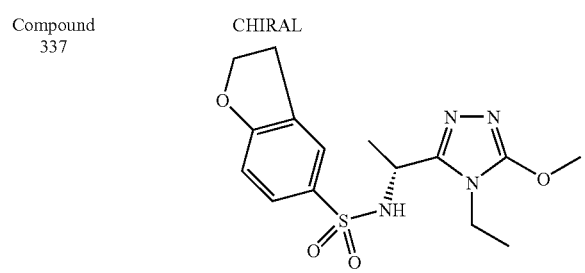 |
| Compound 338 | 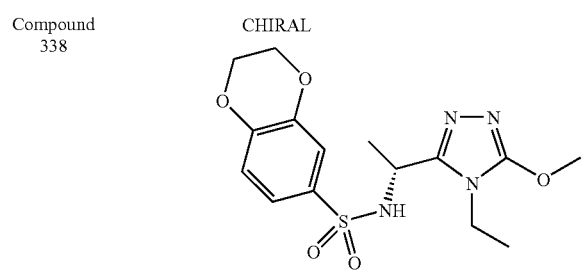 |
| Compound 339 | 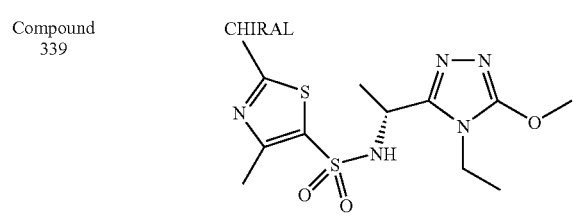 |

TABLE 1-continued
| Compound 340 | 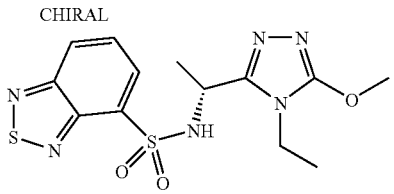 | |
| Compound 341 | 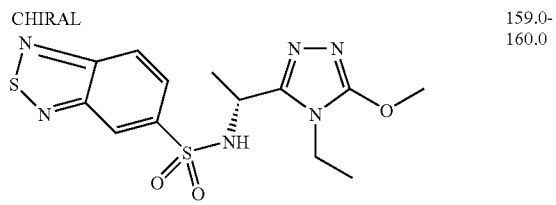 | 159.0–160.0 |
| Compound 342 | 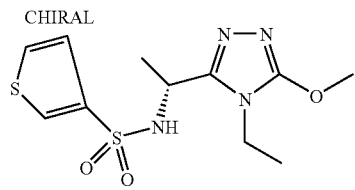 | |
| Compound 343 | 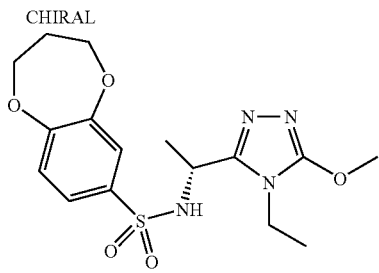 | |
| Compound 344 | 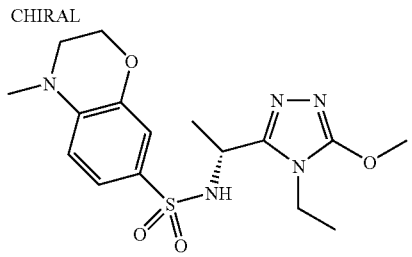 | |
| Compound 345 | 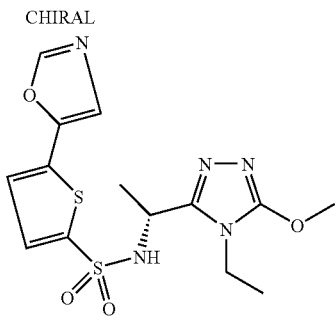 | |

TABLE 1-continued
Compound 346 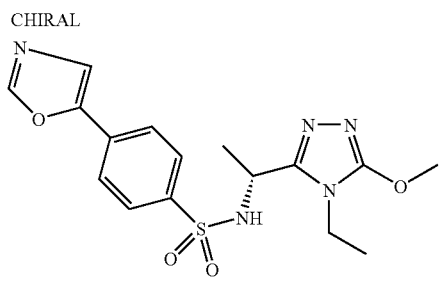
Compound 347 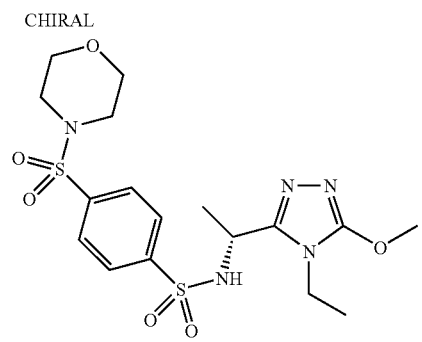
Compound 348 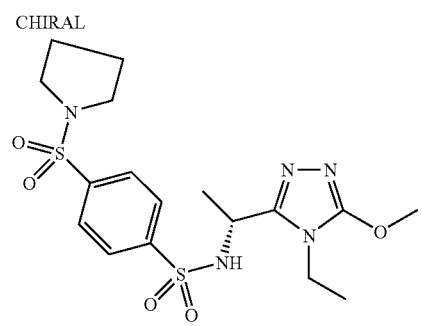
Compound 349 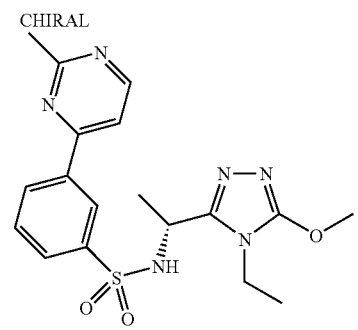
Compound 350 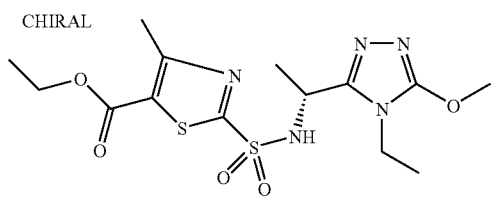

TABLE 1-continued
Compound 351  CHIRAL
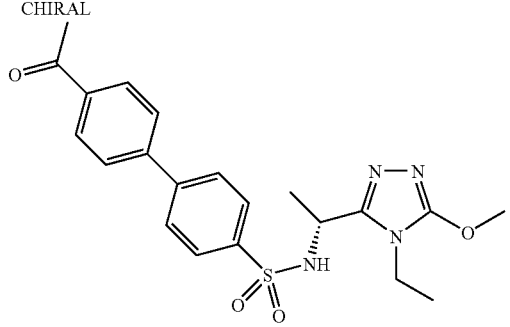
Compound 352  CHIRAL
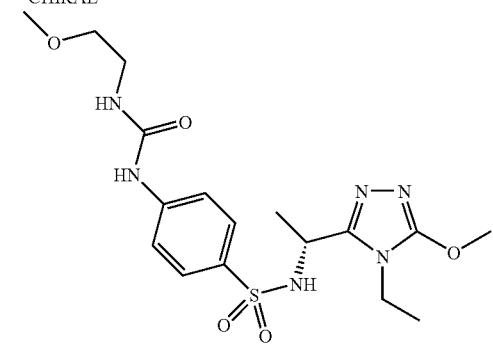
Compound 353  CHIRAL
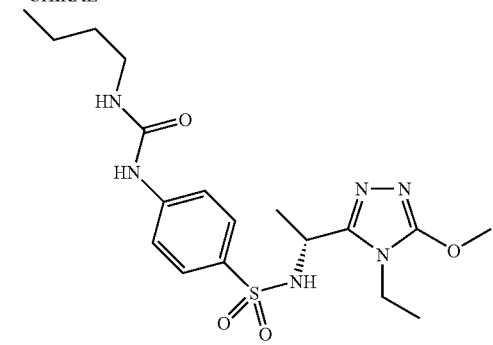
Compound 354  CHIRAL
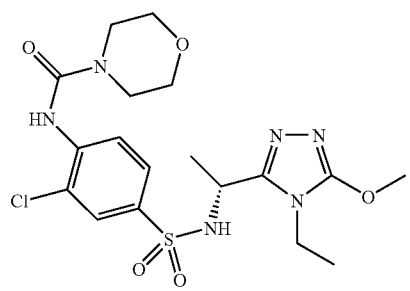

TABLE 1-continued
Compound 355 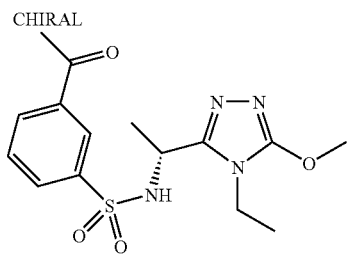
Compound 356 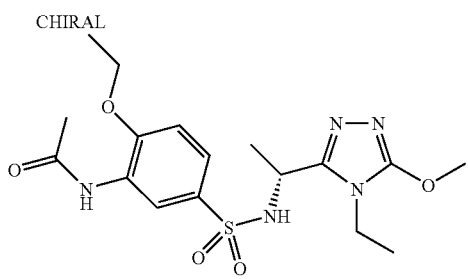
Compound 357 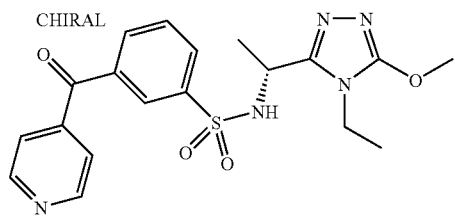
Compound 358 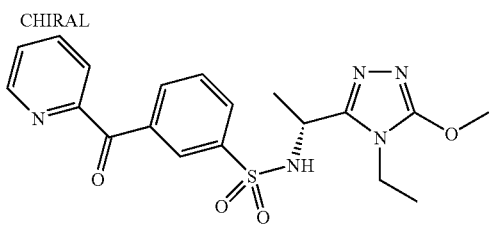
Compound 359 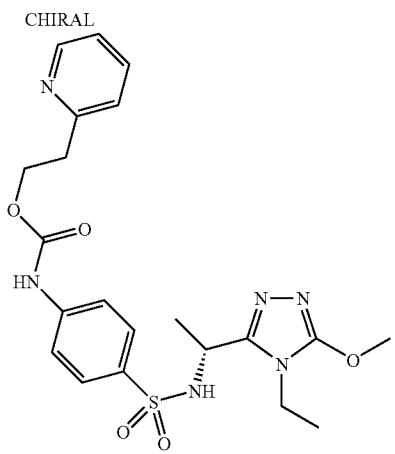

TABLE 1-continued
| Compound 360 | 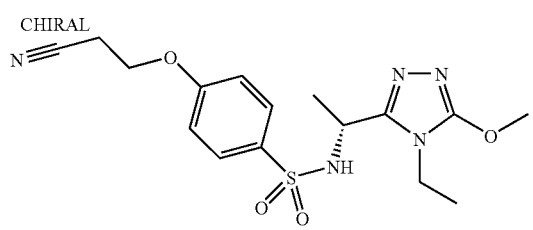 |
| --- | --- |
| Compound 361 | 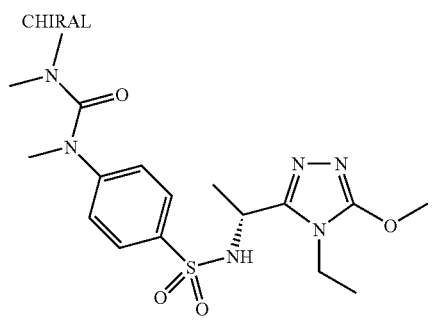 |
| Compound 362 | 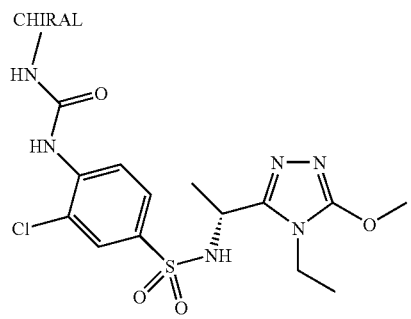 |
| Compound 363 | 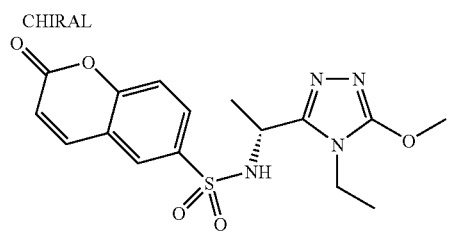 |
| Compound 364 | 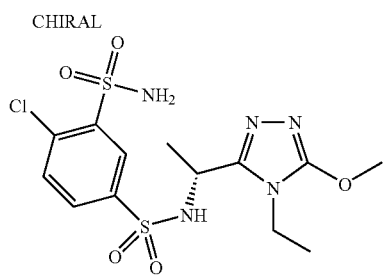 |
| Compound 365 | 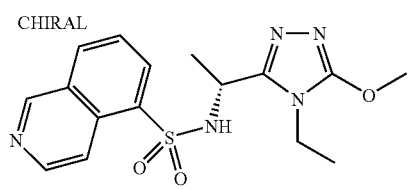 |

TABLE 1-continued
| Compound 366 | 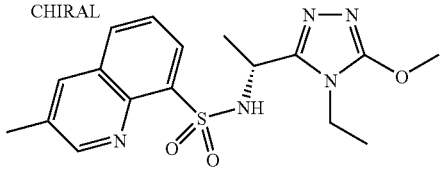 | |
| Compound 367 | 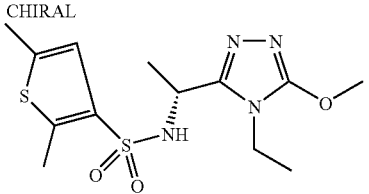 | |
| Compound 368 | 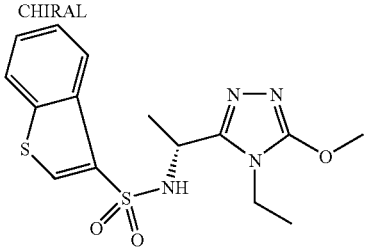 | |
| Compound 369 | 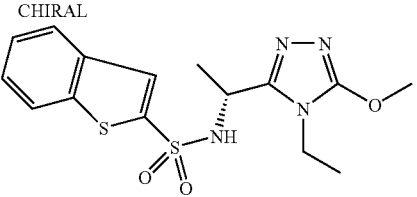 | 178.0-178.5 |
| Compound 370 | 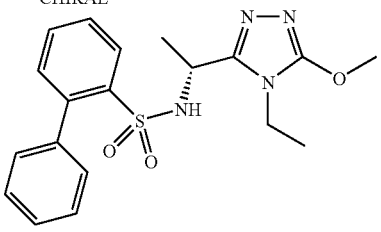 | |
| Compound 371 | 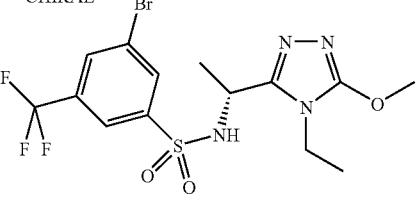 | |
| Compound 372 | 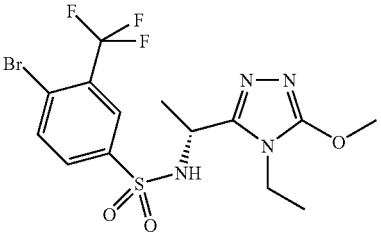 | 175.5-176.0 |

TABLE 1-continued
| Compound 373 | 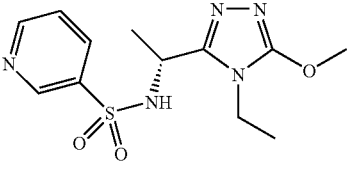 | |
| Compound 374 | 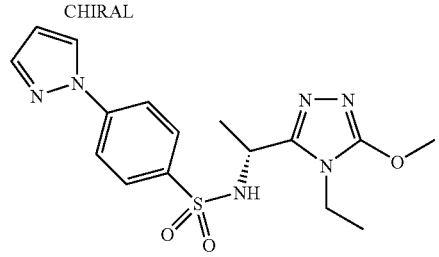 | |
| Compound 375 | 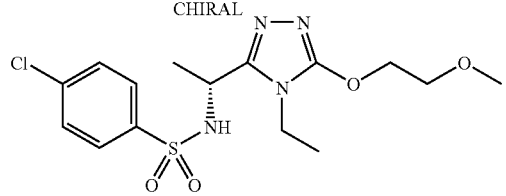 | 150.5–151.5 |
| Compound 376 | 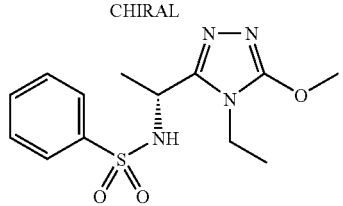 | 161.0–162.0 |
| Compound 377 | 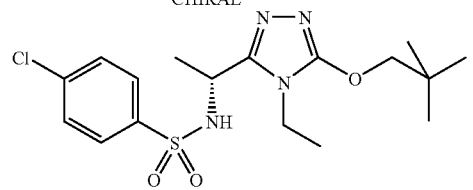 | 199.0–200.0 |
| Compound 378 | 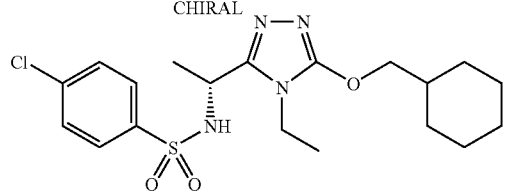 | 168.0–169.0 |
| Compound 379 | 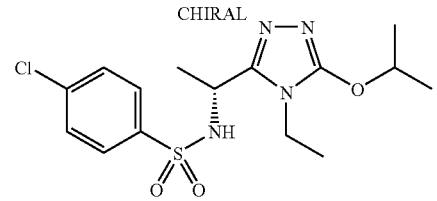 | 156.5–157.5 |

TABLE 1-continued

| Compound 380 | (structure) | (300 MHz, CDCl3) δ ppm 1.18-1.97 (m, 12H), 3.59-4.00 (m, 3H), 4.33-4.69 (m, 5H), 7.17 (br s, 1H), 7.36-7.53 (m, 2H), 7.65-7.89 (m, 2H) |
|---|---|---|
| Compound 381 | (structure) | 162.5-163.5 |
| Compound 382 | (structure) | 176.0-177.0 |
| Compound 383 | (structure) | (300 MHz, CDCl3) δ ppm: 1.14 (t, J = 7.1 Hz, 3H), 1.24 (t, J = 7.2 Hz, 3H), 1.33 (t, J = 7.2 Hz, 3H), 1.44 (d, J = 6.8 Hz, 3H), 3.27 (q, J = 7.2 Hz, 2H), 3.40 (q, J = 7.2 Hz, 2H), 3.90 (q, J = 7.1 Hz, 2H), 4.47-4.62 (m, 1H), 5.02 (d, J = 14.5 Hz, 1H), 5.12 (d, J = 14.5 Hz, 1H), 5.89 (d, J = 8.8 Hz, 1H), 7.40-7.53 (m, 2H), 7.73-7.89 (m, 2H) |
| Compound 384 | (structure) | 139.0-140.0 |
| Compound 385 | (structure) | 169.0-170.0 |
| Compound 386 | (structure) | (300 MHz, CDCl3) δ ppm: 0.76 (t, J = 7.2 Hz, 3H), 0.99 (t, J = 7.5 Hz, 3H), 1.64-1.87 (m, 2H), 3.11-3.43 (m, 4H), 4.27-4.36 (m, 2H), 4.40-4.52 (m, 1H), 6.01-6.21 (m, 1H), 6.96-7.05 (m, 2H), 7.14-7.23 (m, 3H), 7.31-7.40 (m, 2H), 7.58-7.68 (m, 2H) |

| | | |
|---|---|---|
| Compound 387 | 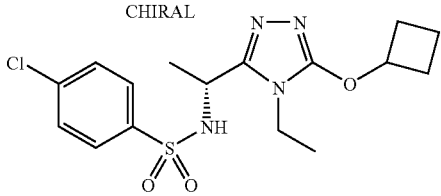 CHIRAL | 200.0-201.0 |
| Compound 388 | 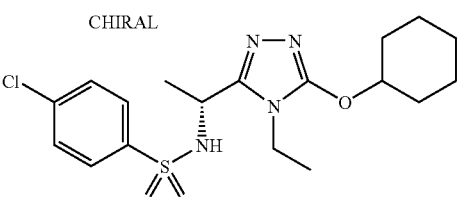 CHIRAL | 199.0-200.0 |
| Compound 389 | 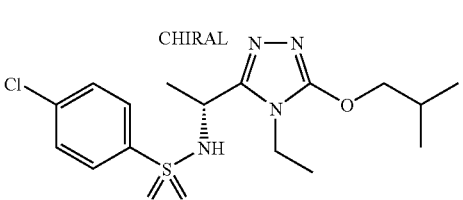 CHIRAL | 149.0-150.0 |
| Compound 390 | 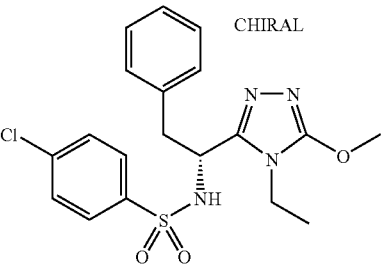 CHIRAL | 147.5-148.5 |
| Compound 391 | 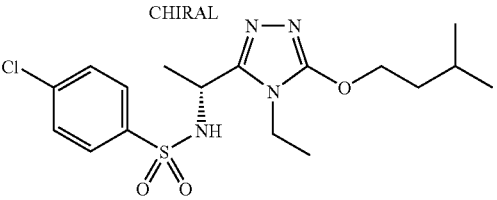 CHIRAL | 151.0-152.0 |
| Compound 392 | 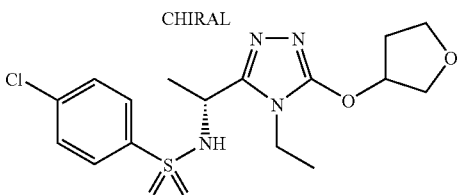 CHIRAL | 158.0-160.0 |
| Compound 393 | 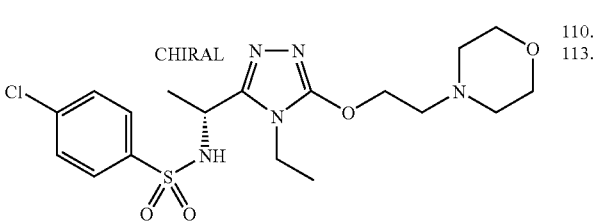 CHIRAL | 110.5-113.0 |

TABLE 1-continued
| | | |
|---|---|---|
| Compound 394 | 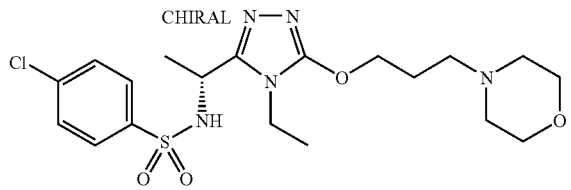 | 101.5-103.5 |
| Compound 395 | 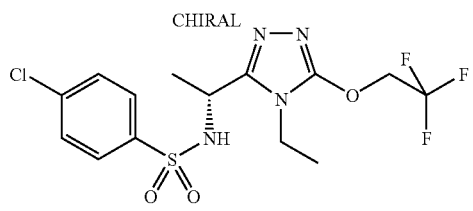 | 128.5-130.0 |
| Compound 396 | 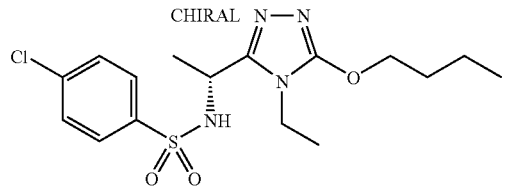 | 167.5-168.0 |
| Compound 397 | 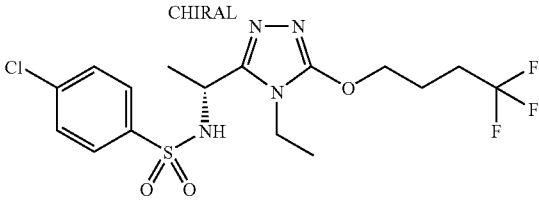 | 155.5-156.5 |
| Compound 398 | 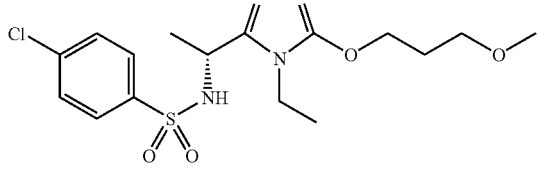 | 130.0-132.0 |
| Compound 399 | 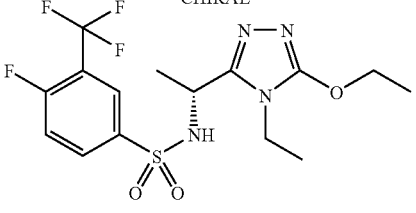 | 156.0-156.5 |
| Compound 400 | 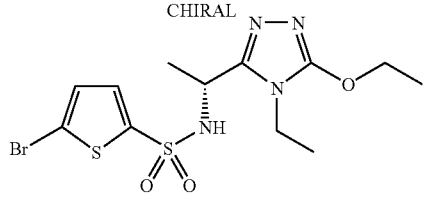 | 109.0-111.0 |

TABLE 1-continued
| | | | |
|---|---|---|---|
| Compound 401 | 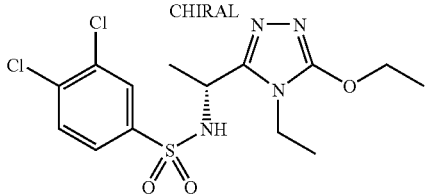 | | 149.5-150.5 |
| Compound 402 | 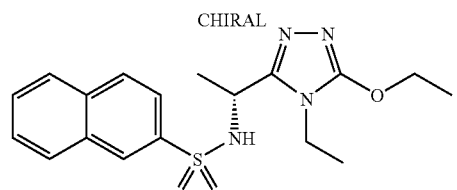 | | 164.5-166.0 |
| Compound 403 | 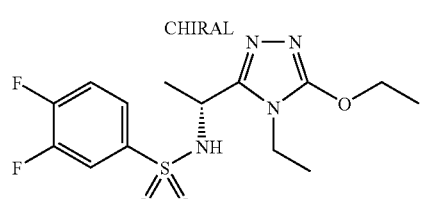 | | 184.5-185.5 |
| Compound 404 | 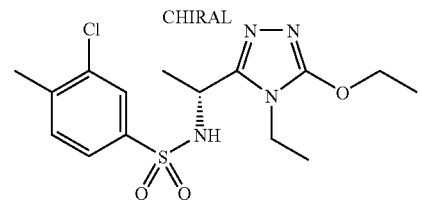 | | 140.0-140.5 |
| Compound 405 | 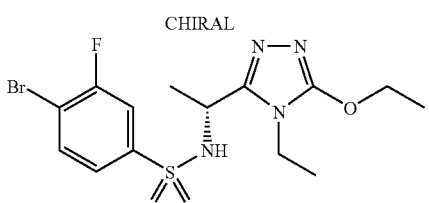 | | 172.0-172.5 |
| Compound 406 | 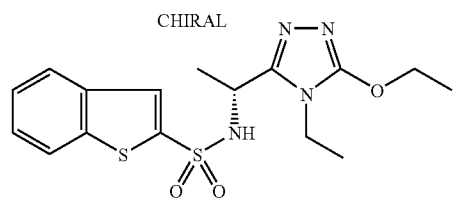 | | 184.5-185.5 |
| Compound 407 | 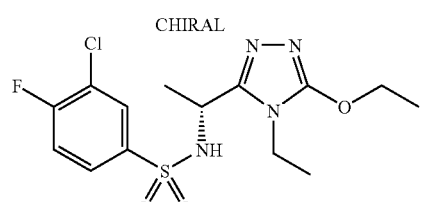 | | 167.0-168.0 |

TABLE 1-continued

| | | | |
|---|---|---|---|
| Compound 408 | *(3-bromophenyl sulfonamide with (S)-1-(5-ethoxy-4-ethyl-4H-1,2,4-triazol-3-yl)ethyl group, CHIRAL)* | 110.5-111.5 | |
| Compound 409 | *(4-bromophenyl sulfonamide with (S)-1-(5-ethoxy-4-ethyl-4H-1,2,4-triazol-3-yl)ethyl group, CHIRAL)* | 183.0-184.0 | |
| Compound 410 | *(3,4-dimethylphenyl sulfonamide with (S)-1-(5-ethoxy-4-ethyl-4H-1,2,4-triazol-3-yl)ethyl group, CHIRAL)* | 128.5-129.5 | |
| Compound 411 | *(3-fluoro-4-methylphenyl sulfonamide with (S)-1-(5-ethoxy-4-ethyl-4H-1,2,4-triazol-3-yl)ethyl group, CHIRAL)* | 135.0-136.0 | |
| Compound 412 | *(3,4-dibromophenyl sulfonamide with (S)-1-(5-ethoxy-4-ethyl-4H-1,2,4-triazol-3-yl)ethyl group, CHIRAL)* | 159.5-160.0 | |
| Compound 413 | *(4-nitrophenyl sulfonamide with (S)-1-(5-ethoxy-4-ethyl-4H-1,2,4-triazol-3-yl)ethyl group, CHIRAL)* | 175.5-176.5 | |
| Compound 414 | *(3-trifluoromethylphenyl sulfonamide with (S)-1-(5-ethoxy-4-ethyl-4H-1,2,4-triazol-3-yl)ethyl group, CHIRAL)* | 111.0-112.0 | |

| | | | |
|---|---|---|---|
| Compound 415 | (3-trifluoromethoxyphenyl structure with sulfonamide linked to chiral CH(CH₃) attached to 4-ethyl-5-ethoxy-1,2,4-triazole) | 113.0-114.0 | |
| Compound 416 | (3-difluoromethoxyphenyl structure with sulfonamide linked to chiral CH(CH₃) attached to 4-ethyl-5-ethoxy-1,2,4-triazole) | 101.0-102.0 | |
| Compound 417 | (3-methoxyphenyl structure with sulfonamide linked to chiral CH(CH₃) attached to 4-ethyl-5-ethoxy-1,2,4-triazole) | 125.0-125.5 | |
| Compound 418 | (benzo[1,3]dioxole-5-sulfonamide linked to chiral CH(CH₃) attached to 4-ethyl-5-ethoxy-1,2,4-triazole) | 181.5-182.5 | |
| Compound 419 | (3-hydroxyphenyl structure with sulfonamide linked to chiral CH(CH₃) attached to 4-ethyl-5-ethoxy-1,2,4-triazole) | 199.5-200.5 | |
| Compound 420 | (4-methoxyphenyl structure with sulfonamide linked to chiral CH(CH₃) attached to 4-ethyl-5-ethoxy-1,2,4-triazole) | 138.0-139.0 | |
| Compound 421 | (5-methylthiazole-2-sulfonamide linked to chiral CH(CH₃) attached to 4-ethyl-5-methoxy-1,2,4-triazole) | 181.0-182.0 | |

TABLE 1-continued
| | | | |
|---|---|---|---|
| Compound 422 | 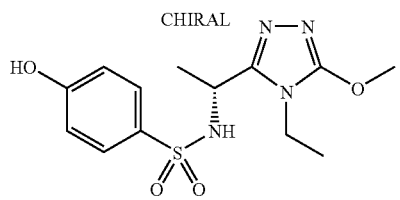 | 158.0-159.0 | |
| Compound 423 | 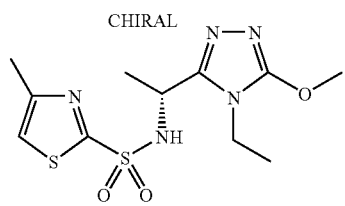 | 134.5-136.5 | |
| Compound 424 | 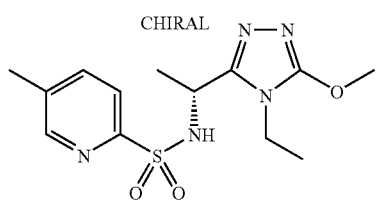 | 153.0-154.0 | |
| Compound 425 | 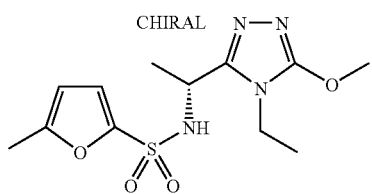 | 140.0-142.0 | |
| Compound 426 | 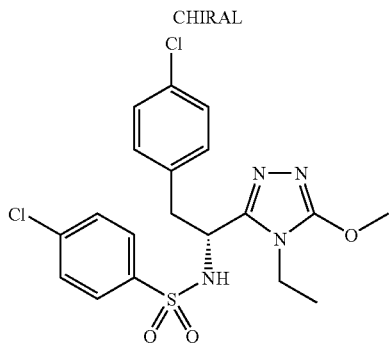 | 149.0-151.0 | |
| Compound 427 | 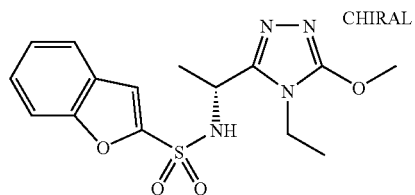 | 174.0-175.0 | |
| Compound 428 | 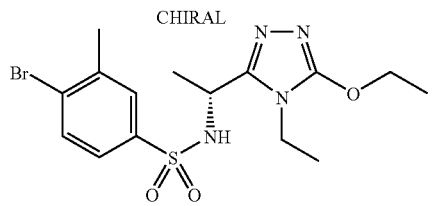 | 163.5-165.0 | |

TABLE 1-continued
| | | | |
|---|---|---|---|
| Compound 429 | CHIRAL 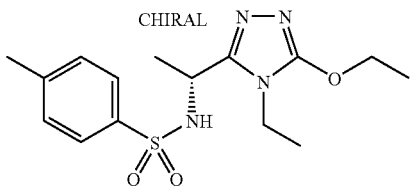 | | 114.5-115.5 |
| Compound 430 | CHIRAL 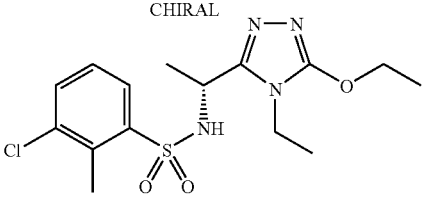 | | 139.0-140.0 |
| Compound 431 | CHIRAL 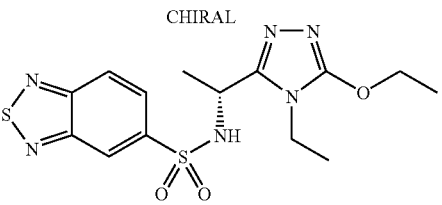 | | 148.0-149.0 |
| Compound 432 | CHIRAL 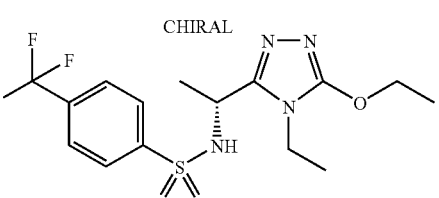 | | 146.5-147.5 |
| Compound 433 | CHIRAL 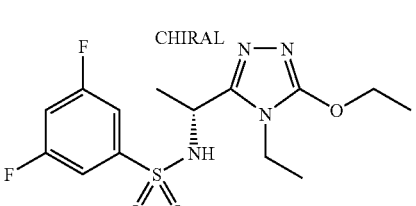 | | 169.5-170.0 |
| Compound 434 | CHIRAL 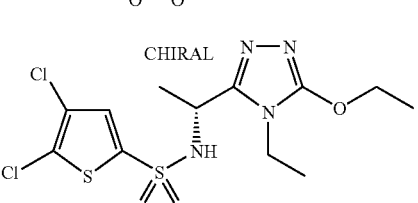 | | 165.5-166.0 |
| Compound 435 | CHIRAL 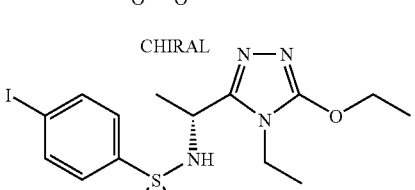 | | 204.5-205.5 |
| Compound 436 | CHIRAL 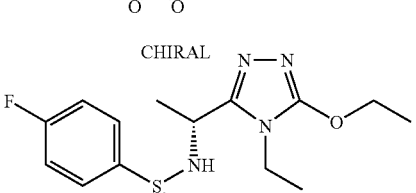 | | 172.5-173.5 |

TABLE 1-continued
| Compound 437 | 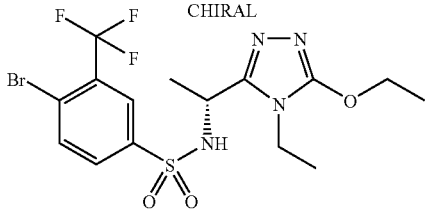 CHIRAL | 145.5-146.0 |
| Compound 438 | 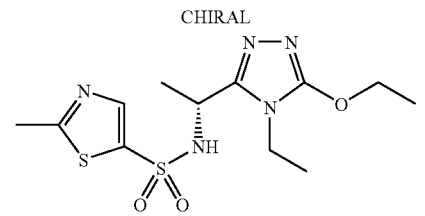 CHIRAL | 151.0-152.5 |
| Compound 439 | 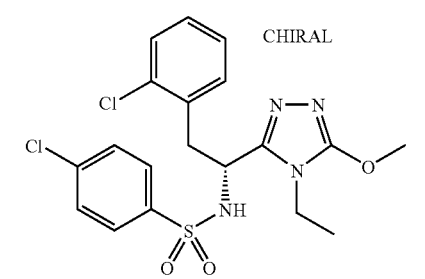 CHIRAL | 129.5-130.5 |
| Compound 440 | 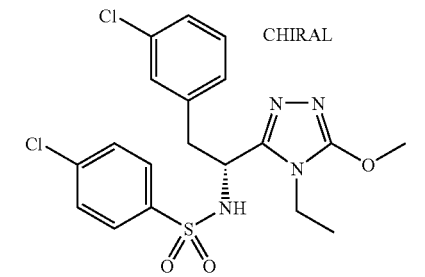 CHIRAL | 167.0-168.0 |
| Compound 441 | 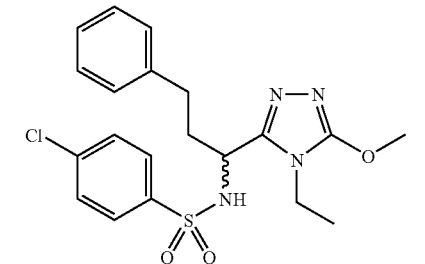 | 143.0-144.0 |
| Compound 442 | 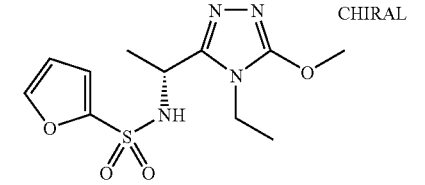 CHIRAL | 152.0-153.0 |

TABLE 1-continued

| Compound 443 | [structure] | CHIRAL | 169.0-170.0 |
| Compound 444 | [structure] | CHIRAL | 216.0-217.0 |
| Compound 445 | [structure] | CHIRAL | 133.0-136.0 |
| Compound 446 | [structure] | CHIRAL | 135.5-137.0 |
| Compound 447 | [structure] | CHIRAL | 125.5-126.5 |
| Compound 448 | [structure] | CHIRAL | 152.5-153.0 |
| Compound 449 | [structure] | CHIRAL | 161.0-165.5 |

TABLE 1-continued
| Compound 450 | 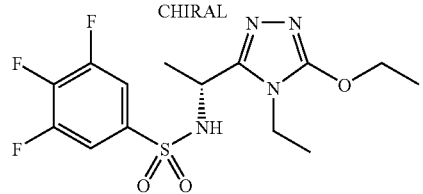 | 175.0-175.5 |
| Compound 451 | 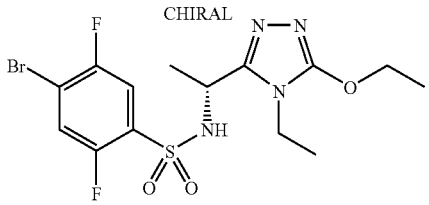 | 145.5-155.5 |
| Compound 452 | 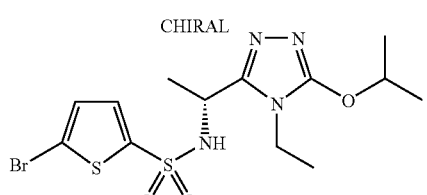 | 151.5-152.5 |
| Compound 453 | 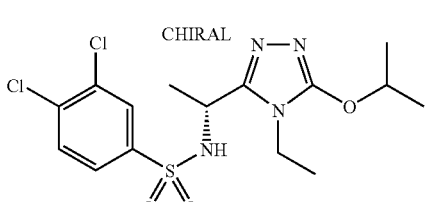 | 181.0-181.5 |
| Compound 454 | 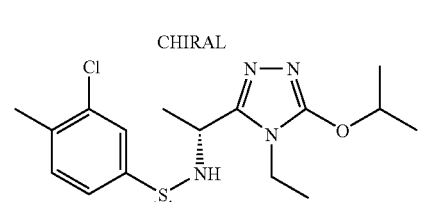 | 180.0-181.0 |
| Compound 455 | 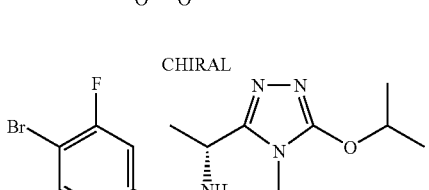 | 196.5-197.0 |
| Compound 456 | 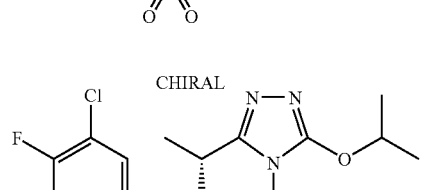 | 152.5-153.0 |

| | | | |
|---|---|---|---|
| Compound 457 | 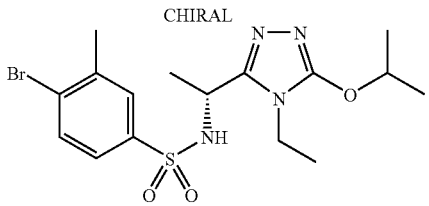 | CHIRAL | 150.0-150.5 |
| Compound 458 | 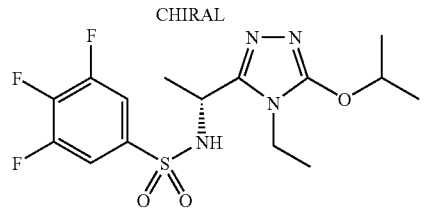 | CHIRAL | 204.5-205.0 |
| Compound 459 | 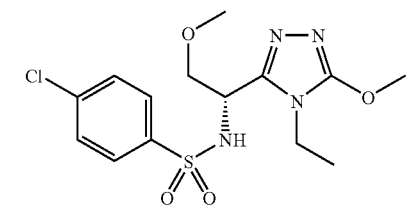 | | 150.5-151.0 |
| Compound 460 | 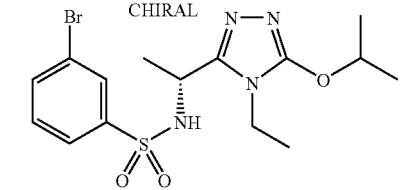 | CHIRAL | 159.5-160.5 |
| Compound 461 | 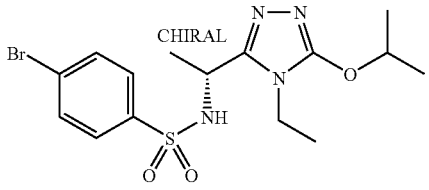 | CHIRAL | 185.0-187.0 |
| Compound 462 | 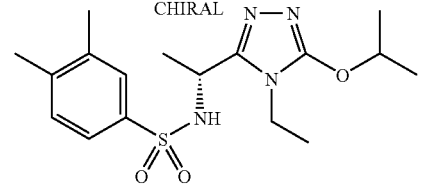 | CHIRAL | 150.0-150.5 |
| Compound 463 | 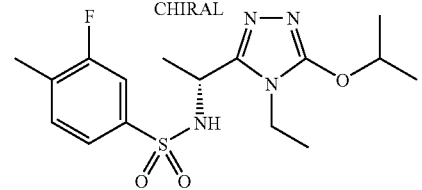 | CHIRAL | 189.5-190.0 |

| | | |
|---|---|---|
| Compound 464 | [naphthalene-SO2-NH-CH(CH3)-triazole(N-ethyl)(O-isopropyl)], CHIRAL | 188.0–189.0 |
| Compound 465 | [3,4-difluorophenyl-SO2-NH-CH(CH3)-triazole(N-ethyl)(O-isopropyl)], CHIRAL | 172.0–175.0 |
| Compound 466 | [3-(difluoromethoxy)phenyl-SO2-NH-CH(CH3)-triazole(N-ethyl)(O-isopropyl)], CHIRAL | 117.5–118.0 |
| Compound 467 | [3,4-dibromophenyl-SO2-NH-CH(CH3)-triazole(N-ethyl)(O-isopropyl)], CHIRAL | 190.0–191.0 |
| Compound 468 | [3-(trifluoromethyl)phenyl-SO2-NH-CH(CH3)-triazole(N-ethyl)(O-isopropyl)], CHIRAL | 123.5–124.0 |
| Compound 469 | [3-(trifluoromethoxy)phenyl-SO2-NH-CH(CH3)-triazole(N-ethyl)(O-isopropyl)], CHIRAL | 120.0–121.0 |
| Compound 470 | [3-methylphenyl-SO2-NH-CH(CH3)-triazole(N-ethyl)(O-isopropyl)], CHIRAL | 145.5–147.0 |

TABLE 1-continued
| Compound 471 | 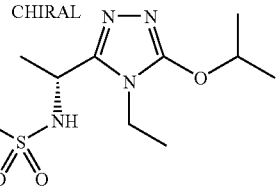 | 147.0-149.0 |
| Compound 472 | 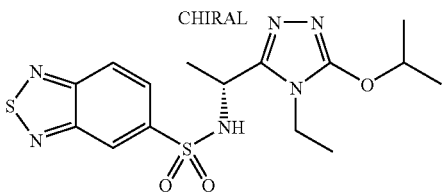 | 159.0-161.0 |
| Compound 473 | 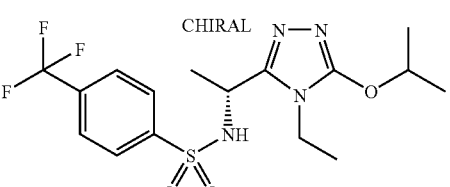 | 191.0-192.0 |
| Compound 474 | 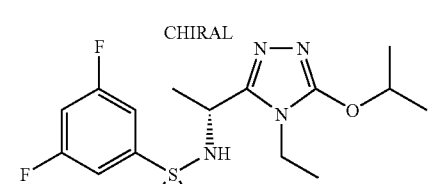 | 197.5-198.0 |
| Compound 475 | 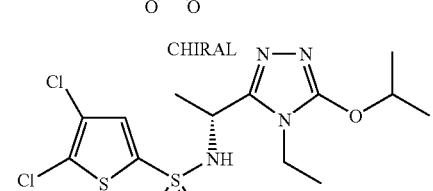 | 206.5-207.5 |
| Compound 476 | 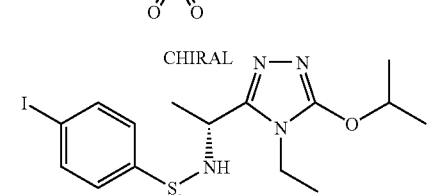 | 205.5-206.5 |
| Compound 477 | 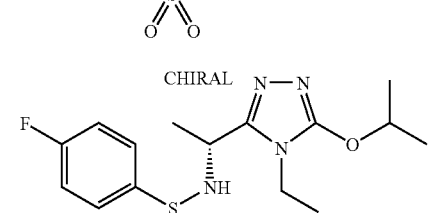 | 151.5-153.5 |
| Compound 478 | 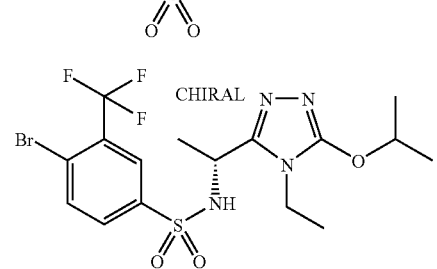 | 183.0-184.0 |

| | | |
|---|---|---|
| Compound 479 | [3-chlorophenyl-SO2-NH-CH(CH3)-(4-ethyl-5-isopropoxy-4H-1,2,4-triazol-3-yl), CHIRAL] | 168.5-169.0 |
| Compound 480 | [4-ethylphenyl-SO2-NH-CH(CH3)-(4-ethyl-5-isopropoxy-4H-1,2,4-triazol-3-yl), CHIRAL] | 158.0-158.5 |
| Compound 481 | [3-methoxyphenyl-SO2-NH-CH(CH3)-(4-ethyl-5-isopropoxy-4H-1,2,4-triazol-3-yl), CHIRAL] | 110.0-111.0 |
| Compound 482 | [4-bromo-2,5-difluorophenyl-SO2-NH-CH(CH3)-(4-ethyl-5-isopropoxy-4H-1,2,4-triazol-3-yl), CHIRAL] | 160.0-163.0 |
| Compound 483 | [4-chlorophenyl-SO2-NH-CH(CH2OH)-(4-ethyl-5-methoxy-4H-1,2,4-triazol-3-yl), CHIRAL] | 79.0-81.0 |
| Compound 484 | [5-bromothiophene-2-SO2-NH-CH(CH3)-(4-ethyl-5-(2,2,2-trifluoroethoxy)-4H-1,2,4-triazol-3-yl), CHIRAL] | 78.0-81.0 |
| Compound 485 | [3,4-dichlorophenyl-SO2-NH-CH(CH3)-(4-ethyl-5-(2,2,2-trifluoroethoxy)-4H-1,2,4-triazol-3-yl), CHIRAL] | 157.5-158.5 |

TABLE 1-continued

| Compound 486 | (structure) | 145.0-146.0 |
| Compound 487 | (structure) | 173.0-174.0 |
| Compound 488 | (structure) | 137.0-138.0 |
| Compound 489 | (structure) | 127.0-128.0 |
| Compound 490 | (structure) | 155.0-156.0 |
| Compound 491 | (structure) | 94.0-95.0 |
| Compound 492 | (structure) | 150.0-151.0 |

TABLE 1-continued

| Compound 493 | (structure) | 109.0-110.0 | |
| --- | --- | --- | --- |
| Compound 494 | (structure) | 169.0-170.0 | |
| Compound 495 | (structure) | 139.5-140.5 | |
| Compound 496 | (structure) | 139.0-140.0 | |
| Compound 497 | (structure) | 93.0-94.0 | |
| Compound 498 | (structure) | | (300 MHz, CDCl3) δ ppm: 1.28 (t, J = 7.2 Hz, 3H), 1.47 (d, J = 6.8 Hz, 3H), 2.69 (s, 3H), 3.37-3.83 (m, 2H), 4.46-4.58 (m, 1H), 5.43 (brd, J = 8.9 Hz, 1H), 7.21-7.29 (m, 1H), 7.57 (d, J = 1.1, 7.9 Hz, 1H), 7.92 (d, J = 1.1, 8.1 Hz, 1H) |
| Compound 499 | (structure) | 127.0-128.0 | |
| Compound 500 | (structure) | 143.5-144.5 | |

TABLE 1-continued

| Compound 501 | (structure: 3,5-difluorophenyl-SO2-NH-CH(CH3)-[4-ethyl-5-(2,2,2-trifluoroethoxy)-4H-1,2,4-triazol-3-yl], CHIRAL) | 145.5-146.5 |
| Compound 502 | (structure: 3,4-dibromophenyl-SO2-NH-CH(CH3)-[4-ethyl-5-(2,2,2-trifluoroethoxy)-4H-1,2,4-triazol-3-yl], CHIRAL) | 170.0-171.0 |
| Compound 503 | (structure: 3-trifluoromethylphenyl-SO2-NH-CH(CH3)-[4-ethyl-5-(2,2,2-trifluoroethoxy)-4H-1,2,4-triazol-3-yl], CHIRAL) | 123.0-124.0 |
| Compound 504 | (structure: 3-trifluoromethoxyphenyl-SO2-NH-CH(CH3)-[4-ethyl-5-(2,2,2-trifluoroethoxy)-4H-1,2,4-triazol-3-yl], CHIRAL) | 103.0-104.0 |
| Compound 505 | (structure: 3-methylphenyl-SO2-NH-CH(CH3)-[4-ethyl-5-(2,2,2-trifluoroethoxy)-4H-1,2,4-triazol-3-yl], CHIRAL) | 138.0-139.0 |
| Compound 506 | (structure: 4-chlorophenyl-SO2-NH-CH(CH3)-CH(OH)-[4-ethyl-5-methoxy-4H-1,2,4-triazol-3-yl], CHIRAL) | 168.0-169.0 |

TABLE 1-continued

| Compound 507 | (structure) | 141.0-143.0 |
| Compound 508 | (structure) | 152.0-153.0 |
| Compound 509 | (structure) | 123.0-124.5 |
| Compound 510 | (structure) | 177.0-178.0 |
| Compound 511 | (structure) | 166.0-167.0 |
| Compound 512 | (structure) | 109.0-110.0 |
| Compound 513 | (structure) | 162.5-163.5 |

TABLE 1-continued
| Compound | Structure | mp (°C) / NMR |
|---|---|---|
| Compound 514 | 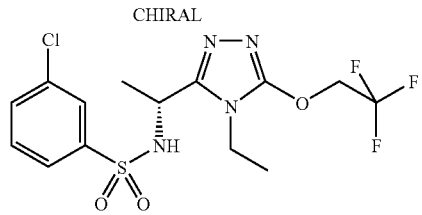 | 119.0-119.5 |
| Compound 515 | 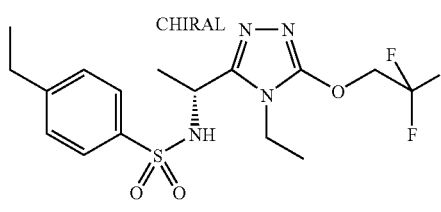 | 138.5-139.5 |
| Compound 516 | 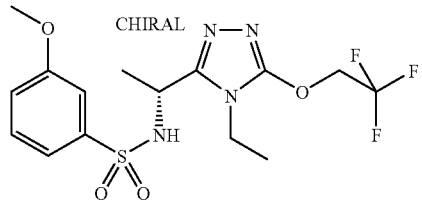 | 109.5-110.0 |
| Compound 517 | 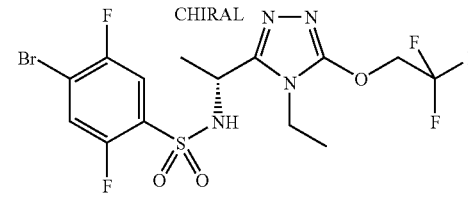 | 126.0-127.0 |
| Compound 518 | 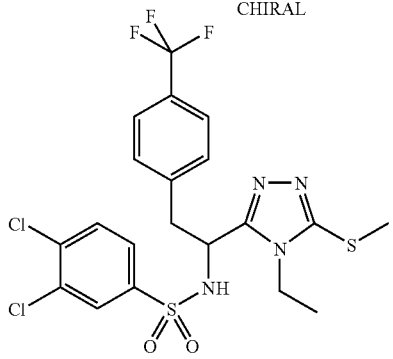 | 215.0-218.0 |
| Compound 519 | 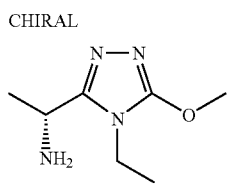 | (300 MHz, CDCl3) δ ppm: 1.32 (t, J = 7.2 Hz, 3H), 1.54 (d, J = 6.8 Hz, 3H), 3.78-3.98 (m, 2H), 4.03-4.20 (m, 1H), 4.13 (s, 3H) |
| Compound 520 | 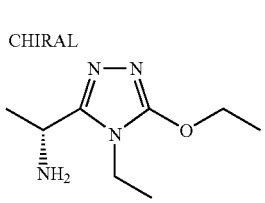 | (300 MHz, CDCl3) δ ppm: 1.31 (t, J = 7.2 Hz, 3H), 1.44 (d, J = 7.1 Hz, 3H), 1.54 (d, J = 6.7 Hz, 3H), 1.65 (bs, 2H), 3.80-3.97 (m, 2H), 4.08 (q, J = 6.7 Hz, 1H), 4.51 (q, J = 7.2 Hz, 2H) |

TABLE 1-continued
| Compound 521 | 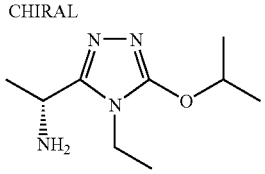 | | (300 MHz, CDCl3) δ ppm: 1.30 (t, J = 7.2 Hz, 3H), 1.41 (d, J = 6.1 Hz, 6H), 1.58 (d, J = 6.7 Hz, 3H), 3.79-3.91 (m, 2H), 4.10-4.22 (m, 1H), 5.07-5.29 (m, 1H) |
|---|---|---|---|
| Compound 522 | 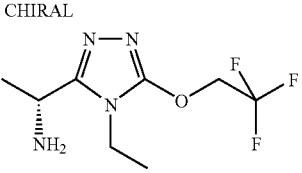 | | (300 MHz, CDCl3) δ ppm: 1.35 (t, J = 7.2 Hz, 3H), 1.57 (d, J = 6.7 Hz, 3H), 3.87-4.07 (m, 2H), 4.11 (q, J = 6.7, 1H), 4.84 (q, J = 8.1, 2H) |
| Compound 523 | 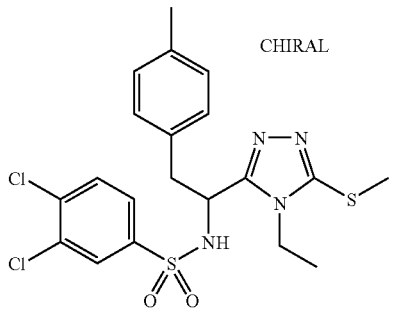 | 194.5-195.5 | |
| Compound 524 | 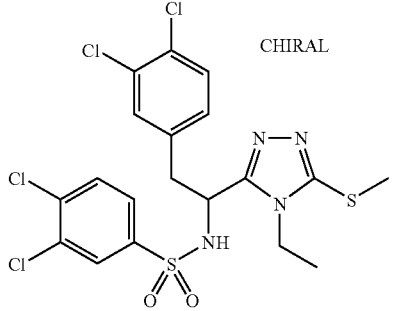 | 240.5-242.5 | |
| Compound 525 | 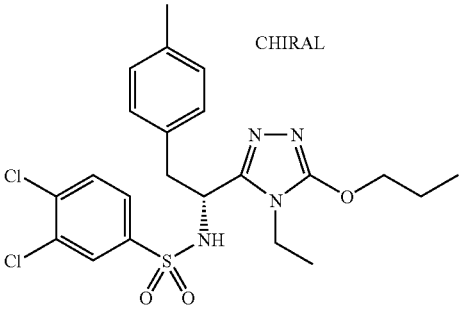 | 196.5-198.5 | |
| Compound 526 | 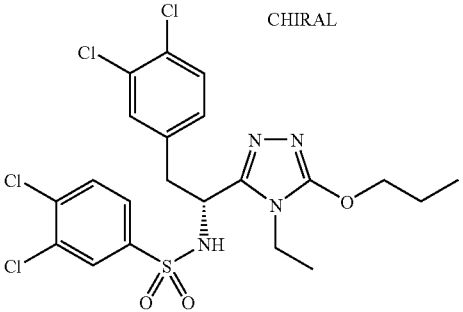 | 232.5-234.5 | |

| | | |
|---|---|---|
| Compound 527 | 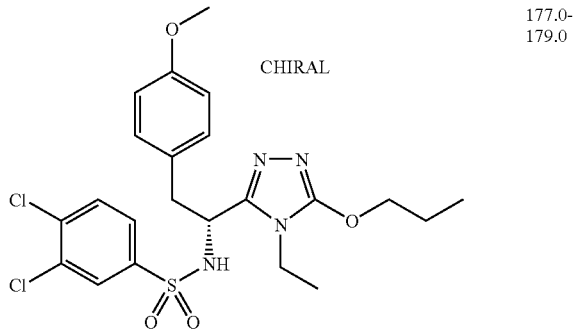 | 177.0-179.0 |
| Compound 528 | 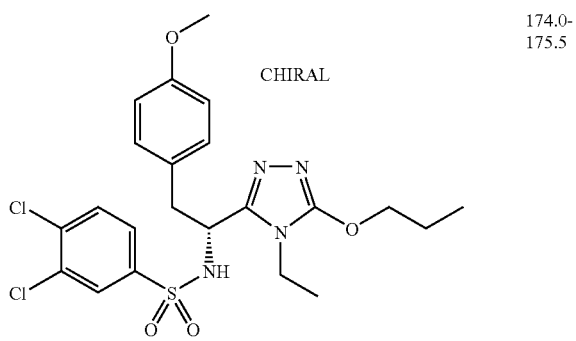 | 174.0-175.5 |
| Compound 529 | 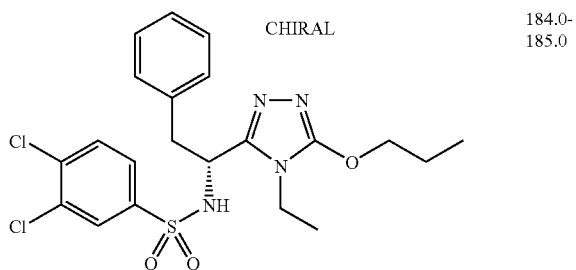 | 184.0-185.0 |
| Compound 530 | 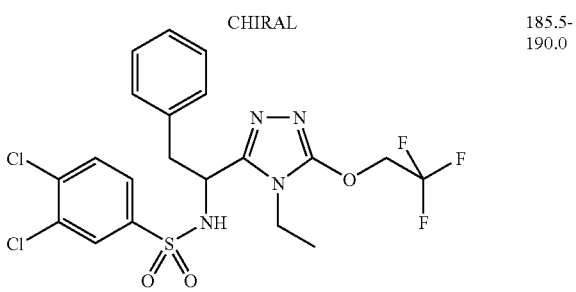 | 185.5-190.0 |
| Compound 531 | 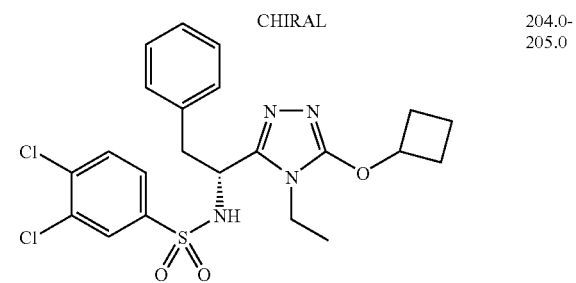 | 204.0-205.0 |

| | | | |
|---|---|---|---|
| Compound 532 | | 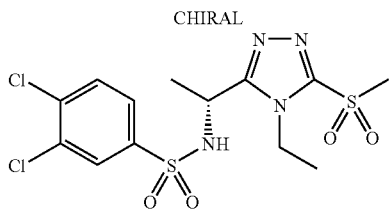 | 104.0-107.0 |
| Compound 533 | | 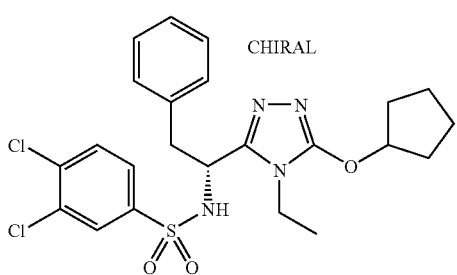 | 188.0-189.0 |
| Compound 534 | | 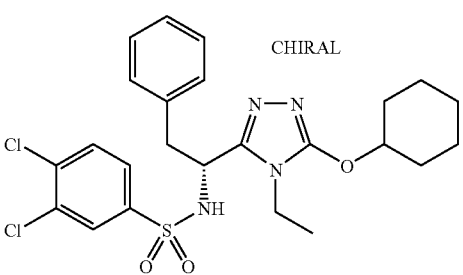 | 192.0-193.0 |
| Compound 535 | | 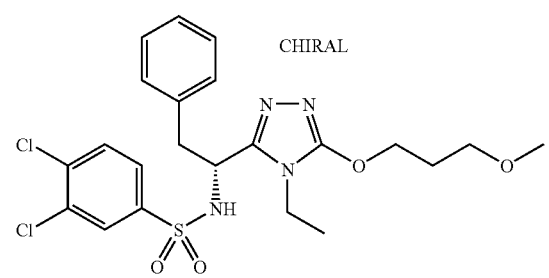 | 148.5-150.0 |
| Compound 536 | | 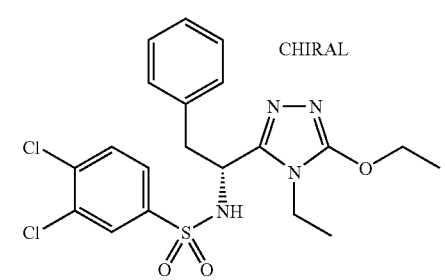 | 160.0-162.0 |
| Compound 537 | | 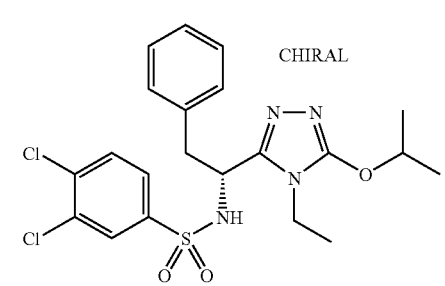 | 176.0-178.0 |

TABLE 1-continued
| Compound 538 | 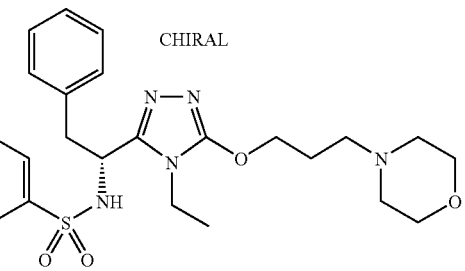 | 120.5-123 | |
| --- | --- | --- | --- |
| Compound 539 | 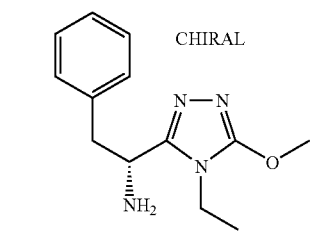 | | (200 MHz, CDCl3) δ ppm: 1.18 (t, J = 7.3 Hz, 3H), 3.06 (dd, J = 13.4, 8.6 Hz, 1H), 3.33 (dd, J = 13.4, 5.7 Hz, 1H), 3.55-3.90 (m, 2H), 4.07 (dd, J = 8.6, 5.7 Hz, 1H), 4.13 (s, 3H), 7.10-7.38 (m, 5H) |
| Compound 540 | 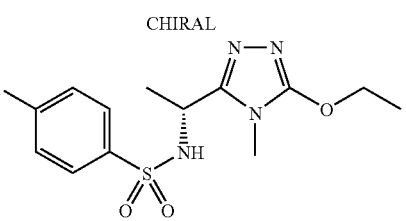 | 187.5-188.0 | |
| Compound 541 | 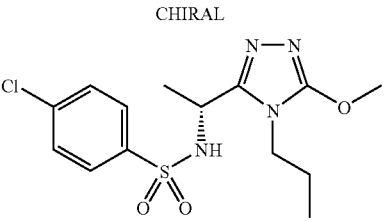 | 141.5-142.0 | |
| Compound 542 | 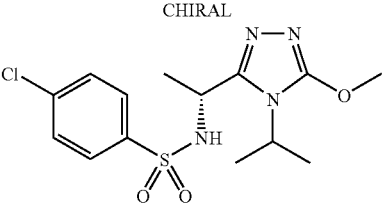 | 178.0-180.0 | |
| Compound 543 | 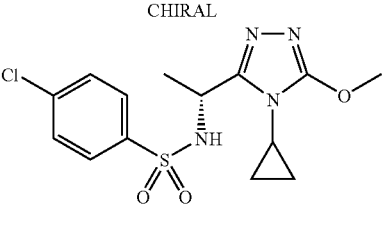 | 183.0-184.0 | |
| Compound 544 | 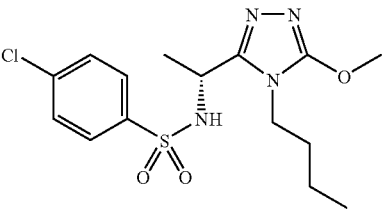 | 118.5-120.0 | |

| | | |
|---|---|---|
| Compound 545 | 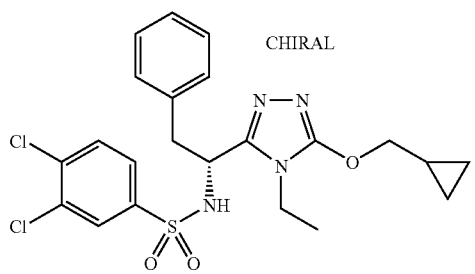 CHIRAL | 185.0-189.0 |
| Compound 546 | 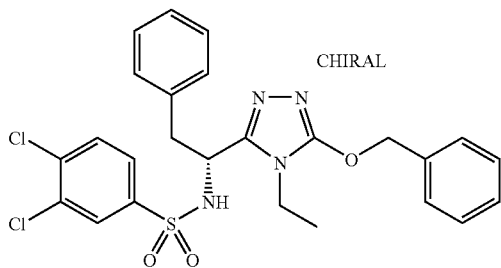 CHIRAL | 164.5-165.5 |
| Compound 547 | 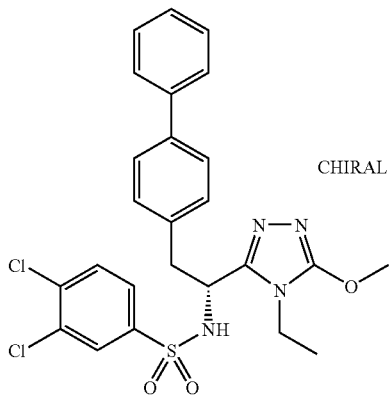 CHIRAL | 181.0-185.0 |
| Compound 548 | 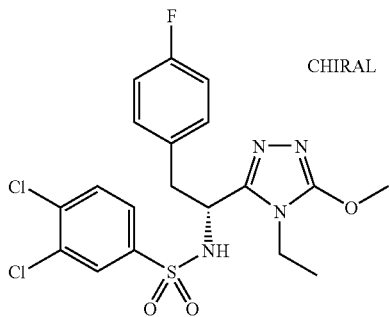 CHIRAL | 177.0-179.5 |
| Compound 549 | 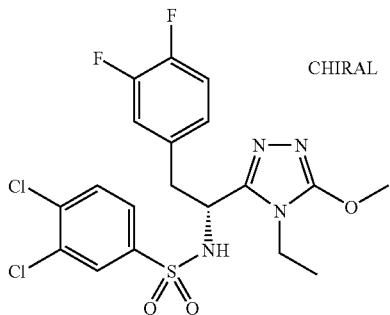 CHIRAL | 206.0-207.5 |

TABLE 1-continued

| Compound 550 | (structure) | CHIRAL | 143.0-144.5 |
| Compound 551 | (structure) | CHIRAL | 181.5-183.0 |
| Compound 552 | (structure) | CHIRAL | 191.0-196.0 |
| Compound 553 | (structure) | CHIRAL | 229.0-230.0 |
| Compound 554 | (structure) | CHIRAL | 236.0-237.0 |

TABLE 1-continued

| Compound 555 | 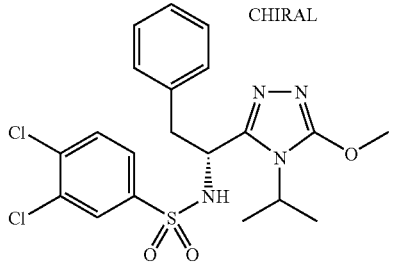 CHIRAL | (600 MHz, CDCl3) δ ppm: 0.90 (d, J = 6.9 Hz, 3H), 1.27 (d, J = 7.8 Hz, 3H), 3.08-3.28 (m, 2H), 3.87-4.01 (m, 1H), 4.09 (s, 3H), 4.54-4.64 (m, 1H), 6.97-7.05 (m, 2H), 7.14-7.21 (m, 3H), 7.48 (d, J = 8.3 Hz, 1H), 7.56-7.67 (m, 1H), 7.75-7.83 (m, 1H) |
|---|---|---|
| Compound 556 | 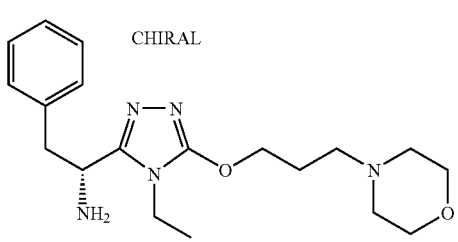 CHIRAL | (600 MHz, DMSO-d6) δ ppm: 1.10 (t, J = 7.1 Hz, 3H), 1.83-1.95 (m, 2H), 2.29-2.43 (m, 4H), 2.39 (t, J = 7.1 Hz, 2H), 2.94 (dd, J = 13.3, 7.3 Hz, 1H), 3.16 (dd, J = 13.3, 6.9 Hz, 1H), 3.50-3.62 (m, 4H), 3.65-3.83 (m, 2H), 3.97-4.06 (m, 1H), 4.35 (t, J = 6.6 Hz, 2H), 7.12-7.30 (m, 5H) |
| Compound 557 | 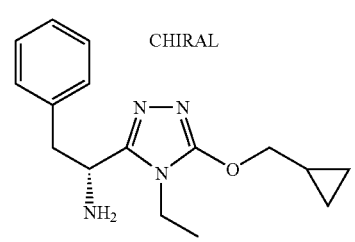 CHIRAL | (600 MHz, CDCl3) δ ppm: 0.30-0.36 (m, 2H), 0.55-0.61 (m, 2H), 1.17 (t, J = 7.3 Hz, 3H), 1.24-1.34 (m, 1H), 3.02 (dd, J = 13.3, 8.7 Hz, 1H), 3.29 (dd, J = 13.3, 5.7 Hz, 1H), 3.63-3.82 (m, 2H), 4.02 (dd, J = 8.7, 5.7 Hz, 1H), 4.21-4.25 (m, 2H), 7.14-7.30 (m, 5H) |
| Compound 558 | 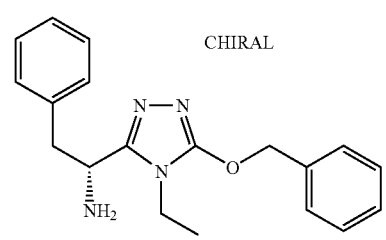 CHIRAL | (200 MHz, CDCl3) δ ppm: 1.17 (t, J = 7.0 Hz, 3H), 2.96-3.41 (m, 2H), 3.53-4.24 (m, 3H), 5.47 (s, 2H), 7.07-7.58 (m, 10H) |
| Compound 559 | 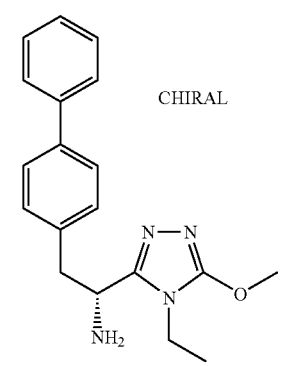 CHIRAL | (600 MHz, DMSO-d6) δ ppm: 1.13 (t, J = 7.3 Hz, 3H), 3.00 (dd, J = 13.5, 7.6 Hz, 1H), 3.22 (dd, J = 13.5, 6.6 Hz, 1H), 3.67-3.89 (m, 2H), 3.99 (s, 3H), 4.08-4.10 (m, 1H), 7.27-7.39 (m, 3H), 7.41-7.49 (m, 2H), 7.53-7.60 (m, 2H), 7.60-7.70 (m, 2H) |
| Compound 560 | 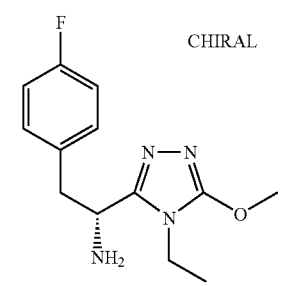 CHIRAL | (600 MHz, DMSO-d6) δ ppm: 1.11 (t, J = 7.1 Hz, 3H), 2.94 (dd, J = 13.4, 7.6 Hz, 1H), 3.15 (dd, J = 13.4, 6.9 Hz, 1H), 3.67-3.85 (m, 2H), 3.97-4.03 (m, 1H), 3.99 (s, 3H), 6.99-7.12 (m, 2H), 7.18-7.30 (m, 2H) |

TABLE 1-continued

| Compound 561 | (structure: 3,4-difluorobenzyl, CHIRAL, 4-ethyl-5-methoxy-4H-1,2,4-triazol-3-yl, NH₂) | (600 MHz, DMSO-d6) δ ppm: 1.14 (t, J = 7.3 Hz, 3H), 2.95 (dd, J = 13.6, 7.8 Hz, 1H), 3.17 (dd, J = 13.6, 6.4 Hz, 1H), 3.71-3.88 (m, 2H), 3.97-4.04 (m, 1H), 3.99 (s, 3H), 7.03-7.11 (m, 1H), 7.26-7.37 (m, 2H) |
|---|---|---|
| Compound 562 | (structure: 2-fluorobenzyl, CHIRAL, 4-ethyl-5-methoxy-4H-1,2,4-triazol-3-yl, NH₂) | (600 MHz, DMSO-d6) δ ppm: 1.14 (t, J = 7.1 Hz, 3H), 3.00 (dd, J = 13.6, 7.8 Hz, 1H), 3.18 (dd, J = 13.6, 6.4 Hz, 1H), 3.71-3.79 (m, 1H), 3.80-3.89 (m, 1H), 3.99 (s, 3H), 4.04-4.08 (m, 1H), 7.03-7.16 (m, 2H), 7.21-7.28 (m, 1H), 7.27-7.33 (m, 1H) |
| Compound 563 | (structure: 3-fluorobenzyl, CHIRAL, 4-ethyl-5-methoxy-4H-1,2,4-triazol-3-yl, NH₂) | (600 MHz, CDCl3) δ ppm: 1.21 (t, J = 7.1 Hz, 3H), 3.07 (dd, J = 13.4, 8.7 Hz, 1H), 3.35 (dd, J = 13.4, 5.7 Hz, 1H), 3.67-3.86 (m, 2H), 4.02-4.09 (m, 1H), 4.13 (s, 3H), 6.90-6.96 (m, 2H), 6.97-7.01 (m, 1H), 7.23-7.30 (m, 1H) |
| Compound 564 | (structure: 3,5-difluorobenzyl, CHIRAL, 4-ethyl-5-methoxy-4H-1,2,4-triazol-3-yl, NH₂) | (600 MHz, CDCl3) δ ppm: 1.24 (t, J = 7.1 Hz, 3H), 3.06 (dd, J = 13.7, 8.3 Hz, 1H), 3.37 (dd, J = 13.7, 5.7 Hz, 1H), 3.71-3.80 (m, 1H), 3.81-3.89 (m, 1H), 4.01-4.07 (m, 1H), 4.14 (s, 3H), 6.66-6.71 (m, 1H), 6.74-6.80 (m, 2H) |
| Compound 565 | (structure: benzyl, CHIRAL, 4-methyl-5-methoxy-4H-1,2,4-triazol-3-yl, NH₂) | (600 MHz, CDCl3) δ ppm: 3.06 (dd, J = 13.4 Hz, 1H), 3.18 (s, 3H), 3.24 (dd, J = 13.4, 6.0 Hz, 1H), 4.05-4.14 (m, 1H), 4.11 (s, 3H), 7.13-7.33 (m, 5H) |
| Compound 566 | (structure: benzyl, CHIRAL, 4-propyl-5-methoxy-4H-1,2,4-triazol-3-yl, NH₂) | (600 MHz, CDCl3) δ ppm: 0.83 (t, J = 7.6 Hz, 3H), 1.47-1.80 (m, 2H), 3.07 (dd, J = 13.5, 8.3 Hz, 1H), 3.31 (dd, J = 13.5, 6.0 Hz, 1H), 3.44-3.53 (m, 1H), 3.60-3.68 (m, 1H), 4.01 (dd, J = 8.3, 6.0 Hz, 1H), 4.11 (s, 3H), 7.14-7.33 (m, 5H) |

TABLE 1-continued

| Compound | Structure | NMR |
|---|---|---|
| Compound 567 | CHIRAL; (S)-1-(4-isopropyl-5-methoxy-4H-1,2,4-triazol-3-yl)-2-phenylethanamine | (600 MHz, CDCl3) δ ppm: 1.25 (d, J = 6.9 Hz, 3H), 1.39 (d, J = 6.9 Hz, 3H), 3.04 (dd, J = 13.6, 8.9 Hz, 1H), 3.28 (dd, J = 13.6, 5.5 Hz, 1H), 4.11 (s, 3H), 4.21-4.29 (m, 1H), 7.15-7.38 (m, 5H) |
| Compound 568 | CHIRAL; (S)-1-(4-cyclopropyl-5-methoxy-4H-1,2,4-triazol-3-yl)-2-phenylethanamine | (600 MHz, CDCl3) δ ppm: 0.65-0.75 (m, 1H), 0.86-0.98 (m, 3H), 2.33-2.42 (m, 1H), 3.10 (dd, J = 13.3, 7.8 Hz, 1H), 3.24 (dd, J = 13.3, 6.9 Hz, 1H), 4.09 (s, 3H), 4.21-4.29 (m, 1H), 7.11-7.32 (m, 5H) |

Inhibition rate (%) = [1 − (A − C) / (B − C)] × 100

| Compound No. | ESI MS (M + H)+ | ESI MS (M − H)− | APCI MS (M − H)− | Cell system binding test % inhibition (10 μM) | Membrane system binding test % inhibition (10 μM) |
|---|---|---|---|---|---|
| Compound 1 | 361 | 359 | | 89.8 | 72.3 |
| Compound 2 | 389 | 387 | | 88.5 | 100.6 |
| Compound 3 | 387 | 385 | | 86.1 | 89.1 |
| Compound 4 | 385 | 383 | | 86.8 | 101.4 |
| Compound 5 | 437 | | 435 | 97.2 | 81.2 |
| Compound 6 | 513 | | | 94.3 | 99.0 |
| Compound 7 | 462 | 460 | 460 | 88.5 | 74.6 |
| Compound 8 | 429 | 427 | | 83.9 | 85.6 |
| Compound 9 | 415 | 413 | 413 | 90.1 | 86.7 |
| Compound 10 | 401 | 399 | 399 | 85.6 | 54.3 |
| Compound 11 | 455 | | | 85.5 | 45.1 |
| Compound 12 | | | 509 | 87.8 | 85.9 |
| Compound 13 | | 429 | 429 | 80.8 | 43.6 |
| Compound 14 | 401 | 399 | | 87.0 | 69.6 |
| Compound 15 | 457 | 455 | | 91.0 | 79.4 |
| Compound 16 | 405 | 403 | 403 | 92.1 | 64.4 |
| Compound 17 | 413 | | | 85.5 | 90.6 |
| Compound 18 | 489 | | | 84.8 | 100.4 |
| Compound 19 | 485 | 483 | | 82.5 | 100.3 |
| Compound 20 | 445 | 443 | | 84.3 | 74.3 |
| Compound 21 | 401 | 399 | | 82.2 | 74.8 |
| Compound 22 | | | 449 | 82.1 | 96.9 |
| Compound 23 | 467 | 465 | 465 | 84.4 | 95.0 |
| Compound 24 | 419 | 417 | 417 | 82.6 | 60.6 |
| Compound 25 | 443 | 441 | 441 | 81.5 | 77.8 |
| Compound 26 | 421 | | | 84.0 | 61.1 |

TABLE 1-continued

| | | | | | |
|---|---|---|---|---|---|
| Compound 27 | 399 | 397 | | 86.9 | 76.0 |
| Compound 28 | 415 | | | 93.1 | 82.8 |
| Compound 29 | | | 401 | 93.0 | 95.9 |
| Compound 30 | 459 | | | 91.9 | 100.5 |
| Compound 31 | 417 | 415 | 415 | 90.2 | 90.0 |
| Compound 32 | 451 | 449 | 449 | 89.1 | 99.1 |
| Compound 33 | | | 401 | 91.7 | 90.0 |
| Compound 34 | | | 413 | 91.5 | 76.4 |
| Compound 35 | 471 | 469 | 469 | 91.9 | 87.7 |
| Compound 36 | | | 475 | 89.5 | 103.9 |
| Compound 37 | | | 479 | 92.7 | 92.8 |
| Compound 38 | 463 | | 461 | 91.5 | 81.0 |
| Compound 39 | | | 463 | 93.8 | 86.7 |
| Compound 40 | 513 | | 511 | 87.0 | 46.1 |
| Compound 41 | | | 449 | 87.3 | 97.3 |
| Compound 42 | | | 469 | 85.4 | 98.8 |
| Compound 43 | 505 | | 503 | 90.5 | 102.4 |
| Compound 44 | | | 469 | 93.0 | 99.6 |
| Compound 45 | | | 469 | 91.7 | 91.3 |
| Compound 46 | | | 503 | 90.4 | 99.5 |
| Compound 47 | 465 | | 463 | 92.5 | 99.2 |
| Compound 48 | 487 | | 485 | 93.0 | 101.3 |
| Compound 49 | | | 415 | 94.8 | 93.9 |
| Compound 50 | 507 | | 505 | 95.3 | 96.2 |
| Compound 51 | 463 | | 461 | 91.2 | 93.0 |
| Compound 52 | 495 | | 493 | 93.6 | 89.1 |
| Compound 53 | 375 | | 373 | 90.8 | 89.3 |
| Compound 54 | 389 | | 387 | 88.7 | 105.4 |
| Compound 55 | 401 | 399 | | 94.3 | 104.0 |
| Compound 56 | 462 | | 480 | 87.1 | 91.0 |
| Compound 57 | 411 | | | 92.6 | 100.5 |
| Compound 58 | 495 | | | 91.9 | 98.1 |
| Compound 59 | 451 | | | 93.2 | 96.9 |
| Compound 60 | 483 | | | 90.3 | 97.2 |
| Compound 61 | | | 449 | 95.0 | 98.9 |
| Compound 62 | | | 450 | 92.9 | 90.6 |
| Compound 63 | | | 436 | 93.7 | 99.7 |
| Compound 64 | | | 436 | 91.3 | 86.5 |
| Compound 65 | 458 | 456 | 456 | 83.3 | 83.1 |
| Compound 66 | 474 | 472 | 472 | 84.0 | 90.6 |
| Compound 67 | | | 430 | 73.8 | 42.2 |
| Compound 68 | 466 | 464 | 464 | 93.0 | 97.9 |
| Compound 69 | 452 | 450 | 450 | 89.5 | 92.7 |

TABLE 1-continued

| Compound | | | | | |
|---|---|---|---|---|---|
| Compound 70 | | | 442 | 88.4 | 98.0 |
| Compound 71 | 480 | | 478 | 89.7 | 104.4 |
| Compound 72 | 534 | 532 | | 89.8 | 95.8 |
| Compound 73 | | | 457 | 93.9 | 98.4 |
| Compound 74 | 495 | 493 | 493 | 93.6 | 109.3 |
| Compound 75 | 494 | | 492 | 92.7 | 99.4 |
| Compound 76 | | | 470 | 97.3 | 101.0 |
| Compound 77 | 494 | | | 89.4 | 96.4 |
| Compound 78 | 458 | 456 | 456 | 83.0 | 96.5 |
| Compound 79 | | | 470 | 84.7 | 94.9 |
| Compound 80 | 515 | | 513 | 86.2 | 87.5 |
| Compound 81 | 482 | | 480 | 87.6 | 110.4 |
| Compound 82 | | | 492 | 84.7 | 90.4 |
| Compound 83 | | | 402 | 85.6 | 99.5 |
| Compound 84 | 441 | | 439 | 87.9 | 100.4 |
| Compound 85 | | | 488 | 90.4 | 106.0 |
| Compound 86 | 509 | 507 | 507 | 93.4 | 110.3 |
| Compound 87 | 431 | 429 | 429 | 82.7 | 84.7 |
| Compound 88 | 431 | 429 | 429 | 87.6 | 97.1 |
| Compound 89 | | | | 89.3 | |
| Compound 90 | | 345 | | 60.6 | 48.8 |
| Compound 91 | | 371 | | 72.9 | 47.4 |
| Compound 92 | | 371 | | 88.3 | |
| Compound 93 | | 331 | | | |
| Compound 94 | | 331 | | | |
| Compound 95 | 401 | 399 | | 94.0 | 60.2 |
| Compound 96 | | 359 | | | |
| Compound 97 | | 399 | | 88.9 | 52.5 |
| Compound 98 | 381 | 359 | | | |
| Compound 99 | 401 | | | 75.8 | 57.4 |
| Compound 100 | | 385 | | | |
| Compound 101 | | 345 | | | |
| Compound 102 | | 357 | | | |
| Compound 103 | | 317 | | | |
| Compound 104 | | | | 99.5 | 42.1 |
| Compound 105 | | 385 | | 71.5 | |
| Compound 106 | 387 | 385 | | 86.9 | 52.5 |
| Compound 107 | | 345 | | | |
| Compound 108 | | 345 | | | |
| Compound 109 | | 399 | | 93.0 | 100.2 |
| Compound 110 | | | | 90.1 | 88.0 |
| Compound 111 | | 359 | | | |
| Compound 112 | | 359 | | | |

TABLE 1-continued

| | | | | |
|---|---|---|---|---|
| Compound 113 | | 413 | 84.0 | 46.3 |
| Compound 114 | | | 90.6 | 74.5 |
| Compound 115 | | 373 | | |
| Compound 116 | 375 | 373 | | |
| Compound 117 | 415 | 413 | 93.6 | 83.8 |
| Compound 118 | 375 | 373 | | |
| Compound 119 | | 439 | | |
| Compound 120 | | 399 | | |
| Compound 121 | | 461 | | |
| Compound 122 | | 421 | | |
| Compound 123 | | 453 | | |
| Compound 124 | | | | |
| Compound 125 | 401 | 399 | 69.0 | 52.4 |
| Compound 126 | | 449 | 77.0 | |
| Compound 127 | 465 | 463 | 63.6 | |
| Compound 128 | 361 | 359 | | |
| Compound 129 | | 399 | | |
| Compound 130 | 361 | 359 | | |
| Compound 131 | | 433 | | |
| Compound 132 | | 393 | | |
| Compound 133 | 449 | 447 | | |
| Compound 134 | 449 | 447 | 88.8 | 84.8 |
| Compound 135 | | | 86.7 | 96.9 |
| Compound 136 | | | 102.7 | 94.7 |
| Compound 137 | | | 99.0 | 57.1 |
| Compound 138 | 463 | 461 | 94.7 | 102.1 |
| Compound 139 | | | 91.0 | 107.2 |
| Compound 140 | | 421 | | |
| Compound 141 | 477 | 475 | 94.8 | 79.5 |
| Compound 142 | | 435 | | |
| Compound 143 | 477 | 475 | 96.0 | 88.7 |
| Compound 144 | | 435 | | |
| Compound 145 | | | 46.0 | |
| Compound 146 | 451 | 449 | | |
| Compound 147 | | 489 | 75.2 | |
| Compound 148 | 451 | 449 | | |
| Compound 149 | 491 | 489 | 63.4 | |
| Compound 150 | 451 | 449 | | |
| Compound 151 | 493 | 491 | 41.6 | |
| Compound 152 | | 451 | | |
| Compound 153 | | 546 | 26.8 | |
| Compound 154 | 508 | 506 | | |
| Compound 155 | 545 | 544 | | |

TABLE 1-continued

| | | | | | |
|---|---|---|---|---|---|
| Compound 156 | 506 | 504 | | | |
| Compound 157 | 548 | 548 | | | |
| Compound 158 | 508 | 506 | | | |
| Compound 159 | | 491 | | | |
| Compound 160 | | 451 | | | |
| Compound 161 | 499 | 497 | | | |
| Compound 162 | | 523 | | | |
| Compound 163 | | | | | |
| Compound 164 | | 501 | | 40.4 | |
| Compound 165 | 463 | 461 | | | |
| Compound 166 | | | | | |
| Compound 167 | | 469 | | | |
| Compound 168 | 433 | 431 | | | |
| Compound 169 | 447 | 445 | | 67.5 | 72.9 |
| Compound 170 | 495 | 493 | | | |
| Compound 171 | 367 | 365 | | | |
| Compound 172 | | 383 | | | |
| Compound 173 | | 343 | | | |
| Compound 174 | | 397 | | | |
| Compound 175 | | | | | |
| Compound 176 | 413 | 411 | | | |
| Compound 177 | | | | | |
| Compound 178 | 427 | 425 | | | |
| Compound 179 | | | | | |
| Compound 180 | 377 | 375 | | 48.9 | |
| Compound 181 | 377 | 375 | | | |
| Compound 182 | | 391 | | 53.7 | |
| Compound 183 | 373 | 371 | 373 | 89.2 | 97.7 |
| Compound 184 | | 371 | 373 | | 44.4 |
| Compound 185 | 345 | 343 | | 87.4 | 86.6 |
| Compound 186 | 359 | 357 | | 89.3 | 94.5 |
| Compound 187 | | 400 | | 82.9 | 46.4 |
| Compound 188 | 416 | 414 | | 82.0 | 46.3 |
| Compound 189 | 458 | 456 | | 105.3 | 107.2 |
| Compound 190 | 375 | 373 | | 91.1 | 41.3 |
| Compound 191 | 389 | 387 | | 97.1 | 88.3 |
| Compound 192 | 555 | 553 | | 75.5 | 105.3 |
| Compound 193 | 345 | 343 | | 108.0 | 64.4 |
| Compound 194 | 345 | 343 | | 85.6 | |
| Compound 195 | 369 | 367 | | 103.1 | 91.2 |
| Compound 196 | 353 | 351 | | 105.7 | 88.5 |
| Compound 197 | 329 | 327 | | | |
| Compound 198 | | 366 | 366 | 92.5 | 46.7 |

TABLE 1-continued

| | | | | | |
|---|---|---|---|---|---|
| Compound 199 | 353 | 351 | 351 | 93.0 | 54.9 |
| Compound 200 | | | 387 | 97.4 | 93.3 |
| Compound 201 | | | 365 | 92.6 | 45.3 |
| Compound 202 | | | 289 | 96.6 | 60.3 |
| Compound 203 | | | 471 | 97.9 | 88.3 |
| Compound 204 | | | 387 | 97.8 | 45.4 |
| Compound 205 | | | 381 | 99.6 | 47.4 |
| Compound 206 | | | 387 | 102.7 | 86.2 |
| Compound 207 | | 365 | 365 | 95.8 | 43.5 |
| Compound 208 | | | 393 | 99.9 | 93.0 |
| Compound 209 | | | 388 | 91.4 | 103.7 |
| Compound 210 | | | 309 | 91.8 | 46.6 |
| Compound 211 | | | 400 | 93.9 | 46.9 |
| Compound 212 | | | 334 | 92.4 | 45.6 |
| Compound 213 | | | 334 | 96.2 | 66.1 |
| Compound 214 | | | 413 | 96.8 | 59.3 |
| Compound 215 | | | 357 | 98.3 | 94.4 |
| Compound 216 | | 393 | | 97.2 | 63.7 |
| Compound 217 | | | 383 | 97.4 | 62.3 |
| Compound 218 | | 402 | 402 | 101.1 | 40.2 |
| Compound 219 | | | 377 | 95.9 | |
| Compound 220 | | | 383 | 97.2 | 98.0 |
| Compound 221 | | | 369 | 89.9 | 56.1 |
| Compound 222 | | 337 | 337 | 92.9 | 71.8 |
| Compound 223 | | | 327 | 95.5 | 70.4 |
| Compound 224 | 277 | 275 | 275 | 92.2 | 54.5 |
| Compound 225 | | | 351 | 94.0 | |
| Compound 226 | | | 339 | 92.3 | 42.4 |
| Compound 227 | 249 | | 247 | 92.6 | 52.0 |
| Compound 228 | | | 387 | 93.9 | |
| Compound 229 | | | 359 | 102.5 | 61.1 |
| Compound 230 | | | 359 | 102.6 | 102.5 |
| Compound 231 | | | 354 | 96.6 | 40.3 |
| Compound 232 | | | 354 | | |
| Compound 233 | | | 354 | 99.8 | 93.2 |
| Compound 234 | | 368 | 388 | 90.9 | |
| Compound 235 | | | 387 | 110.6 | 63.8 |
| Compound 236 | | | 345 | 98.9 | |
| Compound 237 | | 399 | 399 | 95.4 | 52.5 |
| Compound 238 | | | 435 | 99.1 | 79.1 |
| Compound 239 | 277 | 275 | 275 | 92.7 | |
| Compound 240 | 362 | 360 | 360 | 93.4 | 70.3 |
| Compound 241 | | | 335 | 101.5 | 80.5 |

TABLE 1-continued

| Compound | | | | | |
|---|---|---|---|---|---|
| Compound 242 | 317 | 315 | 315 | 100.1 | 49.9 |
| Compound 243 | | | 323 | 101.6 | 66.0 |
| Compound 244 | | | 323 | 92.3 | |
| Compound 245 | | | 377 | 96.8 | 87.7 |
| Compound 246 | | | 323 | 98.1 | 61.8 |
| Compound 247 | | | 393 | 95.3 | 52.0 |
| Compound 248 | | | 323 | 99.5 | 83.3 |
| Compound 249 | | | 377 | 100.6 | 86.3 |
| Compound 250 | | 455 | 455 | 88.7 | 42.9 |
| Compound 251 | | | 422 | 102.1 | 105.5 |
| Compound 252 | | | 427 | 102.9 | 100.0 |
| Compound 253 | | | 361 | 83.4 | |
| Compound 254 | 330 | 328 | 328 | 84.6 | |
| Compound 255 | | 373 | 373 | 96.3 | 48.3 |
| Compound 256 | | 357 | 357 | 95.6 | |
| Compound 257 | | 371 | 371 | 95.7 | 58.1 |
| Compound 258 | | | 341 | 89.8 | |
| Compound 259 | | | 367 | 86.8 | |
| Compound 260 | | | 377 | 89.4 | 46.9 |
| Compound 261 | | | 385 | 94.5 | 56.7 |
| Compound 262 | | | 351 | 96.5 | 68.8 |
| Compound 263 | | | | | |
| Compound 264 | | | 353 | 95.8 | 42.7 |
| Compound 265 | | | 445 | 98.2 | 69.5 |
| Compound 266 | | | 377 | 97.0 | 83.0 |
| Compound 267 | | | 357 | 99.9 | 89.4 |
| Compound 268 | | | 361 | 98.7 | 88.6 |
| Compound 269 | | | 339 | 96.3 | 74.5 |
| Compound 270 | | | 423 | 94.8 | 61.3 |
| Compound 271 | | | 379 | 89.6 | |
| Compound 272 | | 465 | 465 | 101.7 | 94.3 |
| Compound 273 | | | 353 | 94.3 | 68.4 |
| Compound 274 | | | 377 | 102.2 | 103.5 |
| Compound 275 | | | 393 | 99.4 | 71.9 |
| Compound 276 | | | 393 | 88.9 | |
| Compound 277 | | | 334 | 99.7 | 51.4 |
| Compound 278 | | | 401 | 70.9 | |
| Compound 279 | | | 345 | 100.8 | |
| Compound 280 | | | 327 | 91.0 | |
| Compound 281 | | | | | 75.5 |
| Compound 282 | | 351 | 351 | 92.7 | 48.1 |
| Compound 283 | | | 435 | 73.9 | |
| Compound 284 | | | 379 | 88.0 | 41.5 |

TABLE 1-continued

| | | | | | |
|---|---|---|---|---|---|
| Compound 285 | 365 | 363 | 363 | 97.1 | 63.9 |
| Compound 286 | | | 345 | 97.5 | 57.4 |
| Compound 287 | | | 345 | 100.3 | 80.1 |
| Compound 288 | | | 405 | 103.0 | 54.9 |
| Compound 289 | | | 379 | 101.7 | 63.6 |
| Compound 290 | | 423 | 423 | 99.9 | 86.0 |
| Compound 291 | | | 379 | 97.8 | 77.6 |
| Compound 292 | | | 391 | 96.7 | 51.4 |
| Compound 293 | | | 357 | 31.8 | |
| Compound 294 | | 341 | 341 | 64.5 | |
| Compound 295 | | | 391 | 66.1 | |
| Compound 296 | | | 391 | | |
| Compound 297 | | | 413 | 23.8 | |
| Compound 298 | | | 345 | 85.7 | |
| Compound 299 | | | 327 | 94.5 | 44.4 |
| Compound 300 | | | 373 | 95.0 | |
| Compound 301 | | | 395 | 78.3 | |
| Compound 302 | | | 383 | 98.7 | 57.7 |
| Compound 303 | | | 465 | 97.7 | 56.1 |
| Compound 304 | | | 368 | 79.8 | |
| Compound 305 | | | 357 | 86.5 | |
| Compound 306 | | | 465 | 94.5 | 62.8 |
| Compound 307 | | | 352 | 96.2 | 68.0 |
| Compound 308 | | | 337 | 95.5 | 68.1 |
| Compound 309 | | | 375 | 93.2 | 46.5 |
| Compound 310 | | | 375 | 98.5 | 78.8 |
| Compound 311 | 347 | | 345 | 97.6 | 52.4 |
| Compound 312 | | | 361 | 95.9 | 50.7 |
| Compound 313 | | | 363 | 100.5 | 93.2 |
| Compound 314 | | | 401 | 101.7 | 100.1 |
| Compound 315 | | | 341 | 100.1 | 85.0 |
| Compound 316 | | | 361 | 92.9 | |
| Compound 317 | | | 405 | 97.2 | 95.8 |
| Compound 318 | | | 397 | 68.5 | |
| Compound 319 | | | 337 | 93.4 | 89.9 |
| Compound 320 | | | 341 | 93.5 | 47.9 |
| Compound 321 | | | 395 | 100.4 | 99.7 |
| Compound 322 | | 361 | 361 | 95.9 | 43.5 |
| Compound 323 | 326 | | 324 | 64.4 | |
| Compound 324 | | | 431 | 88.1 | |
| Compound 325 | | 324 | 324 | 36.5 | |
| Compound 326 | | | 402 | | |
| Compound 327 | | | 402 | | |

TABLE 1-continued

| | | | | | |
|---|---|---|---|---|---|
| Compound 328 | | | 431 | | |
| Compound 329 | | 324 | 324 | 38.5 | |
| Compound 330 | | | 415 | | |
| Compound 331 | 408 | 406 | 406 | 23.9 | |
| Compound 332 | | | 339 | 35.5 | |
| Compound 333 | | 329 | 329 | 92.8 | |
| Compound 334 | | 373 | 373 | 54.7 | |
| Compound 335 | | | 367 | | |
| Compound 336 | | 314 | | 89.3 | |
| Compound 337 | | | 351 | 102.3 | 61.3 |
| Compound 338 | | | 367 | 103.0 | 69.4 |
| Compound 339 | | 344 | 344 | 92.1 | |
| Compound 340 | | | 367 | 77.5 | |
| Compound 341 | | | 367 | 99.4 | 99.4 |
| Compound 342 | | | 315 | 88.4 | |
| Compound 343 | | | 381 | 98.9 | 41.4 |
| Compound 344 | | | 380 | 101.8 | 65.8 |
| Compound 345 | | | 382 | 88.5 | |
| Compound 346 | | 376 | 376 | 38.5 | |
| Compound 347 | | | 458 | | |
| Compound 348 | | | 442 | | |
| Compound 349 | | 401 | 401 | | |
| Compound 350 | | | 402 | | |
| Compound 351 | | | 427 | | |
| Compound 352 | 427 | 425 | 425 | | |
| Compound 353 | | 423 | 423 | 23.3 | |
| Compound 354 | | | 471 | | |
| Compound 355 | | | 351 | 100.9 | 62.8 |
| Compound 356 | | | 410 | | |
| Compound 357 | | | 414 | 85.6 | |
| Compound 358 | | | 414 | 79.6 | |
| Compound 359 | | | 473 | | |
| Compound 360 | | | 378 | | |
| Compound 361 | | | 409 | | |
| Compound 362 | | | 415 | 28.2 | |
| Compound 363 | | 377 | 377 | 100.4 | |
| Compound 364 | | | 422 | 27.0 | |
| Compound 365 | | 350 | 360 | 81.7 | 41.8 |
| Compound 366 | | | 374 | | |
| Compound 367 | 345 | 343 | 343 | 97.0 | 41.8 |
| Compound 368 | | 355 | 365 | 101.7 | 85.1 |
| Compound 369 | | | 365 | 105.3 | 102.0 |
| Compound 370 | | | 385 | 32.3 | |

TABLE 1-continued

| | | | | | |
|---|---|---|---|---|---|
| Compound 371 | | | 455 | 102.2 | 61.2 |
| Compound 372 | | | 455 | 104.7 | 94.3 |
| Compound 373 | | 310 | 310 | 73.4 | |
| Compound 374 | 377 | 375 | | | |
| Compound 375 | | | | 92.6 | 54.3 |
| Compound 376 | | | | 90.7 | 57.3 |
| Compound 377 | | | | 97.9 | 90.3 |
| Compound 378 | | | | 103.3 | 87.2 |
| Compound 379 | | | | 99.7 | 93.4 |
| Compound 380 | | | | 104.7 | 85.2 |
| Compound 381 | | | | 97.1 | 94.9 |
| Compound 382 | | | | 97.8 | 99.6 |
| Compound 383 | | | | 82.2 | 66.0 |
| Compound 384 | | | | 104.1 | 93.5 |
| Compound 385 | | | | 99.9 | 90.1 |
| Compound 386 | | | | 103.0 | 99.5 |
| Compound 387 | | | | 101.8 | 99.3 |
| Compound 388 | | | | 104.4 | 103.3 |
| Compound 389 | | | | 96.3 | 89.6 |
| Compound 390 | | | | 101.3 | 99.8 |
| Compound 391 | | | | 92.5 | 78.3 |
| Compound 392 | | | | 95.6 | 85.1 |
| Compound 393 | | | | 82.4 | 65.3 |
| Compound 394 | | | | 82.9 | 76.9 |
| Compound 395 | | | | 91.9 | 83.7 |
| Compound 396 | | | | 87.9 | 83.3 |
| Compound 397 | | | | 88.6 | 92.0 |
| Compound 398 | | | | 85.8 | 93.5 |
| Compound 399 | | | | 88.5 | 90.9 |
| Compound 400 | | | | 92.8 | 84.8 |
| Compound 401 | | | | 92.8 | 87.2 |
| Compound 402 | | | | 90.4 | 95.8 |
| Compound 403 | | | | 86.1 | 85.9 |
| Compound 404 | | | | 91.2 | 90.0 |
| Compound 405 | | | | 90.4 | 88.2 |
| Compound 406 | | | | 90.1 | 92.5 |
| Compound 407 | | | | 94.7 | 81.9 |
| Compound 408 | | | | 88.5 | 84.9 |
| Compound 409 | | | | 88.1 | 92.2 |
| Compound 410 | | | | 96.4 | 86.1 |
| Compound 411 | | | | 95.9 | 81.8 |
| Compound 412 | | | | 99.9 | 89.1 |
| Compound 413 | | | | 100.3 | 93.8 |

TABLE 1-continued

| | | |
|---|---|---|
| Compound 414 | 100.8 | 81.0 |
| Compound 415 | 99.6 | 75.1 |
| Compound 416 | 100.0 | 77.7 |
| Compound 417 | 97.9 | 64.8 |
| Compound 418 | 99.5 | 70.4 |
| Compound 419 | 67.8 | |
| Compound 420 | 93.3 | 50.1 |
| Compound 421 | 71.3 | |
| Compound 422 | 47.5 | |
| Compound 423 | 59.2 | |
| Compound 424 | 58.7 | |
| Compound 425 | 83.6 | |
| Compound 426 | 95.7 | 100.7 |
| Compound 427 | 97.5 | 67.0 |
| Compound 428 | 101.3 | 99.2 |
| Compound 429 | 95.1 | 74.2 |
| Compound 430 | 97.9 | 89.2 |
| Compound 431 | 98.0 | 94.6 |
| Compound 432 | 92.2 | 82.9 |
| Compound 433 | 93.8 | 70.2 |
| Compound 434 | 95.6 | 90.5 |
| Compound 435 | 93.7 | 86.4 |
| Compound 436 | 94.5 | 49.0 |
| Compound 437 | 101.1 | 93.9 |
| Compound 438 | 82.2 | |
| Compound 439 | 95.0 | 100.2 |
| Compound 440 | 95.1 | 101.8 |
| Compound 441 | 14.7 | |
| Compound 442 | 40.2 | |
| Compound 443 | 31.3 | 43.0 |
| Compound 444 | 18.2 | 60.9 |
| Compound 445 | 93.0 | 81.6 |
| Compound 446 | 91.4 | 72.5 |
| Compound 447 | 89.2 | 72.2 |
| Compound 448 | 89.7 | 99.6 |
| Compound 449 | 91.6 | 65.9 |
| Compound 450 | 92.3 | 93.8 |
| Compound 451 | 94.2 | 62.7 |
| Compound 452 | 91.8 | 89.7 |
| Compound 453 | 89.4 | 97.1 |
| Compound 454 | 91.7 | 92.6 |
| Compound 455 | 93.2 | 91.7 |
| Compound 456 | 87.4 | 89.0 |

TABLE 1-continued

| | | |
|---|---|---|
| Compound 457 | 85.4 | 101.1 |
| Compound 458 | 86.5 | 91.9 |
| Compound 459 | 89.9 | 68.5 |
| Compound 460 | 94.5 | 76.3 |
| Compound 461 | 87.9 | 89.5 |
| Compound 462 | 83.5 | 92.1 |
| Compound 463 | 88.7 | 97.2 |
| Compound 464 | 99.6 | 98.3 |
| Compound 465 | 97.9 | 88.0 |
| Compound 466 | 99.3 | 88.8 |
| Compound 467 | 100.4 | 98.6 |
| Compound 468 | 96.9 | 75.8 |
| Compound 469 | 95.9 | 83.9 |
| Compound 470 | 91.6 | 80.8 |
| Compound 471 | 96.5 | 91.0 |
| Compound 472 | 102.0 | 94.4 |
| Compound 473 | 95.1 | 91.7 |
| Compound 474 | 93.0 | 79.0 |
| Compound 475 | 97.9 | 86.4 |
| Compound 476 | 100.0 | 86.1 |
| Compound 477 | 92.0 | 77.1 |
| Compound 478 | 104.4 | 86.0 |
| Compound 479 | 93.3 | 83.0 |
| Compound 480 | 93.1 | 77.4 |
| Compound 481 | 96.3 | 64.9 |
| Compound 482 | 90.7 | 72.3 |
| Compound 483 | 88.9 | |
| Compound 484 | 102.0 | 63.2 |
| Compound 485 | 103.2 | 95.5 |
| Compound 486 | 99.5 | 93.8 |
| Compound 487 | 99.6 | 90.4 |
| Compound 488 | 101.9 | 91.4 |
| Compound 489 | 103.3 | 98.4 |
| Compound 490 | 100.7 | 88.9 |
| Compound 491 | 88.9 | 75.7 |
| Compound 492 | 104.3 | 87.9 |
| Compound 493 | 104.7 | 88.3 |
| Compound 494 | 102.5 | 87.1 |
| Compound 495 | 104.1 | 89.9 |
| Compound 496 | 103.2 | 75.7 |
| Compound 497 | 102.0 | 66.5 |
| Compound 498 | 103.6 | 88.5 |
| Compound 499 | 106.7 | 89.1 |

TABLE 1-continued

| | | |
|---|---:|---:|
| Compound 500 | 102.7 | 81.6 |
| Compound 501 | 102.3 | 55.4 |
| Compound 502 | 107.6 | 86.3 |
| Compound 503 | 103.9 | 73.3 |
| Compound 504 | 96.6 | 54.0 |
| Compound 505 | 102.9 | 74.4 |
| Compound 506 | 88.6 | |
| Compound 507 | | 96.7 |
| Compound 508 | 100.1 | |
| Compound 509 | | |
| Compound 510 | 105.5 | 70.9 |
| Compound 511 | 99.0 | 85.4 |
| Compound 512 | 105.3 | 71.5 |
| Compound 513 | 98.8 | 55.2 |
| Compound 514 | 98.4 | 86.7 |
| Compound 515 | 102.9 | 62.4 |
| Compound 516 | 100.8 | 61.9 |
| Compound 517 | 93.7 | 42.7 |
| Compound 518 | | 83.5 |
| Compound 519 | | |
| Compound 520 | | |
| Compound 521 | | |
| Compound 522 | | |
| Compound 523 | | 82.5 |
| Compound 524 | | 75.0 |
| Compound 525 | | 98.0 |
| Compound 526 | | 88.9 |
| Compound 527 | | 89.7 |
| Compound 528 | | 94.0 |
| Compound 529 | | 100.2 |
| Compound 530 | | 97.2 |
| Compound 531 | | 100.5 |
| Compound 532 | | 53.8 |
| Compound 533 | | 98.9 |
| Compound 534 | | 98.3 |
| Compound 535 | | 102.1 |
| Compound 536 | | 98.4 |
| Compound 537 | | 101.4 |
| Compound 538 | | 103.4 |
| Compound 539 | | |
| Compound 540 | 96.3 | |
| Compound 541 | 97.1 | 75.8 |
| Compound 542 | 99.9 | 92.3 |

TABLE 1-continued

| | | |
|---|---|---|
| Compound 543 | 93.1 | 101.4 |
| Compound 544 | 47.5 | 100.5 |
| Compound 545 | | 101.2 |
| Compound 546 | | 96.9 |
| Compound 547 | | 85.4 |
| Compound 548 | | 99.8 |
| Compound 549 | | 99.7 |
| Compound 550 | | 98.6 |
| Compound 551 | | 100.9 |
| Compound 552 | | 97.3 |
| Compound 553 | | 94.2 |
| Compound 554 | | 88.0 |
| Compound 555 | | |
| Compound 556 | | |
| Compound 557 | | |
| Compound 558 | | |
| Compound 559 | | |
| Compound 560 | | |
| Compound 561 | | |
| Compound 562 | | |
| Compound 563 | | |
| Compound 564 | | |
| Compound 565 | | |
| Compound 566 | | |
| Compound 567 | | |
| Compound 568 | | |

INDUSTRIAL APPLICABILITY

The compound of the present invention is an excellent Edg-1(S1P$_1$) ligand. Hence, it is useful as an agent for the treatment or prevention of autoimmune diseases such as Crohn disease, irritable colitis, Sjögren syndrome, multiple sclerosis, and systemic lupus erythematosus, and diseases such as rheumatoid arthritis, asthma, atopic dermatitis, rejection reaction after organ transplantation, cancer, retinopathy, psoriasis, osteoarthrosis, and age-related macular degeneration.

The invention claimed is:

1. A compound represented by the following formula (I) or a pharmaceutically acceptable salt thereof

[Chemical formula 1]

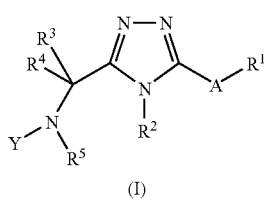

(I)

{where

A represents an oxygen atom,

R$^1$ represents an alkyl group having 1 to 16 carbon atoms, an alkenyl group having 2 to 8 carbon atoms, an alkynyl group having 2 to 8 carbon atoms, an alkyl group having 1 to 6 carbon atoms that is substituted by any of the following groups (1) to (28)

(1) (a) phenyl group(s);

(2) a phenyl group substituted by 1 to 5 groups selected from (2-1) a phenyl group, (2-2) a cyano group, (2-3) a halogen atom, (2-4) an alkyl group having 1 to 6 carbon atoms, (2-5) a trifluoromethyl group, (2-6) a methoxycarbonyl group, (2-7) an alkylthio group having 1 to 6 carbon atoms, (2-8) a dimethylamino group, (2-9) a nitro group, and (2-10) an acetamido group;

(3) a cycloalkyl group having 3 to 8 carbon atoms;

(4) a hydroxyl group;

(5) an alkylthio group having 1 to 6 carbon atoms;

(6) an alkoxy group having 1 to 6 carbon atoms;

(7) a benzyloxy group;

(8) a phenoxy group;

(9) a trifluoromethyl group;

(10) a difluoromethyl group;
(11) a benzenesulfonyl group;
(12) a naphthyl group;
(13) a tricycloalkyl group having 7 to 10 carbon atoms;
(14) a 1-phenylethyl group,
(15) an imidazolyl group;
(16) an indolyl group;
(17) a pyridyl group;
(18) an oxetanyl group;
(19) an oxoranyl group;
(20) a methylpiperidinyl group;
(21) a benzylpiperidinyl group;
(22) a morpholino group;
(23) a 2-oxopyrrolidin-1-yl group;
(24) a 2-oxoimidazolidin-1-yl group;
(25) a group represented by the formula —$CO_2R^{11}$; where $R^{11}$ represents a hydrogen atom or an alkyl group having 1 to 6 carbon atoms;
(26) a group represented by the following chemical formula 2:

[Chemical formula 2]

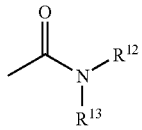

where $R^{12}$ and $R^{13}$ each represent a hydrogen atom or an alkyl group having 1 to 6 carbon atoms,
(27) a group represented by the following chemical formula 3

[Chemical formula 3]

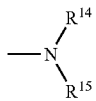

where $R^{14}$ and $R^{15}$ each represent a hydrogen atom, an alkyl group having 1 to 6 carbon atoms, a phenyl group, or a 4-pyridylcarbonyl group; and
(28) a group represented by the formula

—$COR^{16}$ where $R^{16}$ represents (28-1) an alkyl group having 1 to 6 carbon atoms, or (28-2) a phenyl group; an alkenyl group having 2 to 8 carbon atoms that is substituted by a phenyl group or a benzyloxy group, an alkynyl group having 2 to 8 carbon atoms which has been substituted by a phenyl group, a cycloalkyl group having 3 to 8 carbon atoms, a cycloalkyl group having 3 to 8 carbon atoms in which the benzene rings have been condensed, an oxoranyl group, a methylpiperidinyl group, or a group represented by the formula 4

[Chemical formula 4]

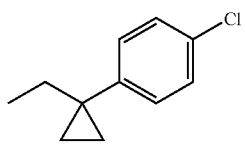

$R^2$ represents an alkyl group having 1 to 6 carbon atoms, a cycloalkyl group having 3 to 8 carbon atoms, a phenyl group, or an alkyl group having 1 to 6 carbon atoms which is substituted by any of the following groups (29) to (34):
(29) a phenyl group;
(30) an alkoxy group having 1 to 6 carbon atoms;
(31) a morpholino group;
(32) a piperidino group;
(33) a group represented by the following chemical formula 5:

[Chemical formula 5]

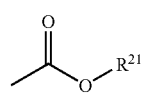

where $R^{21}$ represents a hydrogen atom or an alkyl group having 1 to 6 carbon atoms, and
(34) a group represented by the following chemical formula 6

[Chemical formula 6]

where $R^{22}$ and $R^{23}$ each represents a hydrogen atom or an alkyl group having 1 to 6 carbon atoms,
$R^3$ represents a hydrogen atom or an alkyl group having 1 to 6 carbon atoms,
$R^4$ represents a hydrogen atom, an alkyl group having 1 to 6 carbon atoms, a benzyl group, a benzyl group that is substituted by 1 to 2 groups selected from the following groups (a) to (f): (a) a phenyl group, (b) a halogen atom, (c) a methyl group, (d) a methoxy group, (e) a trifluoromethyl group and (f) a hydroxyl group; a phenethyl group, an alkyl group having 1 to 6 carbon atoms substituted by a group selected from the following (g) to (i): (g) an alkoxy group having 1 to 6 carbon atoms, (h) a halogen atom, and (i) a hydroxyl group; or a phenyl group, or
$R^3$ and $R^4$ together form a 3- to 6-membered saturated hydrocarbon ring,
$R^5$ represents a hydrogen atom or an alkyl group having 1 to 6 carbon atoms, and
Y represents a group represented by the formula

[Chemical formula 7]

where $R^6$ represents an alkyl group having 1 to 10 carbon atoms, an alkenyl group having 2 to 8 carbon atoms, an alkyl group having 1 to 10 carbon atoms that is substituted with 1 to 5 groups selected from the following groups (j) to (p): (j) a phenyl group, (k) a phenyl group substituted with 1 to 5 substituents selected from the following substituents (k-1) to (k-37): (k-1) a phenyl group, (k-2) a phenyl group substituted with a methoxy group or an acetyl group, (k-3) an oxazolyl group, (k-4) a pyrazolyl group, (k-5) a methylpyrimidinyl group, (k-6) a cyano group, (k-7) a halogen atom, (k-8) an alkyl group having 1 to 6 carbon atoms, (k-9) a trifluoromethyl group; (k-10) a trifluoromethoxy group, (k-11) a difluoromethoxy group, (k-12) a hydroxyl group, (k-13) an alkoxy group having 1 to 6 carbon atoms, (k-14) a cyanoethoxy group, (k-15) a phenoxy group, (k-16) a phenoxy group substituted with a methoxy group, (k-17) a pyridinyloxy group, (k-18) an acetyl group, (k-19) a benzoyl group, (k-20) a pyridinecarbonyl group, (k-21) a methoxycarbonyl group, (k-22) a methoxycarbonylethyl group, (k-23) an akylthio group having 1 to 6 carbon atoms, (k-24) a dimethylamino group, (k-25) a nitro group, (k-26) an acetamido group, (k-27) a sulfamoyl group, (k-28) a methanesulfonyl group, (k-29) a benzenesulfonyl group, (k-30) a pyrrolidinesulfonyl group, (k-31) a morpholinesulfonyl group, (k-32) a methylureido group, (k-33) a butylureido group, (k-34) a methoxyethylureido group, (k-35) a trimethylureido group, (k-36) a morpholinecarbonylamino group, and (k-37) a pyridinylethoxycarbonylamino group; (l) a cycloalkyl group having 3 to 8 carbon atoms, (m) a halogen atom,(n) a naphthyl group, (o) a heterocyclic group, and (p) a heterocyclic group substituted with 1 to 5 substitutes selected from the following groups (p-1) to (p-6): (p-1) a halogen atom, (p-2) an alkyl group having 1 to 6 carbon atoms, (p-3) a methoxycarbonyl group, (p-4) an ethoxcarbonyl group (p-5) a benzenesulfonyl group, and (p-6) an oxazolyl group;
an alkenyl group having 2 to 8 carbon atoms that is substituted by 1 to 5 groups selected from the groups (j) to (p) mentioned above as substituents of the alkyl group; a phenyl group, a phenyl group that is substituted with 1 to 5 substituents selected from the above groups of substituents (k-1) to (k-37), a naphthyl group, a naphthyl group substituted by a dimethylamino group, a heterocyclic group, or a heterocyclic group substituted with 1 to 5 substituents selected from the above groups (p-1) to (p-6).

2. The compound or a pharmaceutically acceptable salt thereof according to claim 1, wherein in formula (I)
$R^1$ represents an alkyl group having 1 to 16 carbon atoms, an alkenyl group having 2 to 8 carbon atoms, an alkynyl group having 2 to 8 carbon atoms, an alkyl group having 1 to 6 carbon atoms that is substituted with any of the following groups (1) to (30)
(1) a phenyl group(s);
(2) a phenyl group substituted by 1 to 2 groups selected from (2-1) a phenyl group, (2-2) a cyano group, (2-3) a halogen atom, (2-4) an alkyl group having 1 to 6 carbon atoms, (2-5) a trifluoromethyl group, (2-6) a methoxycarbonyl group, (2-7) an alkylthio group having 1 to 6 carbon atoms, (2-8) a dimethylamino group, (2-9) a nitro group, and (2-10) an acetamido group;
(3) a cycloalkyl group having 3 to 8 carbon atoms;
(4) a hydroxyl group;
(5) an alkylthio group having 1 to 6 carbon atoms;
(6) an alkoxy group having 1 to 6 carbon atoms;
(7) a benzyloxy group;
(8) a phenoxy group;
(9) a trifluoromethyl group;
(10) a difluoromethyl group;
(11) a benzenesulfonyl group;
(12) a naphthyl group;
(13) a tricycloalkyl group having 7 to 10 carbon atoms;
(14) a 1-phenylethyl group;
(15) a 1-imidazolyl group;
(16) a 3-indolyl group;
(17) a 2-pyridyl group;
(18) a 4-pyridyl group;
(19) a 2-oxetanyl group;
(20) a 3-oxoranyl group;
(21) a 3-methylpiperidinyl group;
(22) a 4-methylpiperidinyl group;
(23) a 4-benzylpiperidinyl group;
(24) a morpholino group;
(25) a 2-oxopyrrolidin-1-yl group;
(26) a 2-oxoimidazolidin-1-yl group;
(27) a group represented by the formula

where $R^{11}$ represents a hydrogen atom or an alkyl group having 1 to 6 carbon atoms,
(28) a group represented by the formula 2:

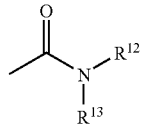

[Chemical formula 2]

where $R^{12}$ and $R^{13}$ each represent a hydrogen atom or an alkyl group having 1 to 6 carbon atoms,
(29) a group represented by the formula 3

[Chemical formula 3]

where $R^{14}$ and $R^{15}$ each represent a hydrogen atom, an alkyl group having 1 to 6 carbon atoms, a phenyl group, or a 4-pyridylcarbonyl group, and
(30) a group represented by the formula —$COR^{16}$
where $R^{16}$ represents an alkyl group having 1 to 6 carbon atoms, or a phenyl group,
an alkenyl group having 2 to 8 carbon atoms which has been substituted by a phenyl group or a benzyloxy group, an alkynyl group having 2 to 8 carbon atoms which has been substituted by a phenyl group, a cycloalkyl group having 3 to 8 carbon atoms, a cycloalkyl group having 3 to 8 carbon atoms in which the benzene rings have been condensed, an oxoranyl group, a 4-methylpiperidinyl group, or a group represented by the formula 4

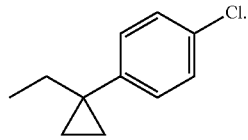

[Chemical formula 4]

3. The compound or the pharmaceutically acceptable salt thereof according to claim 2, wherein in the formula (I) $R^5$ is a hydrogen atom.

4. The compound or the pharmaceutically acceptable salt thereof according to claim 2, wherein in the formula (I) $R^2$ is an alkyl group having 1 to 4 carbon atoms, a cycloalkyl group having 3 to 6 carbon atoms, or an alkyl group having 1 to 4 carbon atoms that is substituted by a methoxy group or a morpholino group.

5. The compound or the pharmaceutically acceptable salt thereof according to claim 2, wherein in the formula (I) $R^2$ is a methyl group, an ethyl group, an isopropyl group, or a cyclopropyl group.

6. The compound or the pharmaceutically acceptable salt thereof according to claim 2, wherein in the formula (I) $R^3$ is a hydrogen atom.

7. The compound or the pharmaceutically acceptable salt thereof according to claim 6, wherein in the formula (I) $R^4$ is a methyl group, an ethyl group, a benzyl group, or a benzyl group that is substituted by 1 to 2 groups selected from the following groups (a) to (f): (a) a phenyl group, (b) a halogen atom, (c) a methyl group, (d) a methoxy group, (e) a trifluoromethyl group and (f) a hydroxyl group.

8. The compound or the pharmaceutically acceptable salt thereof according to claim 6, wherein in the formula (I) $R^4$ is a methyl group, a benzyl group, or a benzyl group mono- or di-substituted by a substituent selected from a halogen atom and a methyl group.

9. The compound or the pharmaceutically acceptable salt thereof according to claim 8, wherein in the formula (I) $R^2$ is a methyl group, an ethyl group, an isopropyl group, or a cyclopropyl group.

10. The compound or the pharmaceutically acceptable salt thereof according to claim 6, wherein in the formula (I) $R^1$ is an alkyl group having 1 to 6 carbon atoms, an alkenyl group having 3 to 5 carbon atoms, a 2-propynyl group, a cycloalkyl group having 3 to 6 carbon atoms, or an alkyl group having 1 to 6 carbon atoms that is substituted by a cycloalkyl group having 3 to 6 carbon atoms, a trifluoromethyl group, a phenyl group, a hydroxyl group, a methoxy group, a dimethylamino group, or a morpholino group.

11. The compound or the pharmaceutically acceptable salt thereof according to claim 6, wherein in the formula (I) $R^1$ is a methyl group, an ethyl group, a propyl group, an isopropyl group, a cyclobutyl group, a cyclopentyl group, a cyclopropylmethyl group, or a 3-methoxypropyl group.

12. The compound or the pharmaceutically acceptable salt thereof according to claim 11, wherein in the formula (I) $R^4$ is a methyl group, a benzyl group, or a benzyl group mono- or di-substituted by a substituent selected from a halogen atom and a methyl group.

13. The compound or the pharmaceutically acceptable salt thereof according to claim 12, wherein in the formula (I) $R^2$ is a :methyl group, an ethyl group, an isopropyl group, or a cyclopropyl group.

14. The compound or the pharmaceutically acceptable salt thereof according to claim 6, wherein in the formula (I) $R^6$ is a phenyl group, a phenyl group substituted by 1 to 3 groups selected from a halogen atom, an alkyl group having 1 to 4 carbon atoms, a trifluoromethyl group, an alkoxy group having 1 to 6 carbon atoms, a trifluoromethoxy group, a difluoromethyl group, an acetyl group, a nitro group, and a cyano group, a 2-naphthyl group, a 2-benzothienyl group, a 2-benzofuranyl group, a 2-thienyl group substituted by 1 or 2 halogen atoms, or a benzo[1,2,5]thiadiazolyl group.

15. The compound or the pharmaceutically acceptable salt thereof according to claim 6, wherein in the formula (I) $R^6$ is a phenyl group, "a phenyl group substituted by 1 or 2 groups selected from a halogen atom, a methyl group, a trifluoromethyl group, a methoxy group, and a trifluoromethoxy group, a 2-naphthyl group, a 2-benzothienyl group, or a 2-benzofuranyl group.

16. The compound or the pharmaceutically acceptable salt thereof according to claim 15, wherein in the formula (I) $R^1$ is a methyl group, an ethyl group, a propyl group, an isopropyl group, a cyclobutyl group, a cyclopentyl group, a cyclopropylmethyl group, or a 3-methoxypropyl group.

17. The compound or the pharmaceutically acceptable salt thereof according to claim 16, wherein in the formula (I) $R^4$ is a methyl group, a benzyl group, or a benzyl group mono- or di-substituted by a substituent selected from a halogen atom and a methyl group.

18. The compound or the pharmaceutically acceptable salt thereof according to claim 17, wherein in the formula (I) $R^2$ is a methyl group, an ethyl group, an isopropyl group, or a cyclopropyl group.

19. A compound represented by the following formula (I) or a pharmaceutically acceptable salt thereof

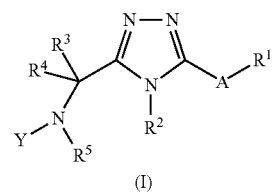

[Formula 1]

where

A represents an oxygen atom, $R^1$ represents an alkyl group having 1 to 16 carbon atoms, an alkenyl group having 2 to 8 carbon atoms, an alkynyl group having 2 to 8 carbon atoms, an alkyl group having 1 to 6 carbon atoms that is substituted by any of the following groups (1) to (30):

(1) a phenyl group(s);

(2) a phenyl group substituted by 1 to 2 groups selected from (2-1) a phenyl group, (2-2) a cyano group, (2-3) a halogen atom, (2-4) an alkyl group having 1 to 6 carbon atoms, (2-5) a trifluoromethyl group, (2-6) a methoxycarbonyl group, (2-7) an alkylthio group having 1 to 6 carbon atoms, (2-8) a dimethylamino group, (2-9) a nitro group, and (2-10) an acetamido group;

(3) a cycloalkyl group having 3 to 8 carbon atoms;

(4) a hydroxyl group;

(5) an alkylthio group having 1 to 6 carbon atoms;

(6) an alkoxy group having 1 to 6 carbon atoms;

(7) a benzyloxy group;

(8) a phenoxy group;

(9) a trifluoromethyl group;

(10) a difluoromethyl group;

(11) a benzenesulfonyl group;

(12) a naphthyl group;

(13) a tricycloalkyl group having 7 to 10 carbon atoms;

(14) a 1-phenylethyl group;

(15) a 1-imidazolyl group;

(16) a 3-indolyl group;

(17) a 2-pyridyl group;

(18) a 4-pyridyl group;

(19) a 2-oxetanyl group;

(20) a 3-oxoranyl group;

(21) a 3-methylpiperidinyl group;

(22) a 4-methylpiperidinyl group;

(23) a 4-benzylpiperidinyl group;

(24) a morpholino group;

(25) a 2-oxopyrrolidin-1-yl group;

(26) a 2-oxoimidazolidin-1-yl group;

(27) a group represented by the formula —$CO_2R^{11}$; where $R^{11}$ represents a hydrogen atom or an alkyl group having 1 to 6 carbon atoms;

(28) a group represented by the following chemical formula 2

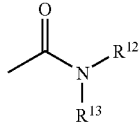

[Chemical formula 2]

where $R^{12}$ and $R^{13}$ each represent a hydrogen atom or an alkyl group having 1 to 6 carbon atoms,
(29) a group represented by the formula 3

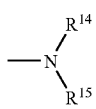

[Chemical formula 3]

where $R^{14}$ and $R^{15}$ each represent a hydrogen atom, an alkyl group having 1 to 6 carbon atoms, a phenyl group, or a 4-pyridylcarbonyl group, and
(30) a group represented by the formula —$COR^{16}$, where $R^{16}$ represents (30-1) an alkyl group having 1 to 6 carbon atoms, or (30-2) a phenyl group;
an alkenyl group having 2 to 8 carbon atoms which has been substituted by a phenyl group or a benzyloxy group, an alkynyl group having 2 to 8 carbon atoms which has been substituted by a phenyl group, a cycloalkyl group having 3 to 8 carbon atoms, a cycloalkyl group having 3 to 8 carbon atoms in which the benzene rings have been condensed, an oxoranyl group, a methylpiperidinyl group, or a group represented by the formula 4

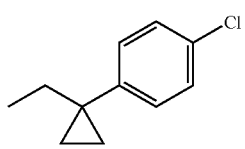

[Chemical formula 4]

$R^2$ represents an alkyl group having 1 to 6 carbon atoms, a cycloalkyl group having 3 to 8 carbon atoms, a phenyl group, or an alkyl group having 1 to 6 carbon atoms that is substituted by a group selected from the following groups (1) to (6):
(1) a phenyl group,
(2) an alkoxy group having 1 to 6 carbon atoms,
(3) a morpholino group,
(4) a piperidino group,
(5) a group represented by the formula

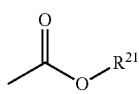

where $R^{21}$ represents a hydrogen atom or an alkyl group having 1 to 6 carbon atoms, and (6) a group represented by the formula

where $R^{22}$ and $R^{23}$ each represent a hydrogen atom or an alkyl group having 1 to 6 carbon atoms,
$R^3$ represents a hydrogen atom,
$R^4$ represents a hydrogen atom, an alkyl group having 1 to 6 carbon atoms, a benzyl group, a benzyl group that is substituted by 1 to 2 groups selected from the following groups (a) to (f): (a) a phenyl group, (b) a halogen atom, (c) a methyl group, (d) a methoxy group, (e) a trifluoromethyl group and (f) a hydroxyl group; a phenethyl group, an alkyl group having 1 to 6 carbon atoms that is substituted with (g) an alkoxy group having 1 to 6 carbon atoms, (h) a halogen atom or (i) a hydroxyl group; or a phenyl group;
or $R^3$ and $R^4$ together form a 3- to 6-membered saturated hydrocarbon ring;
$R^5$ represents a hydrogen atom, and
Y represents a hydrogen atom.
20. A compound represented by the following formula (I) or a pharmaceutically acceptable salt thereof,

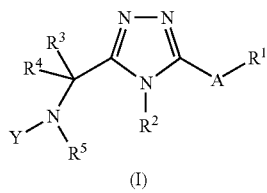

[Formula 1]

(I)

where A represents an oxygen atom,
$R^1$ represents an alkyl group having 1 to 16 carbon atoms, an alkenyl group having 2 to 8 carbon atoms, an alkynyl group having 2 to 8 carbon atoms, an alkyl group having 1 to 6 carbon atoms that is substituted by any of the following groups (1) to (30):
(1) a phenyl group(s);
(2) a phenyl group substituted by 1 to 2 groups selected from (2-1) a phenyl group, (2-2) a cyano group, (2-3) a halogen atom, (2-4) an alkyl group having 1 to 6 carbon atoms, (2-5) a trifluoromethyl group, (2-6) a methoxycarbonyl group, (2-7) an alkylthio group having 1 to 6 carbon atoms, (2-8) a dimethylamino group, (2-9) a nitro group, and (2-10) an acetamido group;
(3) a cycloalkyl group having 3 to 8 carbon atoms;
(4) a hydroxyl group;
(5) an alkylthio group having 1 to 6 carbon atoms;
(6) an alkoxy group having 1 to 6 carbon atoms;
(7) a benzyloxy group;
(8) a phenoxy group;
(9) a trifluoromethyl group;
(10) a difluoromethyl group;
(11) a benzenesulfonyl group;
(12) a naphthyl group;
(13) a tricycloalkyl group having 7 to 10 carbon atoms;
(14) a 1-phenylethyl group;
(15) a 1-imidazolyl group;
(16) a 3-indolyl group;
(17) a 2-pyridyl group;
(18) a 4-pyridyl group;

(19) a 2-oxetanyl group;
(20) a 3-oxoranyl group;
(21) a 3-methylpiperidinyl group;
(22) a 4-methylpiperidinyl group;
(23) a 4-benzylpiperidinyl group;
(24) a morpholino group;
(25) a 2-oxopyrrolidin-1-yl group;
(26) a 2-oxoimidazolidin-1-yl group;
(27) a group represented by the formula —$CO_2R^{11}$; where $R^{11}$ represents a hydrogen atom or an alkyl group having 1 to 6 carbon atoms;
(28) a group represented by the following chemical formula 2

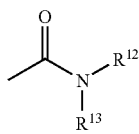

[Chemical formula 2]

where $R^{12}$ and $R^{13}$ each represent a hydrogen atom or an alkyl group having 1 to 6 carbon atoms,
(29) a group represented by the formula 3

[Chemical formula 3]

where $R^{14}$ and $R^{15}$ each represent a hydrogen atom, an alkyl group having 1 to 6 carbon atoms, a phenyl group, or a 4-pyridylcarbonyl group,
(30) a group represented by the formula —$COR^{16}$, where $R^{16}$ represents (30-1) an alkyl group having 1 to 6 carbon atoms, or (30-2) a phenyl group,
an alkenyl group having 2 to 8 carbon atoms that is substituted by a phenyl group or a benzyloxy group,
an alkynyl group having 2 to 8 carbon atoms which has been substituted by a phenyl group, a cycloalkyl group having 3 to 8 carbon atoms, a cycloalkyl group having 3 to 8 carbon atoms in which the benzene rings have been condensed, an oxoranyl group, a 4-methylpiperidinyl group, or a group represented by the formula 4

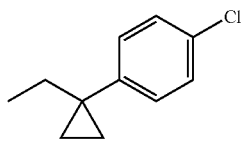

[Chemical formula 4]

$R^2$ represents an alkyl group having 1 to 4 carbon atoms, a cycloalkyl group having 3 to 6 carbon atoms, or an alkyl group having 1 to 4 carbon atoms that is substituted by a methoxy group or a morpholino group,
$R^3$ represents a hydrogen atom or an alkyl group having 1 to 6 carbon atoms,
$R^4$ represents a hydrogen atom, an alkyl group having 1 to 6 carbon atoms, a benzyl group, a benzyl group that is substituted by 1 to 2 groups selected from the following groups (a) to (f): (a) a phenyl group, (b) a halogen atom, (c) a methyl group, (d) a methoxy group, (e) a trifluoromethyl group and (f) a hydroxyl group; a phenethyl group, an alkyl group having 1 to 6 carbon atoms that is substituted with (g) an alkoxy group having 1 to 6 carbon atoms, (h) a halogen atom or (i) a hydroxyl group; or a phenyl group;
or $R^3$ and $R^4$ together form a 3- to 6-membered saturated hydrocarbon ring;
$R^5$ represents a hydrogen atom, and
Y represents a hydrogen atom.

21. The compound or the pharmaceutically acceptable salt thereof according to claim 20 wherein in the formula (I) $R^2$ is a methyl group, an ethyl group, an isopropyl group, or a cyclopropyl group.

22. The compound or the pharmaceutically acceptable salt thereof according to claim 19, wherein in the formula (I) $R^4$ is a methyl group, a benzyl group, or a benzyl group mono- or di-substituted by a substituent selected from a halogen atom and a methyl group, and $R^2$ is a methyl group, an ethyl group, an isopropyl group, or a cyclopropyl group.

23. The compound or the pharmaceutically acceptable salt thereof according to claim 19, wherein in the formula (I) $R^1$ is an alkyl group having 1 to 6 carbon atoms, an alkenyl group having 3 to 5 carbon atoms, a 2-propynyl group, a cycloalkyl group having 3 to 6 carbon atoms, or an alkyl group having 1 to 6 carbon atoms which has been substituted by a cycloalkyl group having 3 to 6 carbon atoms, a trifluoromethyl group, a phenyl group, a hydroxyl group, a methoxy group, a dimethylamino group, or a morpholino group.

24. The compound or the pharmaceutically acceptable salt thereof according to claim 19, wherein in the formula (I) $R^1$ is a methyl group, an ethyl group, a propyl group, an isopropyl group, a cyclobutyl group, a cyclopentyl group, a cyclopropylmethyl group, or a 3-methoxypropyl group.

25. The compound or the pharmaceutically acceptable salt thereof according to claim 24, wherein in the formula (I) $R^4$ is a methyl group, a benzyl group, or a benzyl group mono- or di-substituted by a substituent selected from a halogen atom and a methyl group.

26. The compound or the pharmaceutically acceptable salt thereof according to claim 25, wherein in the formula (I) $R^2$ is a methyl group, an ethyl group, an isopropyl group, or a cyclopropyl group.

* * * * *